(12) United States Patent
Amo et al.

(10) Patent No.: US 9,109,257 B2
(45) Date of Patent: Aug. 18, 2015

(54) PROGNOSTIC METHOD

(75) Inventors: Jokin Del Amo, Getxo (ES); Diego Tejedor Hernández, Vizcaya (ES); Antonio Martínez Martínez, Vizcaya (ES); Laureano Simón Buela, Guipúzcoa (ES); Juan Morote Robles, Barcelona (ES)

(73) Assignee: Progenika Biopharma, S.A., Derio (ES)

( * ) Notice: Subject to any disclaimer, the term of this patent is extended or adjusted under 35 U.S.C. 154(b) by 1337 days.

(21) Appl. No.: 12/309,208

(22) PCT Filed: Jul. 12, 2007

(86) PCT No.: PCT/IB2007/002364
§ 371 (c)(1),
(2), (4) Date: Dec. 14, 2009

(87) PCT Pub. No.: WO2008/010084
PCT Pub. Date: Jan. 24, 2008

(65) Prior Publication Data
US 2010/0185429 A1    Jul. 22, 2010

(30) Foreign Application Priority Data
Jul. 12, 2006 (GB) .................................. 0613840.8

(51) Int. Cl.
*C12Q 1/68* (2006.01)
*C12P 19/34* (2006.01)
*A61K 39/395* (2006.01)

(52) U.S. Cl.
CPC ........ *C12Q 1/6886* (2013.01); *C12Q 2600/106* (2013.01); *C12Q 2600/118* (2013.01); *C12Q 2600/16* (2013.01); *C12Q 2600/172* (2013.01)

(58) Field of Classification Search
CPC ........... C12Q 1/6886; C12Q 2600/106; C12Q 2600/118; C12Q 2600/16; C12Q 2600/172; C12Q 1/6837; C12Q 1/6827; G01N 33/533; G01N 33/582
See application file for complete search history.

(56) References Cited

U.S. PATENT DOCUMENTS

2005/0032065 A1    2/2005    Afar et al.
2006/0110759 A1    5/2006    Paris et al.

OTHER PUBLICATIONS

Juppner H. Bone vol. 17, No. 2 Supplement, Aug. 1995, pp. 39S-42S.*
Wall J.D. et al. Nature Reviews, vol. 4, Aug. 2003, pp. 587-597.*
Hegele R.A. Arterioscler Thromb Vasc Biol. 2002;22:1058-1061.*
Pal P. et al. The Prostate (2009) 69:1548-1556.*
Zill P. et al. Molecular Psychiatry (2004) 9, pp. 1030-1036.*
Carlson et al. Am. J. Hum. Genet. (2004) 74:106-120.*
Bustamante C.D. et al. Nature 437, 1153-1157 (Oct. 20, 2005).*
dbSNP Submitted SNP(ss) Details: ss48420853 (Nov. 30, 2005) pp. 1-8 printed from http://www.ncbi.nlm.nih.gov/.*
Chen et al. "Relation of Polymorphism in the Promotor Region for the Human Osteocalcin Gene to Bone Mineral Density and Occurrence of Osteoporosis in Postmenopausal Chinese Women in Taiwan," *Journal of Clinical Laboratory Analysis*, vol. 15, pp. 251-255, 2001.
Dohi et al. "A Novel Polymorphism in the Promoter Region for the Human Osteocalcin Gene: The Possibility of a Correlation with Bone Mineral Density in Postmenopausal Japanese Women," *Journal of Bone and Mineral Research*, vol. 13, No. 10, pp. 1633-1639, 1988.
Gustavsson et al. "Osteocalcin Gene Polymorphism is Related to Bone Density in Healthy Adolescent Females," *Osteoporosis International*, vol. 11, pp. 847-851, 2000.
Nam et al. "The Use of Genetic markers to Determine Risk for Prostate Cancer at Prostate Biopsy," *Clinical Cancer Research*, vol. 11, No. 23, pp. 8391-8397, 2005.
Pal et al. "Tagging SNPs in the kallikrein genes 3 and 2 on 19q13 and their associations with prostate cancer in men of European origin," *Human Genetics*, vol. 122, pp. 251-259, 2007.
Extended European Search Report, European Pat. App. No. 11175108.7, Jan. 27, 2012 (7 pages).
Extended European Search Report, European Pat. App. No. 11175100.4, Jan. 27, 2012 (8 pages).
Acevedo et al., "Positive correlation between single or combined genotypes of CYP1A1 and GSTM1 in relation to prostate cancer in Chilean people," *Prostate*, vol. 57, pp. 111-117, 2003.
Aktas et al., "CYP1A1 and GSTM1 polymorphic genotypes in patients with prostate cancer in a Turkish population," *Cancer Genetics and Cytogenetics*, vol. 154, pp. 81-85, 2004.
Bova et al., "Homozygous deletion and frequent allelic loss of chromosome 8p22 loci in human prostate cancer," *Cancer Research*, vol. 53, pp. 3869-3873, 1993.
Chang et al., "Polymorphisms in the CYP1A1 gene are associated with prostate cancer risk," *Int. J. Cancer*, vol. 106, pp. 375-378, 2003.
Iavarone et al., "PAGE4 is a cytoplasmic protein that is expressed in normal prostate and in prostate cancers," *Mol. Cancer Therapeutics*, vol. 1, pp. 329-335, 2002.
Narita et al., "Association of lipoprotein lipase gene polymorphism with risk of prostate cancer in a Japanese population," *Int. J. Cancer*, vol. 112, pp. 872-876, 2004.

(Continued)

*Primary Examiner* — Stephen Kapushoc
(74) *Attorney, Agent, or Firm* — Klarquist Sparkman, LLP

(57) ABSTRACT

A method for prognosing recurrence of prostate cancer (PCa) in a subject following prostatectomy using the outcomes of selected single nucleotide polymorphisms (SNPs) and clinical variables. A method for genotyping PCa associated genetic variations comprising use of a DNA microarray. A microarray for use in the described methods.

8 Claims, 42 Drawing Sheets

(56) References Cited

OTHER PUBLICATIONS

Sato et al., "Clinical significance of alterations of chromosome 8 in high-grade, advanced, nonmetastatic prostate carcinoma," *J. Nat. Cancer Institute*, vol. 91, No. 18, pp. 1574-1580, 1999.

Van Der Lende et al., "Leptin gene polymorphisms and their phenotypic associations," *Vitamins and Hormones*, vol. 71, pp. 373-404, 2005.

Nam et al., "V89L Polymorphism of Type-2, 5-Alpha Reductase Enzyme Gene Predicts Prostate Cancer Presence and Progression," *Urology*, vol. 57, No. 1, pp. 199-204, 2001.

Powell et al., "CYP3A4 Genetic Variant and Disease-Free Survival Among White and Black Men After Radical Prostatectomy," *Journal of Urology*, vol. 172, pp. 1848-1852, 2004.

Nam et al., "Single Nucleotide Polymorphism of the Human Kallikrein-2 Gene Highly Correlates with Serum Human Kallikrein-2 Levels and in Combination Enhances Prostate Cancer Detection," *Journal of Clinical Oncology*, vol. 21, No. 12, pp. 2312-2319, 2003.

Nam et al., "Variants of the hK2 Protein Gene (KLK2) Are Associated with Serum hK2 Levels and Predict the Presence of Prostate Cancer at Biopsy," *Clinical Cancer Research*, vol. 12, pp. 6452-6458, 2006.

Wu et al., "Osteocalcin Gene Hind III C/T Polymorphism Is a Biomarker for Prostate Cancer and Responsiveness to Hormone Therapy," *European Urology*, vol. 43, pp. 197-200, 2003.

Huang et al., "Association of vitamin D receptor FokI polymorphism with prostate cancer risk, clinicopathological features and recurrence of prostate specific antigen after radical prostatectomy," *Int. J. Cancer*, vol. 119, pp. 1902-1907, 2006.

Powell et al., "CYP3A4 Genetic Variant and Disease-Free Survival among White and Black Men after Radical Prostatectomy," *J. Urol.*, vol. 172, pp. 1848-1852, 2004.

Williams et al., "Vitamin D Receptor Gene Polymorphisms and Disease Free Survival After Radical Prostatectomy," *The Prostate*, vol. 61, pp. 267-275, 2004.

\* cited by examiner

Figure 1A: Table 1A

| SNP code | Gene name | Gene Symbol | SNP | rs ID |
|---|---|---|---|---|
| 1 | B-cell CLL/lymphoma 2, transcript variant 1 | BCL2 | A20G | rs1801018 |
| 2 | Cyclin-dependent kinase inhibitor 1B | CDKN1B | C-79T | rs34330 |
| 3 | CHK2 checkpoint homolog (isoform 1) | CHEK2 | T470C, Ile157Thr | rs17879961 |
| 4 | UDP-glucuronosyl-transferase | UGT2B15 | G225T, Asp75Tyr | rs1902023 |
| 5 | Beta-17-hydroxysteroid dehydrogenase | HSD17B3 | Gly289Ser | rs2066479 |
| 6 | Beta-3-hydroxysteroid dehydrogenase B1 | HSD3B1 | Asn367Thr | rs1047303 |
| 7 | Beta-3-hydroxysteroid dehydrogenases B2 | HSD3B2 | C7519G | rs9282704 |
| 8 | Kallikrein 10 | KLK10 | Ala50Ser | rs3745535 |
| 9 | Kallikrein-3 | KLK2 | Arg250Trp | rs198977 |
| 10 | v-erb-b2 erythroblastic leukemia vir oncogene | HER2 | Ile388 | rs1801200 |
| 11 | Glutation-S-transferase | GSTT1 | Null allele | Not available |
| 12 | Glutation-S-transferase | GSTM1 | Null allele | Not available |
| 13 | Cytochrome P450, family 1, subfamily B, pp1 | CYP1B1 | C1294G,Val432Leu | rs1056836 |
| 14 | Human oxoguanine glycosylase 1 | OGG1 | G977C | rs1052133 |
| 15 | Alpha 5 -reductase type II gene | SRD5A2 | Ala49Thr | Not available |
| 16 | Alpha 5 -reductase type II gene | SRD5A2 | Val89Leu | Not available |
| 17 | Endothelial nitric oxide synthase | NOS3 | Glu298Asp | rs1799983 |
| 18 | Tumor necrosis factor alpha | TNFA | G-308A | rs1800629 |
| 19 | Estrogen receptor | ESR1 | T-C codon 10 | rs17847075 |
| 20 | Ataxia telangiectasia mutated | ATM | G3161C, Pro1054Arg | rs1800057 |
| 21 | Cadherin 1, type 1, E-cadherin | CDH1 | Ser270Ala | Not available |
| 22 | Fibroblast growth factor receptor-4 | FGFR4 | Arg388 | rs351855 |
| 23 | Paraoxonase | PON1 | Ile102Val | Not available |
| 24 | Lipoprotein lipase | LPL | Ser447Stop | rs328 |
| 25 | p53 tumor supressor | p53 | Pro72 | rs1042522 |

Figure 1A (cont.)

| | | | | |
|---|---|---|---|---|
| 26 | Epoxide hydrolase 1, microsomal | EPHX | His113 | rs1051740 |
| 27 | ElaC homolog 2 | ELAC2 | Ala541Thr | rs5030739 |
| 28 | ElaC homolog 2 | ELAC2 | Ser217Leu | rs4792311 |
| 29 | Macrophage scavenger receptor 1 | MSR1 | Arg293X | Not available |
| 30 | Estrogen receptor | ER | G-C codon 325 | rs1801132 |
| 31 | Cytochrome P450, family 1, subfamily A, pp1 | CYP1A1 | A1334G, Ile462Val | rs1048943 |
| 32 | Transmembrane serine protease 2 | TMPRSS2 | Met160Val | rs12329760 |
| 33 | Androgen receptor | AR | A639G | rs6152 |
| 34 | RNAse L | RNASEL | A1385G | rs486907 |
| 35 | RNase L | RNASEL | G1623T | Not available |
| 36 | RNAse L | RNASEL | G3T | Not available |
| 37 | B-cell CLL/lymphoma 2, transcript variant 1 | BCL2 | C938A | rs2279115 |
| 38 | Interleukin 10 | IL10 | A-1082G | rs1800896 |
| 39 | Cadherin 1 | CDH1 | C-160A | rs16260 |
| 40 | Cytochrome P450, family 7, subfamily B, pp1 | CYP7B1 | C-104G | Not available |
| 41 | Insulin gene | INS | C1127T | rs3842752 |
| 42 | Cyclin D1 parathyroid adenomatosis 1 | CDC1 | G8070A | rs603965 |
| 43 | Collagen alpha1 type XVIII (endostatin) | COL18 | Asp104Asn | Not available |
| 44 | TGFbeta1 | TGFB1 | C-T codon 10 | rs1982073 |
| 45 | TGFbeta1 | TGFB1 | C-509T | rs17251290 |
| 46 | Leptin | LEPTIN | G2548A | rs7799039 |
| 47 | Cyclin dependant kinase 1B | CDKN1B | Val109 | rs2066827 |
| 48 | Cyclin dependant kinase 1A | CDKN1A | C17197 | rs1059234 |
| 49 | Insulin-like growth factor-binding protein3 | IGFBP3 | A-202C | rs2854744 |
| 50 | Prostate specific antigen | PSA | A-158G | rs266882 |
| 51 | Prostate specific antigen | PSA | A-4643G | rs925013 |

Figure 1A (cont.)

| # | Description | Gene | Variant | rs |
|---|---|---|---|---|
| 52 | Prostate specific antigen | PSA | C-5412T | rs2739448 |
| 53 | Prostate specific antigen | PSA | T-5429G | rs3269733 |
| 54 | Vascular endothelial growth factor | VEGF | C-460T | rs833061 |
| 55 | CHK2 checkpoint homolog (isoform 1) | CHEK2 | G1V52+1A | Not available |
| 56 | Cytochrome P450, family 1, subfamily A, pp1 | CYP1A1 | C3798T | rs4646903 |
| 57 | Interleukin 8 | IL8 | A251T | rs4073 |
| 58 | Osteocalcin | BGLAP | C-198T | rs1800247 |
| 59 | Androgen receptor | AR | Arg726Leu | Not available |
| 60 | Cytochrome P450, subfamily 17 | CYP17A1 | T-34C | rs743572 |
| 61 | Cytochrome P450, family 1, subfamily B, pp1 | CYP1B1 | C1001T | rs2567206 |
| 62 | Cytochrome P450, family 1, subfamily B, pp1 | CYP1B1 | A-263G | rs2551188 |
| 63 | Cytochrome P450, family 1, subfamily B, pp1 | CYP1B1 | C-13T | rs2617266 |
| 64 | Cytochrome P450, family 1, subfamily B, pp1 | CYP1B1 | C142G | rs10012 |
| 65 | Cytochrome P450, family 1, subfamily B, pp1 | CYP1B1 | G355T | rs1056827 |
| 66 | Cytochrome P450, family 3, subfamily A, pp4 | CYP3A4 | A290G | rs2740574 |
| 67 | Cytochrome P450, family 19 | CYP19 | C79CT | rs700519 |
| 68 | Glutathione S-transferase M3 | GSTM3 | G2654A | rs1799735 |
| 69 | Human sulfotransferase 1A1 | SULT1A1 | A2563G | rs9282861 |
| 70 | Vitamin D Receptor | VDR | T2C, MetThr | rs10735810 |
| 71 | Vitamin D Receptor | VDR | T-C codon 325 | rs731236 |
| 72 | Methylenetetrahydrofolate reductase | MTHFR | C677T, Ala Val | rs1801133 |
| 73 | Methylenetetrahydrofolate reductase | MTHFR | A1298C, Glu Ala | rs1801131 |
| 74 | Toll-like receptor 4 | TLR4 | C1381G | rs11536889 |
| 75 | Cytochrome P450, family 2, subfamily C, p19 | CYP2C19 | A681G | rs4244285 |
| 76 | Cytochrome P450, family 2, subfamily C, p19 | CYP2C19 | A636G | rs4986893 |
| 77 | Cytochrome P450, family 2, subfamily C, p19 | CYP2C19 | A1G, Met | Not available |

Figure 1A (cont.)

| | | | | |
|---|---|---|---|---|
| 78 | N-acetyltransferase-2 | NAT2 | C481T, Leu161Leu | rs1799929 |
| 79 | N-acetyltransferase-2 | NAT2 | C341T, Ile114Thr | rs1801280 |
| 80 | N-acetyltransferase-2 | NAT2 | C282T, Tyr94Tyr | rs1041983 |
| 81 | N-acetyltransferase-2 | NAT2 | A590G, Arg197Arg | rs1799930 |
| 82 | N-acetyltransferase-2 | NAT2 | A857G, Gly286Glu | rs1799931 |
| 83 | Breast Cancer 2 | BRCA2 | T1616G (deletion) | Not available |
| 84 | CHK2 checkpoint homolog (isoform 1) | CHEK2 | C1100T (deletion) | Not available |
| 85 | Hypoxia-inducible factor 1 alpha t. variant 1 | HIF1A1 | Pro582Ser | rs11549465 |
| 86 | Androgen receptor | AR | Ser296Arg | Not available |
| 87 | Androgen receptor | AR | Glu796Glu | Not available |
| 88 | Androgen receptor | AR | Asp890Asn | Not available |
| 89 | Androgen receptor | AR | C→A codon 214 | Not available |
| 90 | Interleukin 6 | IL6 | G-174C | rs1800795 |

Figure 1B: Table 1B

| SNP code | Gene name | Gene symbol | SNP | rs ID | Genotype 0 | Genotype 1 | Genotype 2 |
|---|---|---|---|---|---|---|---|
| 9 | Kallikrein-2 | KLK2 | Arg250Trp | rs198977 | CC | CT | TT |
| 24 | Lipoprotein lipase | LPL | Ser447Stop | rs328 | CC | CG | GG |
| 25 | P53 tumour suppressor | p53 | Pro72 | rs1042522 | GG | GC | CC |
| 28 | ElaC homolog 2 | ELAC2 | Ser217Leu | rs4792311 | GG | GA | AA |
| 31 | Cytochrome P450, family 1, subfamily A, pp1 | CYP1A1 | A1384G, Ile462Val | rs1048943 | AA | AG | GG |
| 32 | Transmembrane serine protease 2 | TMPRSS2 | Met160Val | rs12329760 | CC | CT | TT |
| 34 | RNAse L | RNASEL | A1385G | rs486907 | GG | GA | AA |
| 46 | Leptin | LEPTIN | G2548A | rs7799039 | AA | AG | GG |
| 47 | Cyclin dependent kinase 1B | CDKN1B | Val109 | rs2066827 | TT | TG | GG |
| 51 | Prostate specific antigen | PSA | A-4643G | rs925013 | AA | AG | GG |
| 56 | Cytochrome P450, family 1, subfamily A, pp1 | CYP1A1 | C3798T | rs4646903 | CC | CT | CT |
| 58 | Osteocalcin | BGLAP | C-198T | rs1800247 | TT | TC | CC |
| 80 | N-acetyltransferase-2 | NAT2 | C282T, Tyr94Tyr | rs1041983 | CC | CT | TT |

Figure 2: Table 2

| SNP# | Gene Symbol | Oligonucleotide sequence (5' > 3') | SEQ ID NO: |
|---|---|---|---|
| 1 | BCL2 | GCTGGGAGAACAGGGTACGATAA | 1 |
| | | GCTGGGAGAACGGGGTACGATAA | 2 |
| | | TTATCGTACCCTGTTCTCCCAGC | 3 |
| | | TTATCGTACCCCGTTCTCCCAGC | 4 |
| 2 | CDK11B | GGGTTCGGGCCGCGTAGGGGC | 5 |
| | | GGGTTCGGGCTGCGTAGGGGC | 6 |
| | | GCCCCTACGCGCCCGAACCC | 7 |
| | | GCCCCTACGCAGCCCGAACCC | 8 |
| 3 | CHEK2 | AAACTCTTACATTGCATACATAG | 9 |
| | | AAACTCTTACACTGCATACATAG | 10 |
| | | AACTCTTACATTGCATACATA | 11 |
| | | AACTCTTACACTGCATACATA | 12 |
| 4 | UGT2B15 | ATCTTCCAAATCATTTTTAGTTA | 13 |
| | | ATCTTCCAAATAATTTTTAGTTA | 14 |
| | | TCTTCCAAATCATTTTTAGTT | 15 |
| | | TCTTCCAAATAATTTTTAGTT | 16 |
| 5 | HSD17B3 | CCTTCTACAGCGGTGCCTTCCAA | 17 |
| | | CCTTCTACAGCAGTGCCTTCCAA | 18 |
| | | TTGGAAGGCACCGCTGTAGAAGG | 19 |
| | | TTGGAAGGCACTGCTGTAGAAGG | 20 |
| 6 | HSD3B1 | GCACAAGGAGAACCTGAAGTCCA | 21 |
| | | GCACAAGGAGACCCTGAAGTCCA | 22 |
| | | GACTTCAGGTTCTCCTTGT | 23 |
| | | GACTTCAGGGTCTCCTTGT | 24 |
| 7 | HSD3B2 | CCATTTCCCCTCTTAAATGAGAA | 25 |
| | | CCATTTCCCCTGTTAAATGAGAA | 26 |
| | | CATTTCCCCTCTTAAATGAGA | 27 |
| | | CATTTCCCCTGTTAAATGAGA | 28 |
| 8 | KLK10 | AAGCCTATGGCGCCCCGTGCGCG | 29 |
| | | AAGCCTATGGCTCCCCGTGCGCG | 30 |
| | | GCGCACGGGGCGCCATAGGCT | 31 |
| | | GCGCACGGGGAGCCATAGGCT | 32 |
| 9 | KLK2 | GATCCACTTCCGGTAATGCACCA | 33 |
| | | GATCCACTTCCAGTAATGCACCA | 34 |
| | | ATCCACTTCCGGTAATGCACC | 35 |
| | | ATCCACTTCCAGTAATGCACC | 36 |
| 10 | HER2 | ACGTCCATCATCTCTGCGG | 37 |
| | | ACGTCCATCGTCTCTGCGG | 38 |
| | | GACGTCCATCATCTCTGCGGT | 39 |
| | | GACGTCCATCGTCTCTGCGGT | 40 |
| 11 | GSTT1 | TGCCTAGTGGGTTCACCTGCCCA | 41 |
| | | TGCCTAGTGGGGTCACCTGCCCA | 42 |
| | | CTGCCTAGTGGGTTCACCTGCCCAC | 43 |
| | | CTGCCTAGTGGGGTCACCTGCCCAC | 44 |
| 12 | GSTM1 | CACACATTCTTGGCCTTCTGCAGAT | 45 |
| | | CACACATTCTTGACCTTCTGCAGAT | 46 | cont'd...

Figure 2 (cont.)

| | | | |
|---|---|---|---|
| | | ATCTGCAGAAGGCCAAGAATGTGTG | 47 |
| | | ATCTGCAGAAGGTCAAGAATGTGTG | 48 |
| 13 | CYP1B1 | AATCATGACCCACTGAAGTGGCCTA | 49 |
| | | AATCATGACCCAGTGAAGTGGCCTA | 50 |
| | | TAGGCCACTTCAGTGGGTCATGATT | 51 |
| | | TAGGCCACTTCACTGGGTCATGATT | 52 |
| 14 | OGG1 | GAGCATGGCGGCATTGGCGCAGG | 53 |
| | | GAGCATGGCGGGATTGGCGCAGG | 54 |
| | | CCTGCGCCAATGCCGCCATGCTC | 55 |
| | | CCTGCGCCAATCCCGCCATGCTC | 56 |
| 15 | SRD5A2 | GGCGGCGCGGGCTGGCAGGCGGG | 57 |
| | | GGCGGCGCGGGTTGGCAGGCGGG | 58 |
| | | CCGCCTGCCAGCCCGCGCCGC | 59 |
| | | CCGCCTGCCAACCCGCGCCGC | 60 |
| 16 | SRD5A2 | CCTCTTCTGCGTACATTACTT | 61 |
| | | CCTCTTCTGCCTACATTACTT | 62 |
| | | GAAGTAATGTACGCAGAAGAGGC | 63 |
| | | GAAGTAATGTAGGCAGAAGAGGC | 64 |
| 17 | NOS3 | CCCCAGATGAGCCCCCAGAAC | 65 |
| | | CCCCAGATGATCCCCCAGAAC | 66 |
| | | AGTTCTGGGGGCTCATCTGGGGC | 67 |
| | | AGTTCTGGGGGATCATCTGGGGC | 68 |
| 18 | TNFA | TGAGGGGCATGGGGACGGGGTTC | 69 |
| | | TGAGGGGCATGAGGACGGGGTTC | 70 |
| | | GAACCCCGTCCCCATGCCCCTCA | 71 |
| | | GAACCCCGTCCTCATGCCCCTCA | 72 |
| 19 | ESR1 | ACCAAAGCATCTGGGATGGCCCT | 73 |
| | | ACCAAAGCATCCGGGATGGCCCT | 74 |
| | | AGGGCCATCCCAGATGCTTTGGT | 75 |
| | | ACCAAAGCATCCGGGATGGCCCT | 76 |
| 20 | ATM | GTAGGCTGATCCTTATTCAAAAT | 77 |
| | | GTAGGCTGATCGTTATTCAAAAT | 78 |
| | | ATTTTGAATAAGGATCAGCCTAC | 79 |
| | | ATTTTGAATAACGATCAGCCTAC | 80 |
| 21 | CDH1 | TCTTTAAGGGGTCTGTCATGGAA | 81 |
| | | TCTTTAAGGGGGCTGTCATGGAA | 82 |
| | | TTCCATGACAGACCCCTTAAAGA | 83 |
| | | TTCCATGACAGCCCCCTTAAAGA | 84 |
| 22 | FGFR4 | TGCTGCTGGCCGGGCTGTATCGA | 85 |
| | | TGCTGCTGGCCAGGCTGTATCGA | 86 |
| | | TCGATACAGCCCGGCCAGCAGCA | 87 |
| | | TCGATACAGCCTGGCCAGCAGCA | 88 |
| 23 | PON1 | TGGAATTGGGGATCACTGGAAGT | 89 |
| | | TGGAATTGGGGGTCACTGGAAGT | 90 |
| | | ACTTCCAGTGATCCCCAATTCCA | 91 |
| | | ACTTCCAGTGACCCCCAATTCCA | 92 |
| 24 | LPL | GAATAAGAAGTCAGGCTGGTGAG | 93 |
| | | GAATAAGAAGTGAGGCTGGTGAG | 94 |
| | | CTCACCAGCCTGACTTCTTATTC | 95 |
| | | CTCACCAGCCTCACTTCTTATTC | 96 | cont'd...

Figure 2 (cont.)

| 25 | p53 | GGCTGCTCCCCGCGTGGCCCCTG | 97 |
|---|---|---|---|
| | | GGCTGCTCCCCCCGTGGCCCCTG | 98 |
| | | CAGGGGCCACGCGGGGAGCAGCC | 99 |
| | | CAGGGGCCACGGGGGAGCAGCC | 100 |
| 26 | EPHX | TTCTCAACAGATACCCTCACTTC | 101 |
| | | TTCTCAACAGACACCCTCACTTC | 102 |
| | | GAAGTGAGGGTATCTGTTGAGAA | 103 |
| | | GAAGTGAGGGTGTCTGTTGAGAA | 104 |
| 27 | ELAC2 | AGACTCCGAGTTGAATGAAAATG | 105 |
| | | AGACTCCGAGTCGAATGAAAATG | 106 |
| | | CATTTTCATTCAACTCGGAGTCT | 107 |
| | | CATTTTCATTCGACTCGGAGTCT | 108 |
| 28 | ELAC2 | GCACCCTGGCTGCTGTGTTTGTG | 109 |
| | | GCACCCTGGCTACTGTGTTTGTG | 110 |
| | | CACAAACACAGCAGCCAGGGTGC | 111 |
| | | CACAAACACAGTAGCCAGGGTGC | 112 |
| 29 | MSR1 | AAAGTGGTCCACGAGGATTTCCA | 113 |
| | | AAAGTGGTCCATGAGGATTTCCA | 114 |
| | | TGGAAATCCTCGTGGACCACTTT | 115 |
| | | TGGAAATCCTCATGGACCACTTT | 116 |
| 30 | ER | GCTGAGCCCCCGATACTCTATTC | 117 |
| | | GCTGAGCCCCCGATACTCTATTC | 118 |
| | | GAATAGAGTATGGGGGGCTCAGC | 119 |
| | | GAATAGAGTATCGGGGGCTCAGC | 120 |
| 31 | CYP1A1 | TCGGTGAGACCATTGCCCGCTGG | 121 |
| | | TCGGTGAGACCGTTGCCCGCTGG | 122 |
| | | CCAGCGGGCAATGGTCTCACCGA | 123 |
| | | CCAGCGGGCAACGGTCTCACCGA | 124 |
| 32 | TMPRSS2 | CATCCTTCAGATGTACTCATC | 125 |
| | | CATCCTTCAGGTGTACTCATC | 126 |
| | | GATGAGTACATCTGAAGGATG | 127 |
| | | GATGAGTACACCTGAAGGATG | 128 |
| 33 | AR | AGAGCGAGGGAAGCCTCGGGGGC | 129 |
| | | AGAGCGAGGGGAGCCTCGGGGGC | 130 |
| | | GCCCCCGAGGCTTCCCTCGCTCT | 131 |
| | | GCCCCCGAGGCCTCCCTCGCTCT | 132 |
| 34 | RNASEL | TGAATTTGCCCAAAATGTCCTGT | 133 |
| | | TGAATTTGCCCGAAATGTCCTGT | 134 |
| | | ACAGGACATTTTGGGCAAATTCA | 135 |
| | | ACAGGACATTTCGGGCAAATTCA | 136 |
| 35 | RNASEL | TCATTTGAGGAGCTGAAAGCTCA | 137 |
| | | TCATTTGAGGATCTGAAAGCTCA | 138 |
| | | TGAGCTTTCAGCTCCTCAAATGA | 139 |
| | | TGAGCTTTCAGATCCTCAAATGA | 140 |
| 36 | RNASEL | AAGAGCACATAGAGATTAATGAC | 141 |
| | | AAGAGCACATATAGATTAATGAC | 142 |
| | | GTCATTAATCTCTATGTGCTCTT | 143 |
| | | GTCATTAATCTATATGTGCTCTT | 144 |
| 37 | BCL2 | TTCATCGTCCCCTCTCCCCTGTC | 145 |
| | | TTCATCGTCCCATCTCCCCTGTC | 146 | cont'd...

Figure 2 (cont.)

| | | | |
|---|---|---|---|
| | | GACAGGGGAGAGGGGACGATGAA | 147 |
| | | GACAGGGGAGATGGGACGATGAA | 148 |
| 38 | IL10 | GCTTCTTTGGGAAGGGGAAGTAGGG | 149 |
| | | CCCTACTTCCCCTTCCCAAAGAAGC | 150 |
| | | GCTTCTTTGGGAGGGGGAAGTACGG | 151 |
| | | CCCTACTTCCCCCTCCCAAAGAAGC | 152 |
| 39 | CD81 | CTAGAGGGTCACCGCGTCTATGC | 153 |
| | | CTAGAGGCTCAACGCGTCTATGC | 154 |
| | | GCATAGACGCGGTGACCCTCTAG | 155 |
| | | GCATAGACGCGTTGACCCTCTAG | 156 |
| 40 | CYP7B1 | GAAGGGCCAAGGAAGGGGTTAGA | 157 |
| | | GAAGGGCCAAGCAAGGGGTTAGA | 158 |
| | | CTAACCCCTTCCTTGGCCCTT | 159 |
| | | CTAACCCCTTGCTTGGCCCTT | 160 |
| 41 | INS | TAGACGCAGCCCGCAGGCAGCCC | 161 |
| | | TAGACGCAGCCTGCAGGCAGCCC | 162 |
| | | GGGCTGCCTGCGGGCTGCGTCTA | 163 |
| | | GGGCTGCCTGCAGGCTGCGTCTA | 164 |
| 42 | CDC1 | CCCTCACTTACCGGGTCACACTT | 165 |
| | | CCCTCACTTACTGGGTCACACTT | 166 |
| | | CCTCACTTACCGGGTCACACT | 167 |
| | | CCTCACTTACTGGGTCACACT | 168 |
| 43 | COL18 | TCTTCTCCTTTAACGGCAAGGAC | 169 |
| | | TCTTCTCCTTTGACGGCAAGGAC | 170 |
| | | GTCCTTGCCGTTAAAGGAGAAGA | 171 |
| | | GTCCTTGCCGTCAAAGGAGAAGA | 172 |
| 44 | TGFB1 | GCGGCTGCTGCCGCTGCTGCTAC | 173 |
| | | GCGGCTGCTGCTGCTGCTGCTAC | 174 |
| | | GTAGCAGCAGCGGCAGCAGCCGC | 175 |
| | | GTAGCAGCAGCAGCAGCAGCCGC | 176 |
| 45 | TGFB1 | CCCTTCCATCCCTCAGGTGTCCT | 177 |
| | | CCCTTCCATCCTTCAGGTGTCCT | 178 |
| | | CCTTCCATCCCTCAGGTGTCC | 179 |
| | | CCTTCCATCCTTCAGGTGTCC | 180 |
| 46 | LEPTIN | GACAGGGTTGCGCTGATCCTCCC | 181 |
| | | GACAGGGTTGCACTGATCCTCCC | 182 |
| | | GGGAGGATCAGCGCAACCCTGTC | 183 |
| | | GGGAGGATCAGTGCAACCCTGTC | 184 |
| 47 | CDKN1B | GGCTCCCGCTGCCATCCTGGCTC | 185 |
| | | GGCTCCCGCTGACATCCTGGCTC | 186 |
| | | GCTCCCGCTGCCATCCTGGCT | 187 |
| | | GCTCCCGCTGACATCCTGGCT | 188 |
| 48 | CDKN1A | CAGGAAGCCTGCAGTCCTGGAAG | 189 |
| | | CAGGAAGCCTGTAGTCCTGGAAG | 190 |
| | | CTTCCAGGACTGCAGGCTTCCTG | 191 |
| | | CTTCCAGGACTACAGGCTTCCTG | 192 |
| 49 | IGFBP3 | CTCCGGGCGTGAGCACGAGGAGC | 193 |
| | | CTCCGGGCGTGCGCACGAGGAGC | 194 |
| | | GCTCCTCGTGCTCACGCCCGGAG | 195 |
| | | GCTCCTCGTGCGCACGCCCGGAG | 196 | cont'd...

Figure 2 (cont.)

| | | | |
|---|---|---|---|
| 50 | PSA | AACAGCAAGTACTAGCTCTCC | 197 |
| | | AACAGCAAGTGCTAGCTCTCC | 198 |
| | | GGAGAGCTAGTACTTGCTGTT | 199 |
| | | GGAGAGCTAGCACTTGCTGTT | 200 |
| 51 | PSA | CCTCCACCATGATACTAGGACCC | 201 |
| | | CCTCCACCATGGTACTAGGACCC | 202 |
| | | CTCCACCATGATACTAGGACC | 203 |
| | | CTCCACCATGGTACTAGGACC | 204 |
| 52 | PSA | GCGTGAGCCACCGCGCCTGGCCG | 205 |
| | | GCGTGAGCCACTGCGCCTGGCCG | 206 |
| | | CGTGAGCCACCGCGCCTGGCC | 207 |
| | | CGTGAGCCACTGCGCCTGGCC | 208 |
| 53 | PSA | GTGCTGGGATTACAGGCGTGA | 209 |
| | | GTGCTGGGATGACAGGCGTGA | 210 |
| | | CACGCCTGTAATCCCAGCA | 211 |
| | | CACGCCTGTCATCCCAGCA | 212 |
| 54 | VEGF | CCGCTCCAACGCCCTCAACCC | 213 |
| | | CCGCTCCAACACCCTCAACCC | 214 |
| | | CGCTCCAACGCCCTCAACC | 215 |
| | | CGCTCCAACACCCTCAACC | 216 |
| 55 | CHEK2 | GGATTTTCAGGGTAGGTAATGAA | 217 |
| | | GGATTTTCAGGATAGGTAATGAA | 218 |
| | | TTCATTACCTACCCTGAAAATCC | 219 |
| | | TTCATTACCTATCCTGAAAATCC | 220 |
| 56 | CYP1A1 | GTGTGAGCCCGGGAGGTGGAG | 221 |
| | | GTGTGAGCCCAGGAGGTGGAG | 222 |
| | | TGTGAGCCCGGGAGGTGGA | 223 |
| | | TGTGAGCCCAGGAGGTGGA | 224 |
| 57 | IL8 | AAAAGCATACAATTGATAATTCA | 225 |
| | | AAAAGCATACATTTGATAATTCA | 226 |
| | | TGAATTATCAATTGTATGCTTTT | 227 |
| | | TGAATTATCAAATGTATGCTTTT | 228 |
| 58 | BGLAP | CACAATATCCTCTGGGGTTTGGC | 229 |
| | | CACAATATCCTTTGGGGTTTGGC | 230 |
| | | GCCAAACCCCAGAGGATATTGTG | 231 |
| | | GCCAAACCCCAAAGGATATTGTG | 232 |
| 59 | AR | TCCAGGCTTCCGCAACTTACACG | 233 |
| | | TCCAGGCTTCCTCAACTTACACG | 234 |
| | | CGTGTAAGTTGCGGAAGCCTGGA | 235 |
| | | CGTGTAAGTTGAGGAAGCCTGGA | 236 |
| 60 | MSPA1 | TCTACTCCACTGCTGTCTATC | 237 |
| | | TCTACTCCACCGCTGTCTATC | 238 |
| | | GATAGACAGCGGTGGAGTAGA | 239 |
| | | GATAGACAGCAGTGGAGTAGA | 240 |
| 61 | CYP1B1 | CGTGCGGCCTCGATTGGAGGT | 241 |
| | | CGTGCGGCCTTGATTGGAGGT | 242 |
| | | GTGCGGCCTCGATTGGAGG | 243 |
| | | GTGCGGCCTTGATTGGAGG | 244 |
| 62 | CYP1B1 | CGTTGTCCCCAAATTGCAGGAAC | 245 |
| | | CGTTGTCCCCAGATTGCAGGAAC | 246 | cont'd...

Figure 2 (cont.)

| | | | |
|---|---|---|---|
| | | GTTCCTGCAATTTCGGGACAACG | 247 |
| | | GTTCCTGCAATCTGGGGACAACG | 248 |
| 63 | CYP1B1 | GCCTTCTCCTCTCTGTCCCCA | 249 |
| | | GCCTTCTCCTTTCTGTCCCCA | 250 |
| | | CCTTCTCCTCTCTGTCCCC | 251 |
| | | CCTTCTCCTTTCTGTCCCC | 252 |
| 64 | CYP1B1 | GGCGGCAGCTCCGGTCCGCGCCC | 253 |
| | | GGCGGCAGCTCGGGTCCCCGCCC | 254 |
| | | GGGCGCGGACCGGAGCTGCCGCC | 255 |
| | | GGGCGCGGACCCGAGCTGCCGCC | 256 |
| 65 | CYP1B1 | CCGACCGGCCGGCCTTCGCCTCC | 257 |
| | | CCGACCGGCCGTCCTTCGCCTCC | 258 |
| | | GGAGGCGAAGGCCGGCCGGTCGG | 259 |
| | | GGAGGCGAAGGACGGCCGGTCGG | 260 |
| 66 | CYP3A4 | CGCCTCTCTCTTGCCCTTGTC | 261 |
| | | CGCCTCTCTCCTGCCCTTGTC | 262 |
| | | GCCTCTCTCTTGCCCTTGT | 263 |
| | | GCCTCTCTCCTGCCCTTGT | 264 |
| 67 | CYP19 | CAGAAAAAGACGCAGGATTTCC | 265 |
| | | CAGAAAAAGATGCAGGATTTCC | 266 |
| | | GGAAATCCTGCGTCTTTTTTCTG | 267 |
| | | GGAAATCCTGCATCTTTTTTCTG | 268 |
| 68 | GSTM3 | AGGGAAAAGAAGAGGATACTTCT | 269 |
| | | AGGGAAAAGAAAGGATACTTCTC | 270 |
| | | AGAAGTATCCTCTTCTTTTCCCT | 271 |
| | | CAGAAGTATCCTTTCTTTTCCCT | 272 |
| 69 | SULT1A1 | GTTTCTGGGGCACTCCCTGCCAG | 273 |
| | | GTTTGTGGGGCGCTCCCTGCCAG | 274 |
| | | TGGCAGGGAGTGCCCCACAAA | 274 |
| | | TGGCAGGGAGCGCCCCACAAA | 276 |
| 70 | VDR | TCTTACAGGGATGGAGGCAATGG | 277 |
| | | TCTTACAGGGACGGAGGCAATGG | 278 |
| | | CCATTGCCTCCATCCCTGTAAGA | 279 |
| | | CCATTGCCTCCGTCCCTGTAAGA | 280 |
| 71 | VDR | GCCGCGCTGATTGAGGCCATCCA | 281 |
| | | GCCGCGCTGATCGAGGCCATCCA | 282 |
| | | CCGCGCTGATTGAGGCCATCC | 283 |
| | | CCGCGCTGATCGAGGCCATCC | 284 |
| 72 | MTHFR | TCTGCGGGAGCCGATTTCATC | 285 |
| | | TCTGCGGGAGTCGATTTCATC | 286 |
| | | GATGAAATCGGCTCCCGCAGA | 287 |
| | | GATGAAATCGACTCCCGCAGA | 288 |
| 73 | MTHFR | GACCAGTGAAGAAAGTGTCTTTG | 289 |
| | | GACCAGTGAAGCAAGTGTCTTTG | 290 |
| | | AAAGACACTTTCTTCACTGGT | 291 |
| | | AAAGACACTTGCTTCACTGGT | 292 |
| 74 | TLR4 | CATTTGGGAACAGTGGATGTTA | 293 |
| | | CATTTGGGAAGAGTGGATGTTA | 294 |
| | | TAACATCCACTGTTCCCAAAATG | 295 |
| | | TAACATCCACTCTTCCCAAAATG | 296 | cont'd...

Figure 2 (cont.)

| | | | |
|---|---|---|---|
| 75 | CYP2C19 | GATTATTTCCCAGGAACCCATAA | 297 |
| | | GATTATTTCCCGGGAACCCATAA | 298 |
| | | ATTATTTCCCAGGAACCCATA | 299 |
| | | ATTATTTCCCGGGAACCCATA | 300 |
| 76 | CYP2C19 | AGCACCCCTGAATCCAGGTAAG | 301 |
| | | AGCACCCCTGGATCCAGGTAAG | 302 |
| | | CTTACCTGGATTCAGGGGTGCT | 303 |
| | | CTTACCTGGATCCAGGGGTGCT | 304 |
| 77 | CYP2C19 | GAAGGCTTCAATGGATCCTTT | 305 |
| | | GAAGGCTTCAGTGGATCCTTT | 306 |
| | | AAAGGATCCATTGAAGCCTTC | 307 |
| | | AAAGGATCCACTGAAGCCTTC | 308 |
| 78 | NAT2 | GAATCTGGTACCTGGACCAAATC | 309 |
| | | GAATCTGGTACTTGGACCAAATC | 310 |
| | | AATCTGGTACCTGGACCAAAT | 311 |
| | | AATCTGGTACTTGGACCAAAT | 312 |
| 79 | NAT2 | CCTGCCGTCAGTGGTCACCTG | 313 |
| | | CCTGCCGTCAATGGTCACCTG | 314 |
| | | CTGCCGTCAGTGGTCACCT | 315 |
| | | CTGCCGTCAATGGTCACCT | 316 |
| 80 | NAT2 | GGGTATTTTTACATCCCTCCAGT | 317 |
| | | GGGTATTTTTATATCCCTCCAGT | 318 |
| | | GGTATTTTTACATCCCTCCAG | 319 |
| | | GGTATTTTTATATCCCTCCAG | 320 |
| 81 | NAT2 | GCTTGAACCTCAAACAATTGAAG | 321 |
| | | GCTTGAACCTCGAACAATTGAAG | 322 |
| | | CTTCAATTGTTTGAGGTTCAAGC | 323 |
| | | CTTCAATTGTTCGAGGTTCAAGC | 324 |
| 82 | NAT2 | ACCTGGTGATGAATCCCTTACTA | 325 |
| | | ACCTGGTGATGGATCCCTTACTA | 326 |
| | | TAGTAAGGGATTCATCACCAGGT | 327 |
| | | TAGTAAGGGATCCATCACCAGGT | 328 |
| 83 | BRCA2 | AGCACAGCAAGTGGAAAATCTGT | 329 |
| | | AGCACAGCAAGGGAAAATCTGT | 330 |
| | | ACAGATTTTCCACTTGCTGTGCT | 331 |
| | | GACAGATTTTCCCTTGCTGTGCT | 332 |
| 84 | CHEK2 | ATTTTAGATTACTGATTTTGCGC | 333 |
| | | ATTTTAGATTATGATTTTGGGCA | 334 |
| | | GCCCAAAATCAGTAATCTAAAAT | 335 |
| | | TGCCCAAAATCATAATCTAAAAT | 336 |
| 85 | HIF1A1 | GCTTTCTAATGGTGACAACTGAT | 337 |
| | | GCTTTCTAATGATGACAACTGAT | 338 |
| | | CTTTCTAATGGTGACAACTGA | 339 |
| | | CTTTCTAATGATGACAACTGA | 340 |
| 86 | AR | TAGACGACAGCGCAGGCAAGA | 341 |
| | | TAGACGACAGAGCAGGCAAGA | 342 |
| | | TCTTGCCTGCGCTGTCGTCTA | 343 |
| | | TCTTGCCTGCTCTGTCGTCTA | 344 |
| 87 | AR | TTGGATGGCTCCAAATCACCCCC | 345 |
| | | TTGGATGGCTCGAAATCACCCCC | 346 | cont'd...

Figure 2 (cont.)

| | | | |
|---|---|---|---|
| | | GGGGGTGATTTGGAGCCATCCAA | 347 |
| | | GGGGGTGATTTCGAGCCATCCAA | 348 |
| 88 | AR | TGGTGAGCGTGGACTTTCCGGAA | 349 |
| | | TGGTGAGCGTGAACTTTCCGGAA | 350 |
| | | TTCCGGAAAGTCCACGCTCACCA | 351 |
| | | TTCCGGAAAGTTCACGCTCACCA | 352 |
| 89 | AR | GCCCGGAGCTGCCCTTTCCTCTT | 353 |
| | | GCCCGGAGCTGACCTTTCCTCTT | 354 |
| | | AAGAGGAAAGGGCAGCTCCGGGC | 355 |
| | | AAGAGGAAAGGTCAGCTCCGGGC | 356 |
| 90 | IL6 | TTGTGTCTTGCGATGCTAAAGGA | 357 |
| | | TTGTGTCTTGCCATGCTAAAGGA | 358 |
| | | TCCTTTAGCATCGCAAGACACAA | 359 |
| | | TCCTTTAGCATGGCAAGACACAA | 360 |

Figure 3A: Table 3A

| SNP | Gene | Forward Primers (sequence 5' > 3') | SEQ ID NO: |
|---|---|---|---|
| 1 | BCL2 | TAATACGACTCACTATAGGGAGAGTTCCTTTCCTCTGGGAAG | 361 |
| 2 | CDKN1B | TAATACGACTCACTATAGGGAGACCATTTGATCAGCCGACACT | 362 |
| 3 | CHEK2 | TAATACGACTCACTATAGGGAGAACCCATCTATCTACCAGACGTG | 363 |
| 4 | UGT2B15 | TAATACGACTCACTATAGGGAGAGACGGGTCATGAGCTGACTG | 364 |
| 5 | HSD17B3 | TAATACGACTCACTATAGGGAGAATGTTATTCCTTCCTCGGGAAC | 365 |
| 6 | HSD3B1 | TAATACGACTCACTATAGGGAGACACGCGAGATCTGGCCTATAA | 366 |
| 7 | HSD3B2 | TAATACGACTCACTATAGGGAGATGTCTTACTAAATCTCAGTGG | 367 |
| 8 | KLK10 | TAATACGACTCACTATAGGGAGACATTCCGTCCCTTTCTTTC | 368 |
| 9 | KLK2 | TAATACGACTCACTATAGGGAGAGGGGTCCACTTGTCTGTAA | 369 |
| 10 | HEP2 | TAATACGACTCACTATAGGGAGACAGCCAAGCCACGTTTTACG | 370 |
| 11 | GSTT1 | TAATACGACTCACTATAGGGAGAGGCAGCATAAGCAGGACTTC | 371 |
| 12 | GSTM1 | TAATACGACTCACTATAGGGAGAATGCTTGCAGGAAACAAGC | 372 |
| 13 | CYP1B1 | TAATACGACTCACTATAGGGAGAACCTCTCTCTGGGCTACCA | 373 |
| 14 | OGG1 | TAATACGACTCACTATAGGGAGACACTCTTCCACCTCCCAACA | 374 |
| 15-16 | SRD5A2 | TAATACGACTCACTATAGGGAGACAACCACAGGGACAGCCTGA | 375 |
| 17 | SOD3 | TAATACGACTCACTATAGGGAGAGAACGCAGGGAGACAGTGGAT | 376 |
| 18 | TNFA | TAATACGACTCACTATAGGGAGAACCTGGTCCCAAAAGAAAT | 377 |
| 19 | ESR1 | TAATACGACTCACTATAGGGAGAGCTGTGCTCTTTTTCCAGCT | 378 |
| 20 | ATM | TAATACGACTCACTATAGGGAGACATGCTTGAGTTGAGTTTTGC | 379 |
| 21 | CDH1 | TAATACGACTCACTATAGGGAGACAATGACAACAAGCCCTAAT | 380 |
| 22 | FGFR4 | TAATACGACTCACTATAGGGAGACGGACATCATCCTGTACGC | 381 |
| 23 | PON1 | TAATACGACTCACTATAGGGAGAAAAGAGCTTCAACCCCAACA | 382 |
| 24 | LPL | TAATACGACTCACTATAGGGAGACTTCCACAGGGTGATCTTCTG | 383 |
| 25 | p53 | TAATACGACTCACTATAGGGAGAGAAGACCCAGGTCCAGATGA | 384 |
| 26 | EPHX | TAATACGACTCACTATAGGGAGAGCTGCTCCACTATGGCTTC | 385 |
| 27 | ELAC2 | TAATACGACTCACTATAGGGAGAAACAGAGCAGGCGGAAAGCA | 386 |
| 28 | ELAC2 | TAATACGACTCACTATAGGGAGACCGACAGCTCTGCCTACTG | 387 |
| 29 | MSR1 | TAATACGACTCACTATAGGGAGAAAGCAGATCGAGGTCCCACT | 388 |
| 30 | EH | TAATACGACTCACTATAGGGAGAAAGAACAGCCCTGGCCTTGT | 389 |
| 31 | CYP1A1 | TAATACGACTCACTATAGGGAGAGTCAACCATCTGAGTTCC | 390 |
| 32 | TMPRSS2 | TAATACGACTCACTATAGGGAGATAATCCTCCCTCTCCTGCAC | 391 |
| 33 | AR | TAATACGACTCACTATAGGGAGATGCTGCCTTGACCTTAAAGA | 392 |
| 34 | RNASEL | TAATACGACTCACTATAGGGAGAGGCTACTTGTTTGTGTGTGT | 393 |
| 35 | RNASEL | TAATACGACTCACTATAGGGAGACCCACTCCTTCCAGGGTTA | 394 |
| 36 | RNASEL | TAATACGACTCACTATAGGGAGAGAGGGAGAAAGAGGGAACA | 395 |
| 37 | BCL2 | TAATACGACTCACTATAGGGAGAGCATTTGCTGTTCCGACTTT | 396 |
| 38 | IL10 | TAATACGACTCACTATAGGGAGATACACACACACAAAATCCAAG | 397 |
| 39 | CDH1 | TAATACGACTCACTATAGGGAGACCCTTTCTGATCCCAGTGT | 398 |
| 40 | CYP7B1 | TAATACGACTCACTATAGGGAGAGCTGGTTCTTGGGAAATCCT | 399 |
| 41 | INS | TAATACGACTCACTATAGGGAGACAGCATCTGCTCCCTCTACC | 400 |
| 42 | COC1 | TAATACGACTCACTATAGGGAGACTCAGGAGCTCCAACAACT | 401 |
| 43 | COL13 | TAATACGACTCACTATAGGGAGACACGGTTTCTTCTAGGAG | 402 |
| 44 | TGFB1 | TAATACGACTCACTATAGGGAGACGACGCCCTCCTACCTTTT | 403 |
| 45 | TGFB1 | TAATACGACTCACTATAGGGAGACAGGGTGTTGAGTGACAGGA | 404 |
| 46 | LEPTIN | TAATACGACTCACTATAGGGAGATTTTGTTGACACAATTCAAACTT | 405 |
| 47 | CORN1B | TAATACGACTCACTATAGGGAGACAGCTTGCCCGAGTTCTACT | 406 |

Figure 3A (cont.)

| | | | |
|---|---|---|---|
| 48 | CDKN1A | TAATACGACTCACTATAGGGAGACCAAGAGCAAGCGCTAATCC | 407 |
| 49 | IGFBP3 | TAATACGACTCACTATAGGGAGACACCTTGCTTCTTGTAGACGAC | 408 |
| 50 | PSA | TAATACGACTCACTATAGGGAGACTGCCTTGTCCCCTACATG | 409 |
| 51 | PSA | TAATACGACTCACTATAGGGAGAGACCATGACCACTCACCA | 410 |
| 52 | PSA | TAATACGACTCACTATAGGGAGAGCCAGGATGGTCTCAGTCTC | 411 |
| 53 | PSA | TAATACGACTCACTATAGGGAGAGCCAGGATGGTCTCAGTCTC | 412 |
| 54 | VEGF | TAATACGACTCACTATAGGGAGATTCGAGACTCAGGACCTTC | 413 |
| 55 | CHEK2 | TAATACGACTCACTATAGGGAGACTACTGGTTTGGGAGGACA | 414 |
| 56 | CYP1A1 | TAATACGACTCACTATAGGGAGAACCAGTCTGTTCTGAGGACA | 415 |
| 57 | IL8 | TAATACGACTCACTATAGGGAGATGCCATTAAAGAAAATCATCCA | 416 |
| 58 | BGLAP | TAATACGACTCACTATAGGGAGACCCCTAGAGCTCAGCCAGT | 417 |
| 59 | AR | TAATACGACTCACTATAGGGAGACAGACTTAGCTCAACCCGTCA | 418 |
| 60 | MSPA1 | TAATACGACTCACTATAGGGAGAGCTCCAGCAGAATCTTTCCA | 419 |
| 61 | CYP1B1 | TAATACGACTCACTATAGGGAGACAAACCCCTGCCACTACATT | 420 |
| 62 | CYP1B1 | TAATACGACTCACTATAGGGAGAGCGACCTTCTTCAGATGGATT | 421 |
| 63 | CYP1B1 | TAATACGACTCACTATAGGGAGAACAGTCACCTCCGACCTCT | 422 |
| 64 | CYP1B1 | TAATACGACTCACTATAGGGAGACCCTTGGCCGGTAAAC | 423 |
| 65 | CYP1B1 | TAATACGACTCACTATAGGGAGACCATACTGGTGCTTGAATGC | 424 |
| 66 | CYP3A4 | TAATACGACTCACTATAGGGAGATTGGAATGAGGAGAGCCATA | 425 |
| 67 | CYP19 | TAATACGACTCACTATAGGGAGACAGCAAGGATTTGAAAGATGC | 426 |
| 68 | GSTM3 | TAATACGACTCACTATAGGGAGACTCCATGTTTCTGGGGAAAT | 427 |
| 69 | SULT1A1 | TAATACGACTCACTATAGGGAGAGTAATCCAGCCTTCCACTGA | 428 |
| 70 | VDR | TAATACGACTCACTATAGGGAGACTGAGCTCCCTGGTCGTG | 429 |
| 71 | VDR | TAATACGACTCACTATAGGGAGACTCAGAGCTCCTGTGCCCTC | 430 |
| 72 | MTHFR | TAATACGACTCACTATAGGGAGACTCTCTGTCCAGTCCCTGT | 431 |
| 73 | MTHFR | TAATACGACTCACTATAGGGAGACCCTCTGTCAGGAGTGTGC | 432 |
| 74 | TLR4 | TAATACGACTCACTATAGGGAGAAAGGTATTCAAGGCAGGCACTA | 433 |
| 75 | CYP2C19 | TAATACGACTCACTATAGGGAGAAATTACAACCAGAGCTTGGCATA | 434 |
| 76 | CYP2C19 | TAATACGACTCACTATAGGGAGACCTGTGATCCCACTTTCATC | 435 |
| 77 | CYP2C19 | TAATACGACTCACTATAGGGAGAGCAAGTTCACGTTCTCTTA | 436 |
| 78 | NAT2 | TAATACGACTCACTATAGGGAGAGGCATGGTTCACCTTCTCCT | 437 |
| 79 | NAT2 | TAATACGACTCACTATAGGGAGATGGTGTCTCCAGGTCAATCA | 438 |
| 80 | NAT2 | TAATACGACTCACTATAGGGAGAGGCTGTTCCCTTTGAGAACC | 439 |
| 81 | NAT2 | TAATACGACTCACTATAGGGAGAGCACCAAATCAGGAGAGAGG | 440 |
| 82 | NAT2 | TAATACGACTCACTATAGGGAGAACCCAGAGGGGTTTACTG | 441 |
| 83 | BRCA2 | TAATACGACTCACTATAGGGAGATCACCTTGTGATGTTAGTTTGGA | 442 |
| 84 | CHEK2 | TAATACGACTCACTATAGGGAGATTAATGGTAGGTGTGAATTG | 443 |
| 85 | HIF1A1 | TAATACGACTCACTATAGGGAGAAAGGTGTGGCCATTGTAAAA | 444 |
| 86 | AR | TAATACGACTCACTATAGGGAGAGAGTCCAGGGGAACAGCTTC | 445 |
| 87 | AR | TAATACGACTCACTATAGGGAGAGGTACCGCATGCACAAGTC | 446 |
| 88 | AR | TAATACGACTCACTATAGGGAGACTGCATCAGTTCACTTTTGACC | 447 |
| 89 | AR | TAATACGACTCACTATAGGGAGAGACAGCCAACGCCTCTTG | 448 |
| 90 | IL8 | TAATACGACTCACTATAGGGAGACAAACACATGCCAAAGTGCTG | 449 |

Figure 3B: Table 3B

| SNP | Gene | Reverse Primers (sequence 5'>3') | SEQ ID NO: |
|---|---|---|---|
| 1 | BCL2 | AATTAACCCTCACTAAAGGGAGAGGGCTGGGAGGAGAAGAT | 450 |
| 2 | CDK11B | AATTAACCCTCACTAAAGGGAGACACTGGCAGGTTTGACATCT | 451 |
| 3 | CHEK2 | AATTAACCCTCACTAAAGGGAGAACAAACGTTTCATTCCCACT | 452 |
| 4 | UGT3B15 | AATTAACCCTCACTAAAGGGAGACATAATATTCCAACACAATTCTTG | 453 |
| 5 | HSD17B3 | AATTAACCCTCACTAAAGGGAGAACCTGACCTTGGTGTTGAGC | 454 |
| 6 | HSD3B1 | AATTAACCCTCACTAAAGGGAGACCACATGCACATCTCTGTC | 455 |
| 7 | HSD3B2 | AATTAACCCTCACTAAAGGGAGATGCTCTTTATGTTGAACTGTGTGA | 456 |
| 8 | KLK10 | AATTAACCCTCACTAAAGGGAGAACTCTGGTCCACCAGGACA | 457 |
| 9 | KLK2 | AATTAACCCTCACTAAAGGGAGACCACAACGTGAGGTGGACTT | 458 |
| 10 | HDR2 | AATTAACCCTCACTAAAGGGAGAAACACCNCGACCAGCAGAAT | 459 |
| 11 | GSTT1 | AATTAACCCTCACTAAAGGGAGAGTTGCTGGAGACAAGTTCC | 460 |
| 12 | GSTM1 | AATTAACCCTCACTAAAGGGAGAAAAGCCGCACATCAACTCCT | 461 |
| 13 | CYP1B1 | AATTAACCCTCACTAAAGGGAGATCATCACTCTGCTGGTCAGG | 462 |
| 14 | OGG1 | AATTAACCCTCACTAAAGGGAGATGGCGANTTCTTTGTCCAG | 463 |
| 15-16 | SRD5A2 | AATTAACCCTCACTAAAGGGAGAAGGGCAAAAACGCTACCTGT | 464 |
| 17 | ROS3 | AATTAACCCTCACTAAAGGGAGACAGTCAATCCCTTTGGTGCT | 465 |
| 18 | TNFA | AATTAACCCTCACTAAAGGGAGAAAAGTTGGGACACACAAGC | 466 |
| 19 | ESR1 | AATTAACCCTCACTAAAGGGAGATCGTTCCCTGGACTGATG | 467 |
| 20 | ATM | AATTAACCCTCACTAAAGGGAGACAGGAAAGTCTTTTCCCATTACA | 468 |
| 21 | CDH1 | AATTAACCCTCACTAAAGGGAGATGTCCTAGGAACGATCAGT | 469 |
| 22 | FGFR4 | AATTAACCCTCACTAAAGGGAGAGATGCCCCAGTACCTGT | 470 |
| 23 | PON1 | AATTAACCCTCACTAAAGGGAGAACCAGGAGGTACATGGCATT | 471 |
| 24 | LPL | AATTAACCCTCACTAAAGGGAGACATGAAGCTGCCTGCCTTAG | 472 |
| 25 | p53 | AATTAACCCTCACTAAAGGGAGACTGCCCTGGTAGGTTTTCTG | 473 |
| 26 | EPHX | AATTAACCCTCACTAAAGGGAGACTTCACGTGGATGAAGTGGA | 474 |
| 27 | ELAC2 | AATTAACCCTCACTAAAGGGAGACAAGACTCCCTGACCCCTCT | 475 |
| 28 | ELAC2 | AATTAACCCTCACTAAAGGGAGACTTCCAGGCTCCAGCTTTGT | 476 |
| 29 | MSR1 | AATTAACCCTCACTAAAGGGAGACGCCCTTTTGTCCAGAATT | 477 |
| 30 | EB | AATTAACCCTCACTAAAGGGAGAATGTCAACCAGCTCCCTGTC | 478 |
| 31 | CYP1A1 | AATTAACCCTCACTAAAGGGAGCACCAGTATACCCAGGAAGAGA | 479 |
| 32 | TMPRSS2 | AATTAACCCTCACTAAAGGGAGAGTGCTGCCCTATACTCACT | 480 |
| 33 | AR | AATTAACCCTCACTAAAGGGAGACGTTGTCAGAAATGGTCGAA | 481 |
| 34 | RNASEL | AATTAACCCTCACTAAAGGGAGAGGTGGGTGTATCCACAGGAC | 482 |
| 35 | RNASEL | AATTAACCCTCACTAAAGGGAGATGAGAAAGTTCAACCGGTCT | 483 |
| 36 | RNASEL | AATTAACCCTCACTAAAGGGAGAGAGTTCAACAGCAAGCAGCA | 484 |
| 37 | BCL2 | AATTAACCCTCACTAAAGGGAGACCCTTCTCGGCAATTTACAC | 485 |
| 38 | IL10 | AATTAACCCTCACTAAAGGGAGAANGCTTCTGTGCCTGCAGTC | 486 |
| 39 | CDH1 | AATTAACCCTCACTAAAGGGAGACTGATTGGCTGAGGGTTCAC | 487 |
| 40 | CYP7B1 | AATTAACCCTCACTAAAGGGAGACCAGGCTGAATGACAAAG | 488 |
| 41 | INS | AATTAACCCTCACTAAAGGGAGAAGGGGCTCACAACAGTGC | 489 |
| 42 | CDC1 | AATTAACCCTCACTAAAGGGAGATAGCCCAACCTTGTGTGC | 490 |
| 43 | COL18 | AATTAACCCTCACTAAAGGGAGACTCTCAGAGCTGCTCACACG | 491 |
| 44 | TGFB1 | AATTAACCCTCACTAAAGGGAGACACAGGGCGTCACCACCACTAG | 492 |
| 45 | TGFB1 | AATTAACCCTCACTAAAGGGAGACANGGGCTGGGAAACAAGGTAG | 493 |
| 46 | LEPTIN | AATTAACCCTCACTAAAGGGAGACTCCAGCCGATCTCTCTGTT | 494 |
| 47 | CDK81B | AATTAACCCTCACTAAAGGGAGATGCAGGTCGCTTCCTATT | 495 |

Figure 3B (cont.)

| | | | |
|---|---|---|---|
| 48 | CDKN2A | AATTAACCCTCACTAAAGGGAGAACCTCTGATTCAACTGCCTA | 496 |
| 49 | IGFBP3 | AATTAACCCTCACTAAAGGGAGAGGAACGGGCTCATCCTCA | 497 |
| 50 | PSA | AATTAACCCTCACTAAAGGGAGACCCAGGAGCCCTATAAACC | 498 |
| 51 | PSA | AATTAACCCTCACTAAAGGGAGAGGCCAGCTGGGAATGAGAT | 499 |
| 52 | PSA | AATTAACCCTCACTAAAGGGAGAACGGTGTGATTTGTGTCAA | 500 |
| 53 | PSA | AATTAACCCTCACTAAAGGGAGAAACGGGCTGATTTGTGCTGA | 501 |
| 54 | VEGF | AATTAACCCTCACTAAAGGGAGACGGAGTAGGAAAGTGAGGTT | 502 |
| 55 | CHEK2 | AATTAACCCTCACTAAAGGGAGAAAGAGTTTTAGGACCCACTTCC | 503 |
| 56 | CYP1A1 | AATTAACCCTCACTAAAGGGAGAGAGCTCAGGAGTTTGAGACCA | 504 |
| 57 | IL8 | AATTAACCCTCACTAAAGGGAGAAGGGTAAACCTGAGTCATCA | 505 |
| 58 | SGLAP | AATTAACCCTCACTAAAGGGAGAGAATCTGCCAGGCCTATTTG | 506 |
| 59 | AR | AATTAACCCTCACTAAAGGGAGAGTCTGGCCAAGCTGCTGTAT | 507 |
| 60 | MSPA1 | AATTAACCCTCACTAAAGGGAGATTGGGCCAAAACAAATAAGC | 508 |
| 61 | CYP1B1 | AATTAACCCTCACTAAAGGGAGAACCGTTGCCATTCTGCCGTA | 509 |
| 62 | CYP1B1 | AATTAACCCTCACTAAAGGGAGACAACCCACTCTCCCGTTCGA | 510 |
| 63 | CYP1B1 | AATTAACCCTCACTAAAGGGAGAAGCCAGTAGCAGGAGCCTCCT | 511 |
| 64 | CYP1B1 | AATTAACCCTCACTAAAGGGAGAAGCGGAACGAGAGGTGAGC | 512 |
| 65 | CYP1B1 | AATTAACCCTCACTAAAGGGAGATGGGGCGTGAAGAGTTG | 513 |
| 66 | CYP3A4 | AATTAACCCTCACTAAAGGGAGAGCAAAGAATCAGACACACACC | 514 |
| 67 | CYP19 | AATTAACCCTCACTAAAGGGAGATAGAAATATCCAACATTACAAAAGC | 515 |
| 68 | GSTM3 | AATTAACCCTCACTAAAGGGAGACCTTCAGCTTTGCGAACTCA | 516 |
| 69 | SULT1A1 | AATTAACCCTCACTAAAGGGAGACCTCATGAAGGGCGCATTG | 517 |
| 70 | VDR | AATTAACCCTCACTAAAGGGAGAGTGGCTCCGTCTCCTGCAC | 518 |
| 71 | VDR | AATTAACCCTCACTAAAGGGAGATACTGCTTGGAGTGTTCCTC | 519 |
| 72 | MTHFR | AATTAACCCTCACTAAAGGGAGATCACAAAGGCGGAGAATGTG | 520 |
| 73 | MTHFR | AATTAACCCTCACTAAAGGGAGATGGTTCTCCCGAGAGTAAA | 521 |
| 74 | TLR4 | AATTAACCCTCACTAAAGGGAGACCCTGATGACATCCTGATTG | 522 |
| 75 | CYP2C19 | AATTAACCCTCACTAAAGGGAGATCACTTTCCATAAAGCAAGGTT | 523 |
| 76 | CYP2C19 | AATTAACCCTCACTAAAGGGAGATCTATTTCAGGCCTTGGTCA | 524 |
| 77 | CYP2C19 | AATTAACCCTCACTAAAGGGAGACAAGCCACTCAAGGAGCATA | 525 |
| 78 | NAT2 | AATTAACCCTCACTAAAGGGAGAGGCAGGAGATGAGAATTAAGAAA | 526 |
| 79 | NAT2 | AATTAACCCTCACTAAAGGGAGAGGCTGATCCTTCCCAGAAAT | 527 |
| 80 | NAT2 | AATTAACCCTCACTAAAGGGAGATGCATGAGAAGGTGAACCA | 528 |
| 81 | NAT2 | AATTAACCCTCACTAAAGGGAGACAGGATCAAGCCTACCAAAC | 529 |
| 82 | NAT2 | AATTAACCCTCACTAAAGGGAGACAGTTGGGTGATACATACACAAGG | 530 |
| 83 | BRCA2 | AATTAACCCTCACTAAAGGGAGATCAGGTGGTCTGAATGTTCC | 531 |
| 84 | CHEK2 | AATTAACCCTCACTAAAGGGAGACACACCACTCCCAACAGAAACA | 532 |
| 85 | BIP1A1 | AATTAACCCTCACTAAAGGGAGAGCAGTGGTAGTGGTGCCATT | 533 |
| 86 | AR | AATTAACCCTCACTAAAGGGAGATGGTGTAACCTCCCTTGAAA | 534 |
| 87 | AR | AATTAACCCTCACTAAAGGGAGATCCTGCACTTCTAGGCACT | 535 |
| 88 | AR | AATTAACCCTCACTAAAGGGAGACCTTCACTGGGTGTGAAAT | 536 |
| 89 | AR | AATTAACCCTCACTAAAGGGAGAGTGGACAGGAGGACAAA | 537 |
| 90 | IL6 | AATTAACCCTCACTAAAGGGAGAGCCTCAGACATGTTGAGTCC | 538 |

Figure 4A: Table 4

Equation variables

| | | B | E.T. | Wald | gl | Sig. | Exp(B) |
|---|---|---|---|---|---|---|---|
| Step 1 | PSA | .070 | .020 | 12.564 | 1 | .000 | 1.072 |
| | Constant | -1.384 | .259 | 28.675 | 1 | .000 | .250 |
| Step 2 | SNP46 | | | 7.402 | 2 | .025 | |
| | SNP46(1) | .930 | .346 | 7.234 | 1 | .007 | 2.534 |
| | SNP46(2) | .500 | .450 | 1.232 | 1 | .267 | 1.649 |
| | PSA | .070 | .020 | 12.901 | 1 | .000 | 1.073 |
| | Constant | -1.985 | .375 | 27.971 | 1 | .000 | .137 | a. Variables introduced on step 1   1: PSA.
b. Variables introduced on step 2   2: SNP46.

Figure 5A: Table 5

| Step 5 | | | | | | | |
|---|---|---|---|---|---|---|---|
| | SNP24 | | | 7.394 | 2 | .025 | |
| | SNP24(1) | .199 | .368 | .298 | 1 | .587 | 1.221 |
| | SNP24(2) | 3.439 | 1.273 | 7.299 | 1 | .007 | 31.151 |
| | SNP48 | | | 6.290 | 2 | .043 | |
| | SNP48(1) | .973 | .391 | 6.202 | 1 | .013 | 2.646 |
| | SNP48(2) | .814 | .499 | 2.655 | 1 | .103 | 2.256 |
| | PSA | .090 | .023 | 15.298 | 1 | .000 | 1.094 |
| | EDADDEBU | .067 | .027 | 5.978 | 1 | .014 | 1.069 |
| | ESTC_COD | | | 10.008 | 2 | .007 | |
| | ESTC_COD(1) | 1.054 | .388 | 7.373 | 1 | .007 | 2.870 |
| | ESTC_COD(2) | 1.252 | .436 | 8.252 | 1 | .004 | 3.499 |
| | Constante | -7.709 | 1.932 | 15.929 | 1 | .000 | .000 |

Figure 6A: Table 6

Equation variables

|  |  | B | E.T. | Wald | gl | Sig. | Exp(B) |
|---|---|---|---|---|---|---|---|
| Step 7 | SNP24 |  |  | 5.021 | 2 | .081 |  |
|  | SNP24(1) | .555 | .368 | 2.272 | 1 | .132 | 1.741 |
|  | SNP24(2) | 2.196 | 1.224 | 3.217 | 1 | .073 | 8.988 |
|  | SNP31(1) | 2.703 | .927 | 8.510 | 1 | .004 | 14.925 |
|  | SNP56_recod(1) | -1.540 | .651 | 5.595 | 1 | .018 | .214 |
|  | PSA | .074 | .023 | 10.299 | 1 | .001 | 1.076 |
|  | GLPZ_COD_recod(1) | 1.076 | .357 | 9.099 | 1 | .003 | 2.934 |
|  | MARG_COD(1) | 1.405 | .519 | 7.344 | 1 | .007 | 4.076 |
|  | MARO_COD(1) | 1.367 | .332 | 16.987 | 1 | .000 | 3.925 |
|  | Constante | -2.498 | .399 | 39.151 | 1 | .000 | .082 |

Figure 7A: Table 7

Equation variables

| | | B | E.T. | Wald | gl | Sig. | Exp(B) |
|---|---|---|---|---|---|---|---|
| Step 8 | SNP24 | | | 4.780 | 2 | .092 | |
| | SNP24(1) | .341 | .394 | .746 | 1 | .388 | 1.406 |
| | SNP24(2) | 2.566 | 1.234 | 4.326 | 1 | .038 | 13.015 |
| | SNP25 | | | 6.093 | 2 | .048 | |
| | SNP25(1) | .016 | .357 | .002 | 1 | .964 | 1.016 |
| | SNP25(2) | 1.775 | .733 | 5.873 | 1 | .015 | 5.903 |
| | SNP31(1) | 1.703 | .695 | 6.012 | 1 | .014 | 5.492 |
| | SNP32 | | | 10.464 | 2 | .005 | |
| | SNP32(1) | -1.114 | .414 | 7.235 | 1 | .007 | .328 |
| | SNP32(2) | -3.358 | 1.585 | 4.490 | 1 | .034 | .035 |
| | PSA | .100 | .024 | 17.420 | 1 | .000 | 1.105 |
| | GLPZ_COD_recod(1) | 1.195 | .382 | 9.797 | 1 | .002 | 3.303 |
| | MARG_COD(1) | 1.164 | .516 | 5.092 | 1 | .024 | 3.204 |
| | MARO_COD(1) | 1.486 | .367 | 16.418 | 1 | .000 | 4.419 |
| | Constante | -3.026 | .480 | 39.728 | 1 | .000 | .048 |

Figure 18: Table 18

| Variable | Model 1 | Model 2 | Model 3 | Model 4 |
|---|---|---|---|---|
| SNPs | | | | |
| 24 | | X 447Stop (G) | X 447Stop (G) | X 447Stop (G) |
| 25 | | | | X 72Pro (G) |
| 31 | | | X 1384G | X 1384G |
| 32 | | | | X (C) Met160 |
| 46 | X 2548A | X 2548A | | |
| 56 | | | X C3798 | |
| Clinical Pre-operative | | | | |
| PSA | X (Higher level, worse prognosis | x (Higher level, worse prognosis | x (Higher level, worse prognosis | x (Higher level, worse prognosis |
| Onset age | | X (Higher onset age, worse prognosis) | | |
| Clinical stage | | X (Higher clinical stage, worse prognosis) | | |
| Clinical Post-operative | | | | |
| Prostatectomy Gleason grade | | | X (Higher Gleason grade, worse prognosis) | X (Higher Gleason grade, worse prognosis) |
| Surgical oncologic margins | | | X (Positive margins is associated to poor prognosis) | X (Positive margins is associated to poor prognosis) |
| Surgical gland margins | | | X (Positive margins is associated to poor prognosis) | X (Positive margins is associated to poor prognosis) |

Figure 19A: Table 19

Pairwise comparisons

| | SNP31 | 0 | | 1 | |
|---|---|---|---|---|---|
| | | Chi-square | Sig. | Chi-square | Sig. |
| Log Rank (Mantel-Cox) | 0 | | | 1.459 | .227 |
| | 1 | 1.459 | .227 | | |
| Breslow (Generalized Wilcoxon) | 0 | | | 2.405 | .121 |
| | 1 | 2.405 | .121 | | |
| Tarone-Ware | 0 | | | 2.056 | .152 |
| | 1 | 2.056 | .152 | | |

Figure 20A: Table 20

Pairwise comparisons

| | SNP32 | 0 | | 1 | | 2 | |
|---|---|---|---|---|---|---|---|
| | | Chi-square | Sig. | Chi-square | Sig. | Chi-square | Sig. |
| Log Rank (Mantel-Cox) | 0 | | | .080 | .778 | .438 | .508 |
| | 1 | .080 | .778 | | | .428 | .513 |
| | 2 | .438 | .508 | .428 | .513 | | |
| Breslow (Generalized Wilcoxon) | 0 | | | .123 | .726 | .468 | .494 |
| | 1 | .123 | .726 | | | .354 | .552 |
| | 2 | .468 | .494 | .354 | .552 | | |
| Tarone-Ware | 0 | | | .015 | .902 | .450 | .502 |
| | 1 | .015 | .902 | | | .380 | .538 |
| | 2 | .450 | .502 | .380 | .538 | | |

Figure 21A: Table 21

Pairwise comparisons

| | SNP56_recod | 0 | | 1 | |
|---|---|---|---|---|---|
| | | Chi-square | Sig. | Chi-square | Sig. |
| Log Rank (Mantel-Cox) | 0 | | | .981 | .322 |
| | 1 | .981 | .322 | | |
| Breslow (Generalized Wilcoxon) | 0 | | | .330 | .566 |
| | 1 | .330 | .566 | | |
| Tarone-Ware | 0 | | | .535 | .465 |
| | 1 | .535 | .465 | | |

PROGNOSTIC METHOD

RELATED APPLICATIONS

This application is a national stage filing under 35 U.S.C. §371 of PCT International application PCT/IB2007/002364 designating the United States of America, and filed Jul. 12, 2007, the entire contents of which are hereby incorporated herein by reference. This application claims the benefit of priority under 35 U.S.C. §119 from Application No. GB 0613840.8 filed in the United Kingdom on Jul. 12, 2006, the entire contents of which are hereby incorporated herein by reference.

FIELD OF THE INVENTION

The invention relates to methods and products in particular, microarrays for in vitro genotyping of prostate cancer (PCa) associated genetic variations. The invention further relates to methods for the prognosis and treatment of PCa, and to products for use therein.

BACKGROUND TO THE INVENTION

Prostate cancer (PCa) remains the most commonly diagnosed malignancy and second leading cause of cancer death in men older than age 40 years. There are three stages of prostate cancer: localised PCa; locally advanced PCa; and metastatic PCa.

For patients having localised PCa (confined to the prostate gland), and treated with radical prostatectomy, there is a risk of cancer progression or recurrence, usually indicated by an increased level of prostate-specific antigen (PSA). Those who experience early increases in PSA levels are more likely to develop metastatic lesions, and have a poor prognosis. Several nomograms have been developed to try to predict the probability of this biochemical progression after surgery, usually based on classical clinical parameters. However, these have failed to accurately predict PSA recurrence.

Therefore, there remains in the art a need for reliable means of predicting the course of PCa, and providing a basis for more targeted treatments.

PCa is considered to be a complex genetic disease in which inheritance is not considered to be the simple Mendelian example. Association studies have recently identified several genes in which one or more genetic variations result in a higher or lower risk of contracting the disease, a better or worse response to drugs and/or a better or worse prognosis. Single nucleotide polymorphisms (SNPs) in germ-line DNA have been associated to highly aggressive or drug-resistant types of PCa (Table 1A).

Development of a polygenic model for PCa, incorporating multiple loci from the individual genes, requires a means for discriminating alleles at multiple genetic loci that is sufficiently sensitive, specific and reproducible for clinical use.

DNA chips are often used to determine alleles at generic loci.

In 2001, the Consortium for the Human Genome Project and the private company Celera presented the first complete example of the human genome with 30,000 genes. From this moment on, the possibility of studying the complete genome or large scale (high-throughput) studies began. So-called "DNA-chips", also named "micro-arrays", "DNA-arrays" or "DNA bio-chips" are apparatus that functional genomics can use for large scale studies. Functional genomics studies changes in the expression of genes due to environmental factors and to genetic characteristics of an individual. Gene sequences present small interindividual variations at one unique nucleotide called an SNP ("single nucleotide polymorphism"), which in a small percentage are involved in changes in the expression and/or function of genes that cause certain pathologies. The majority of studies which apply DNA-chips study gene expression, although chips are also used in the detection of SNPs.

The first DNA-chip was the "Southern blot" where labelled nucleic acid molecules were used to examine nucleic acid molecules attached to a solid support. The support was typically a nylon membrane.

Two breakthroughs marked the definitive beginning of DNA-chip. The use of a solid non-porous support, such as glass, enabled miniaturisation of arrays thereby allowing a large number of individual probe features to be incorporated onto the surface of the support at a density of >1,000 probes per $cm^2$. The adaptation of semiconductor photolithographic techniques enabled the production of DNA-chips containing more than 400,000 different oligonucleotides in a region of approximately 2 $\mu m^2$, so-called high density DNA-chips.

In general, a DNA-chip comprises a solid support, which contains hundreds of fragments of sequences of different genes represented in the form of DNA, cDNA or fixed oligonucleotides, attached to the solid surface in fixed positions. The supports are generally glass slides for the microscope, nylon membranes or silicon "chips". It is important that the nucleotide sequences or probes are attached to the support in fixed positions as the robotized localisation of each probe determines the gene whose expression is being measured. DNA-chips can be classified as:

high density DNA-chips: the oligonucleotides found on the surface of the support, e.g. glass slides, have been synthesized "in situ", by a method called photolithography.

low density DNA-chips: the oligonucleotides, cDNA or PCR amplification fragments are deposited in the form of nanodrops on the surface of the support, e.g. glass, by means of a robot that prints those DNA sequences on the support. There are very few examples of low density DNA-chips which exist: a DNA-chip to detect 5 mutations in the tyrosinase gene; a DNA-chip to detect mutations in p53 and k-ras; a DNA-chip to detect 12 mutations which cause hypertrophic cardiomyopathy; a DNA-chip for genotyping of *Escherichia coli* strains; or DNA-chips to detect pathogens such as *Cryptosporidium parvum* or rotavirus.

For genetic expression studies, probes deposited on the solid surface, e.g. glass, are hybridized to cDNAs synthesized from mRNAs extracted from a given sample. In general the cDNA has been labelled with a fluorophore. The larger the number of cDNA molecules joined to their complementary sequence in the DNA-chip, the greater the intensity of the fluorescent signal detected, typically measured with a laser. This measure is therefore a reflection of the number of mRNA molecules in the analyzed sample and consequently, a reflection of the level of expression of each gene represented in the DNA-chip.

Gene expression DNA-chips typically also contain probes for detection of expression of control genes, often referred to as "house-keeping genes", which allow experimental results to be standardized and multiple experiments to be compared in a quantitative manner. With the DNA-chip, the levels of expression of hundreds or thousands of genes in one cell can be determined in one single experiment. cDNA of a test sample and that of a control sample can be labelled with two different fluorophores so that the same DNA-chip can be used to study differences in gene expression.

DNA-chips for detection of genetic polymorphisms, changes or mutations (in general, genetic variations) in the DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

One strategy used to detect genetic variations involves hybridization to sequences which specifically recognize the normal and the mutant allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the mutant allele.

Another strategy to detect genetic variations comprises carrying out an amplification reaction or extension reaction on the DNA-chip itself.

For differential hybridisation based methods there are a number of methods for analysing hybridization data for genotyping:

Increase in hybridization level: The hybridization level of complementary probes to the normal and mutant alleles are compared.

Decrease in hybridization level: Differences in the sequence between a control sample and a test sample can be identified by a fall in the hybridization level of the totally complementary oligonucleotides with a reference sequence. A complete loss is produced in mutant homozygous individuals while there is only 50% loss in heterozygotes. In DNA-chips for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. The increased number of oligonucleotides used to reconstruct the sequence reduces errors derived from fluctuation of the hybridization level. However, the exact change in sequence cannot be identified with this method; sequencing is later necessary in order to identify the mutation.

Where amplification or extension is carried out on the DNA-chip itself, three methods are presented by way of example:

In the Minisequencing strategy, a mutation specific primer is fixed on the slide and after an extension reaction with fluorescent dideoxynucleotides, the image of the DNA-chip is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of DNA-chips with oligonucleotides complementary to these sequences or "tags" allows the capture of the resultant products of the extension. Examples of this include the high density DNA-chip "Flex-flex" (Affymetrix).

For genetic diagnosis, simplicity must be taken into account. The need for amplification and purification reactions presents disadvantages for the on-chip extension/amplification methods compared to the differential hybridization based methods.

Typically, DNA-chip analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Geneome Research; 11:1913-1925 (2001).

Thus, despite advances in technology, the problems of existing methods is simultaneously analysing a large number of genetic variations in a sensitive, specific and reproducible way, has prevented the application of DNA-chips for routine use in clinical diagnosis

SUMMARY OF THE INVENTION

The inventors have identified new means for prognosing recurrence of prostate cancer using combinations of informative SNP variables and clinical variables. Accordingly the invention provides a method of prognosing prostate cancer (PCa) recurrence following prostatectomy in a subject, which comprises:

(I) obtaining outcomes for one or more single nucleotide polymorphism variables and one or more clinical variables listed in Table 18 for the subject; and (II) using the outcomes obtained in (I) to prognose PCa recurrence;

wherein (i) an outcome for an SNP variable is the identity of the nucleotide in the genomic DNA of the subject at the position of the single nucleotide polymorphism;

(ii) an outcome for the clinical variable PSA is the pre-prostatectomy level of prostate specific antigen (PSA) in the blood of the subject;

(iii) an outcome for the clinical variable onset age is the age in years at which the subject was diagnosed with PCa;

(iv) an outcome for, the clinical variable clinical stage is a T value assigned to the PCa in the subject before prostatectomy;

(v) an outcome for the clinical variable prostatectomy gleason grade is a number from 2 to 10 assigned after prostatectomy;

(vi) an outcome for the clinical variable surgical oncologic margins is a yes or no to indicate the presence (yes) or absence (no) of tumour cells at the borders of a surgically resected tumour;

(vii) an outcome for the clinical variable surgical gland margins is a yes or no to indicate the presence (yes) or absence (no) of tumour cells at the borders of the prostate gland; and wherein:

(a) the variables for which outcomes are obtained in step (I) comprise the model 1 SNP and clinical variables in Table 18; and/or
(b) the variables for which outcomes are obtained in step (I) comprise the model 2 SNP and clinical variables in Table 18; and/or
(c) the variables for which outcomes are obtained in step (I) comprise the model 3 SNP and clinical variables in Table 18; and/or
(d) the variables for which outcomes are obtained in step (I) comprise the model 4 SNP and clinical variables in Table 18.

The invention also provides a method of deriving a probability function for use in prognosing PCa recurrence following prostatectomy in a subject, a computational method of deriving a probability function for use in prognosing PCa recurrence following prostatectomy in a subject and a method for prognosing PCa recurrence in a subject comprising use of a probability function derived using the data in any one of Tables 4 to 7, as set out in the claims.

The inventors have also identified SNPs which have significant allelic association with prostate cancer recurrence. Accordingly the invention also provides a method of prognosing PCa recurrence in a subject comprising determining the genotype of the subject at one or more positions of single nucleotide polymorphism selected from SNPs 9, 24, 25, 28, 34, 46, 47, 51, 58 and 80 in Table 1B.

The invention also provides an in vitro method for genotyping PCa associated genetic variations in an individual as set out in the claims.

Further aspects of the invention include a computational method for obtaining a genotype from DNA-chip hybridisation intensity data, a method of deriving linear functions for use in a genotyping method of the invention, a computational method of deriving linear functions for use in a genotyping method of the invention, a method of diagnosing PCa or susceptibility to PCa in an individual comprising genotyping an individual with respect to one or more genetic variations, methods for selecting a treatment for PCa in a subject and for treating PCa in a subject, a method of identifying genetic variations predictive of a particular PCa phenotype and a method of predicting the likely development of a PCa phenotype in an individual using the identified variation(s).

Still further aspects include a computer system comprising a processor and means for controlling the processor to carry out a computational method of the invention, a computer program comprising computer program code which when run on a computer or computer network causes the computer or computer network to carry out a computational method of the invention.

The invention also provides a DNA chip or microarray suitable for use in the methods of the invention, an oligonucleotide probe, probe pair, or 4-probe set listed in Table 2 (FIG. 2), an oligonucleotide primer or primer pair listed in Table 3A and/or 3B (FIG. 3), a PCR amplification kit comprising at least one pair of the listed primers, a diagnostic kit for detection of PCa associated genetic variations and a kit for prognosing PCa recurrence in a subject.

All of these aspects of the invention are as set out in the claims.

Brief Description of the Sequences
SEQ ID NOS: 1-360 are probes suitable for detection of the PCa associated genetic variations in Table 1A. These probes are listed in Table 2.
SEQ ID NOS: 361-538 are PCR primers suitable for amplifying target DNA regions comprising PCa associated genetic variations listed in Table 1A. These primers are listed in Tables 3A and 3B.
SEQ ID NO: 539 is an external control nucleic acid.
SEQ ID NOS: 540 & 541 are probes suitable for detection of the external control nucleic acid of SEQ ID NO: 539.
SEQ ID NO: 542 is a forward TAG sequence.
SEQ ID NO: 543 is a reverse TAG sequence.

BRIEF DESCRIPTION OF THE FIGURES

FIG. 1
(A) Table 1A shows genetic variations (SNPs) associated with PCa and which may be analysed as described herein. RefSNP codes (rs#) for each SNP are taken from the Single Nucleotide Polymorphism Database (dbSNP) curated by the National Center for Biotechnology Information (NCBI) as found at ncbi.nlm.nih.gov/entrez/query.fcgi?CMD=search&DB=snp, as at 4 Jul. 2007). The sequences of all the genes mentioned in Table 1A are known and recognized on the following websites: GeneBank (NCBI), GeneCard (Weizmann Institute of Sciences) and Snpper.chip.org (Innate Immunity PGA).
(B) Table 1B shows the nucleotide alleles for genotypes 0, 1 and 2 as used herein, for SNPs 9, 24, 25, 28, 31, 32, 34, 46, 47, 51, 56, 58, 80. The Table also shows, for each SNP, the genotype which is associated with a poorer prognosis (these genotypes are in bold print). These are: SNP9 (TT), SNP 24 (GG), SNP 25 (CC), SNP 28 (AA), SNP 31 (AG/GG). SNP 32 (CC), SNP 34 (AA). SNP 46 (GG), SNP 47 (GG), SNP51 (AA), SNP 56 (CC), SNP 58 (TT), SNP80 (TT). For SNP31, the G allele is associated to poor prognosis but no GG patients were observed in the present studied population, so AG genotype is marked as the one with poor prognosis compared to AA.

FIG. 2: Table 2 lists oligonucleotide probes for discriminating between alleles at the SNPs listed in Table 1A. The table lists two probe pairs for each SNP (a 4-probe set).

FIGS. 3A/3B: Tables 3A and 3B lists oligonucleotide primers for PCR amplification of nucleic acid regions containing the SNPs listed in Table 1A. Forward primers are listed in Table 3A, and reverse primers in Table 3B.

Figure 4B:
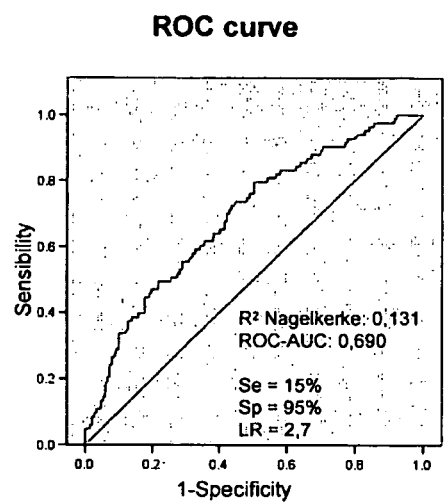
FIG. 4
(A) Table 4 shows the SNP (46) and the clinical variable (PSA) together with their significance (Sig.) and their odds ratios (Exp (B)) used to compute the model 1 for the prediction of the phenotype. This model provides the probability of PSA recurrence (PSA>0.2 ng/ml) from 0 (no risk) to 1 (maximum risk).
(B) ROC (receiver operating characteristic) curve obtained for the model 1 that allows the estimation of its discriminatory power. The ROC curve has been calculated in order to maximize the specificity, thus reducing at the same time the "false" positive rate. A specificity of 95% with a sensibility of 15% is the cut-off for this model regarding the probability of PSA recurrence. This model shows a likelihood ratio (LR) value of 2.7.

(A) Table 6 shows the SNPs (24, 31 and 56) and the clinical variables (PSA, Prostatectomy Gleason and Surgical Margins) together with their significance (Sig.) and their odds ratios (Exp (B)) used to compute the model 3 for the prediction of the phenotype. This model provides the probability of PSA recurrence (PSA>0.2 ng/ml) from 0 (no risk) to 1 (maximum risk).

(B) ROC (receiver operating characteristic) curve obtained for the model 3 that allows the estimation of its discriminatory power. The ROC curve has been calculated in order to maximize the specificity, thus reducing at the same time the "false" positive rate. A specificity of 95% with a sensibility of 30% is the cut-off for this model regarding the probability of PSA recurrence. This model shows a likelihood ratio (LR) value of 5.7.

FIG. 7

(A) Table 7 shows the SNPs (24, 25, 31 and 32) and the clinical variables (PSA, Prostatectomy Gleason and Surgical Margins) together with their significance (Sig.) and their odds ratios (Exp (B)) used to compute the model 4 for the prediction of the phenotype. This model provides the probability of PSA recurrence (PSA>0.4 ng/ml) from 0 (no risk) to 1 (maximum risk).

(B) ROC (receiver operating characteristic) curve obtained for the model 4 that allows the estimation of its discriminatory power. The ROC curve has been calculated in order to maximize the specificity, thus reducing at the same time the "false" positive rate. A specificity of 95% with a sensibility of 42% is the cut-off for this model regarding the probability of PSA recurrence. This model shows a likelihood ratio (LR) value of 8.5.

FIG. 8

(A) Table 8 showing the pairwise P values (labelled Sig.) for three common statistical tests between alleles 0, 1 and 2 of SNP9.

(B) Kaplan-Meier curves displaying estimated PSA survival for patients carrying each of the three genotypes 0, 1 and 2 for SNP 9.

FIG. 9:

(A) Table showing the pairwise P values (labelled Sig.) for three common statistical tests between genotypes 0, 1 and 2 of SNP24 (LPL, S447S, S447X and X447X).

(B) Kaplan-Meier curves displaying estimated PSA survival for patients carrying each of the three genotypes for SNP24.

FIG. 10

(A) Table showing the pairwise P values (labelled Sig.) for three common statistical tests between alleles 0, 1 and 2 of SNP25 (p53, R72R, R72P and P72P).

(B) Kaplan-Meier curves displaying estimated PSA survival for patients carrying each of the three genotypes for SNP25.

FIG. 11

(A) Table showing the pairwise P values (labelled Sig.) for three common statistical tests between alleles 0, 1 and 2 of SNP28.

(B) Kaplan-Meier curves displaying estimated PSA survival for patients carrying each of the three genotypes 0, 1 and 2 for SNP28.

FIG. 12

(A) Table showing the pairwise P values (labelled Sig.) for three common statistical tests between alleles 0, 1 and 2 of SNP34.

(B) Kaplan-Meier curves displaying estimated PSA survival for patients carrying each of the three genotypes 0, 1 and 2 of SNP34.

FIG. 13

(A) Table showing the pairwise P values (labelled Sig.) for three common statistical tests between alleles 0, 1 and 2 of SNP46 (Leptin, G-2548G, G-2548A and A-2548A).

(B) Kaplan-Meier curves displaying estimated PSA survival for patients carrying each of the three genotypes for SNP46.

FIG. 14

(A) Table showing the pairwise P values (labelled Sig.) for three common statistical tests between alleles 0, 1 and 2 for SNP47.

(B) Kaplan-Meier curves displaying estimated PSA survival for patients carrying each of the three genotypes 0, 1 and 2 for SNP47.

FIG. 15

(A) Table showing the pairwise P values (labelled Sig.) for three common statistical tests between alleles 0, 1 and 2 for SNP51.

(B) Kaplan-Meier curves displaying estimated PSA survival for patients carrying each of the three genotypes 0, 1 and 2 for SNP51.

FIG. 16

(A) Table showing the pairwise P values (labelled Sig.) for three common statistical tests between alleles 0, 1 and 2 for SNP58.

(B) Kaplan-Meier curves displaying estimated PSA survival for patients carrying each of the three genotypes 0, 1 and 2 for SNP58.

FIG. 17

(A) Table showing the pairwise P values (labelled Sig.) for three common statistical tests between alleles 0, 1 and 2 for SNP80.

(B) Kaplan-Meier curves displaying estimated PSA survival for patients carrying each of the three genotypes 0, 1 and 2 for SNP80.

FIG. 18

Table 18 shows the SNP variables and the clinical variables included in each of models 1 to 4 described herein. The Table indicates which SNP variables and clinical variables (of those listed in the first column) are informative for determining PCa recurrence using each model, and shows which outcome for each variable is associated with poorer prognosis.

FIG. 19

(A) Table showing the pairwise P values (labelled Sig.) for three common statistical tests between alleles 0, 1 and 2 for SNP31.

(B) Kaplan-Meier curves displaying estimated PSA survival for patients carrying each of the three genotypes 0, 1 and 2 for SNP31.

FIG. 20

(A) Table showing the pairwise P values (labelled Sig.) for three common statistical tests between alleles 0, 1 and 2 for SNP32.

(B) Kaplan-Meier curves displaying estimated PSA survival for patients carrying each of the three genotypes 0, 1 and 2 for SNP32.

FIG. 21

(A) Table showing the pairwise P values (labelled Sig.) for three common statistical tests between alleles 0, 1 and 2 for SNP56.

(B) Kaplan-Meier curves displaying estimated PSA survival for patients carrying each of the three genotypes 0, 1 and 2 for SNP56.

DETAILED DESCRIPTION OF THE INVENTION

Prostate cancer, (PCa) is a complex disorder. In general there are three clinically recognised stages of prostate cancer development: localised PCa (generally confined to the prostate gland); locally advanced PCa (breaching the capsule of the prostate gland, with or without involvement of local nodes and/or tissue close to the prostate); and metastatic PCa (invasive cancer involving more distant organs).

Localised PCa is often treated with surgery (radical prostatectomy). However, there is a risk of cancer recurrence following surgery. In clinical terms, an increased prostate-specific antigen (PSA) level within five years of surgery (biochemical progression) usually indicates cancer progression or recurrence. Those who have experienced early PSA recurrence are known to be more prone to develop metastatic lesions and have a poor prognosis.

Using the Proscan DNA microarray of the present invention and clinical investigation, the inventors have identified a number of profiles (based on combinations of SNP and clinical variables) which are informative for predicting such early recurrence. The inventors have thus established models for predicting early recurrence in PCa patients. Accordingly, in one aspect, the present invention relates to methods for prognosis of PCa. In particular, the invention provides methods for reliably determining the likelihood of early prostate cancer recurrence in patients who have undergone radical prostatectomy.

The inventors selected a study population of Spanish male as in Example 2. Each individual was clinically assessed to determine the presence or absence of early (within 5 years of prostatectomy) PCa recurrence. Controversy exists in the art regarding the importance of setting PSA levels as >0.2 ng/ml or >0.4 ng/ml as a threshold for defining "biochemical tumour recurrence". The inventors therefore decided to use both thresholds in their analysis.

Each of the individuals was also tested for various preoperative and postoperative clinical variables and genotyped at a number of genetic loci using the Proscan DNA microarray of the invention (see Example 2).

The inventors then used genetic to select a subset of the most informative SNP for further modelling.

Statistical analysis was carried out to establish four models (each based on a combination of informative SNPs and informative clinical variables) that would allow reliable discrimination between patients having and not having the early PCa recurrence phenotype, with high specificity, sensitivity and accuracy.

The variables which were selected for inclusion in models 1-4 are listed in Table 18 (FIG. 18).

Model 1 discriminates between patients having and not having PSA progression (defined as PSA>0.2 ng/ml) within five years of surgery using preoperative clinical variables and SNPs. Model 2 discriminates between patients having and not having PSA progression (defined as PSA>0.4 ng/ml) within five years of surgery using preoperative clinical variables and SNPs. Model 3 discriminates between patients having and not having PSA progression (defined as PSA>0.2 ng/ml) within five years of surgery using both preoperative and postoperative clinical variables and SNPs. Model 4 discriminates between patients having and not having PSA progression (defined as PSA>0.4 mg/ml) within five years of surgery using preoperative and post operative clinical variables and SNPs.

Figure 5B:
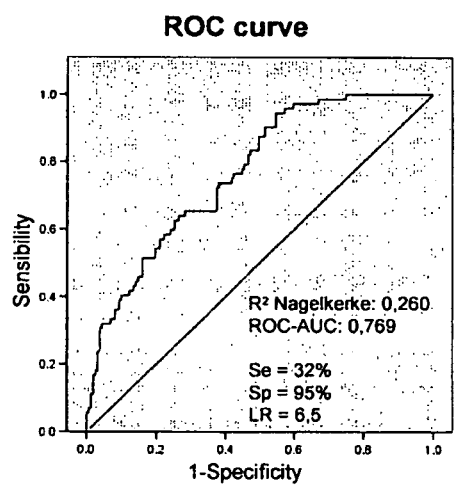
FIG. 5
(A) Table 5 shows the SNPs (46 and 24) and the clinical variables (PSA, Onset Age, Clinical Stage) together with their significance (Sig.) and their odds ratios (Exp (B)) used to compute the model 2 for the prediction of the phenotype. This model provides the probability of PSA recurrence (PSA>0.4 ng/ml) from 0 (no risk) to 1 (maximum risk).
(B) ROC (receiver operating characteristic) curve obtained for the model 2 that allows the estimation of its discriminatory power. The ROC curve has been calculated in order to maximize the specificity, thus reducing at the same time the "false" positive rate. A specificity of 95% with a sensibility of 32% is the cut-off for this model regarding the probability of PSA recurrence. This model shows a likelihood ratio (LR) value of 6.5.
Figure 6B:
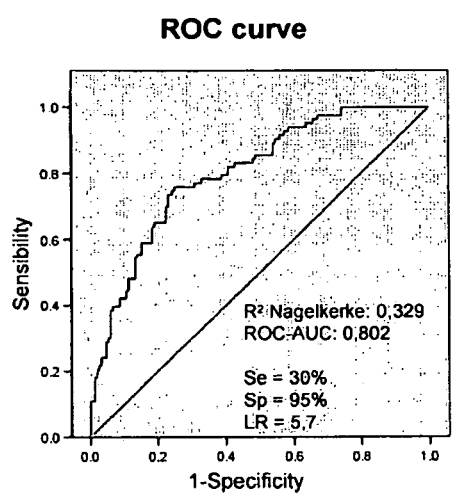
FIG. 6
Figure 7B:
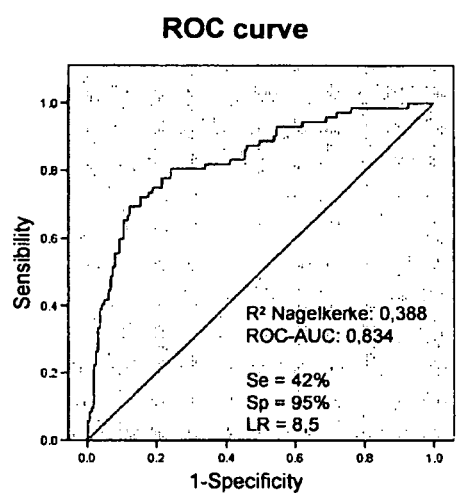

FIGS. 4B-7B show the ROC curves, sensitivity, specificity and positive likelihood ratios (LR+) of each of the models developed by the inventors.

Tables 4-7 show the calculation of probability functions using the discriminating SNPs and clinical variables for each of the models 104 respectively. Regression probability functions are built using the statistical package for the social sciences (SPSS Inc. Headquarters, Chicago, Ill., USA) Version 14.0. SPSS v. 14. B is the coefficient associated to each genotype in the probability function. ET is the error in the calculation of B. Wald is the statistical test. GL freedom degrees, P is the value of the Wald test. X (B) is relative risk. The alternative genotypes, 0, 1 and 2, for the various SNPs are listed in Table 1B.

Figure 8:
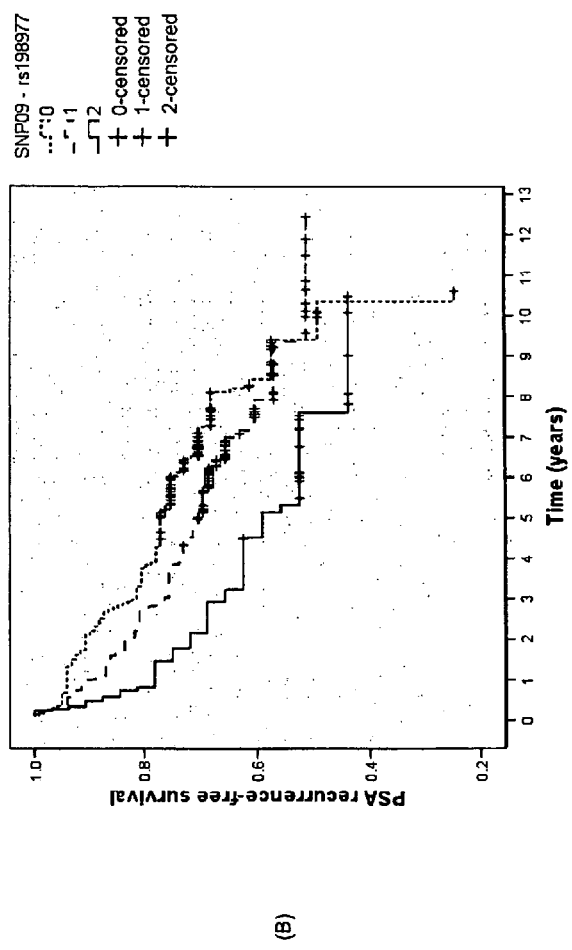
Figure 9:
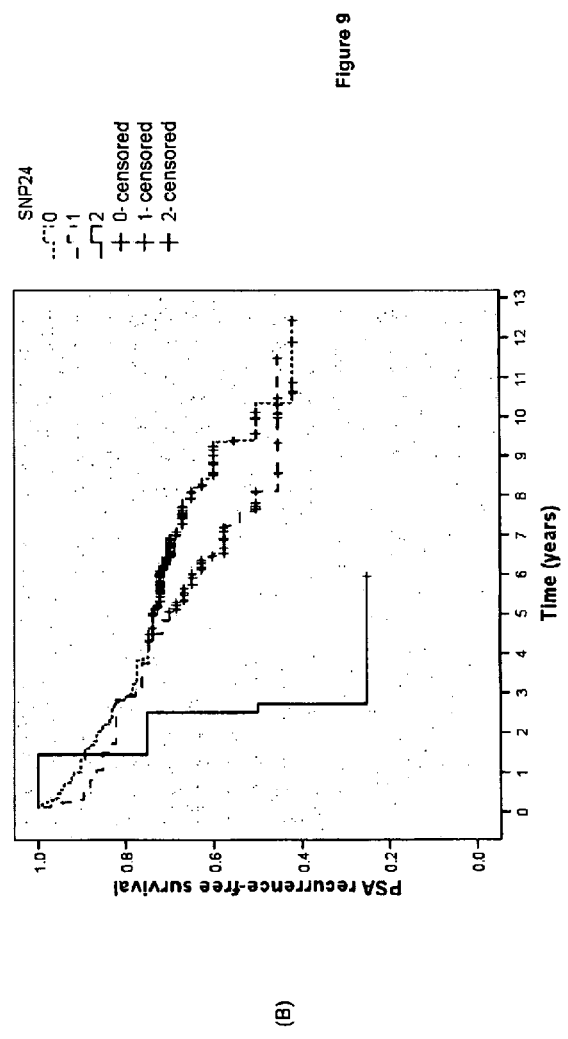
Figure 10:
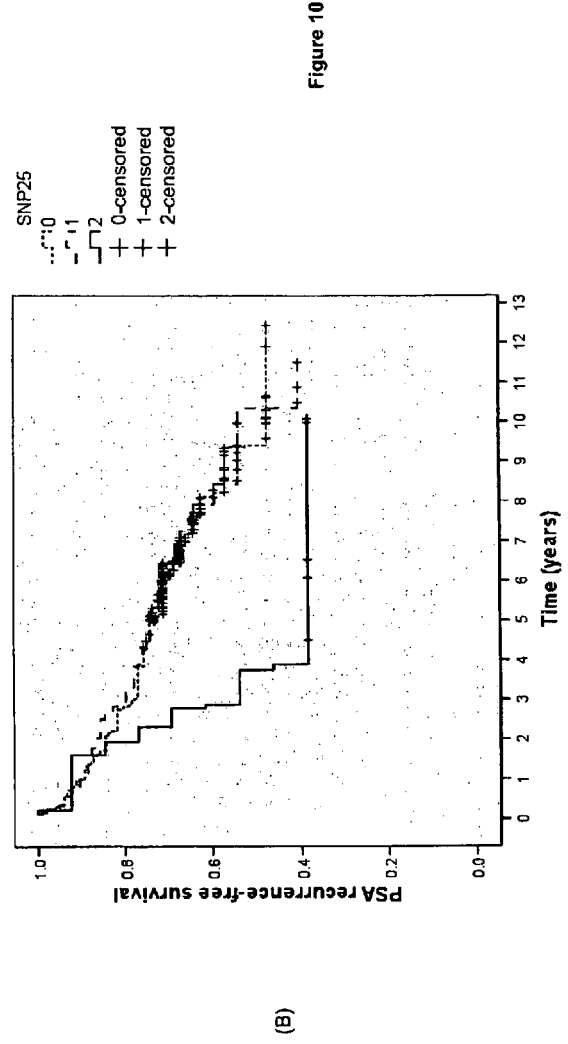
Figure 11:
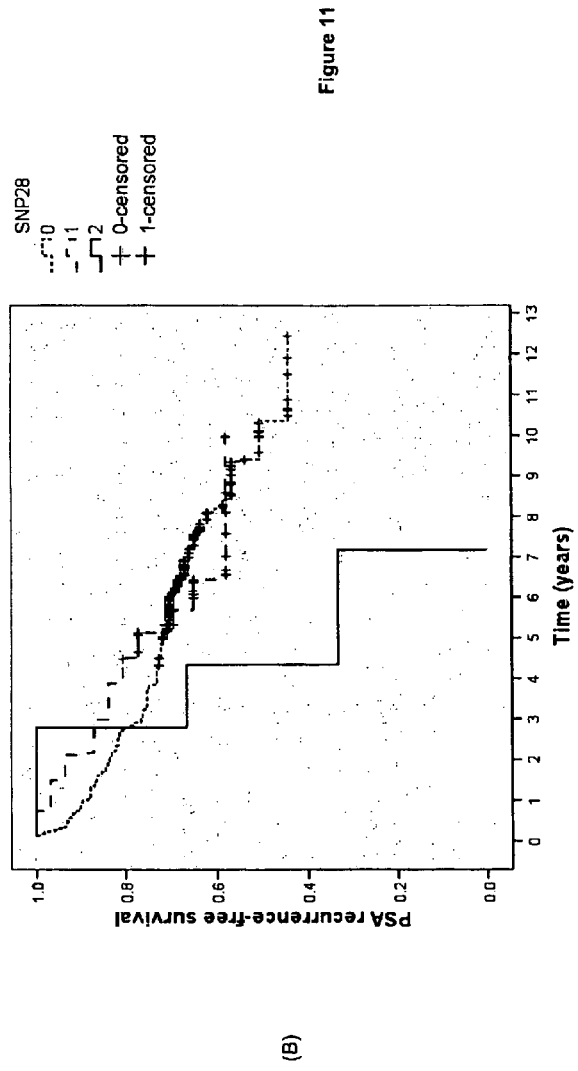
Figure 12:
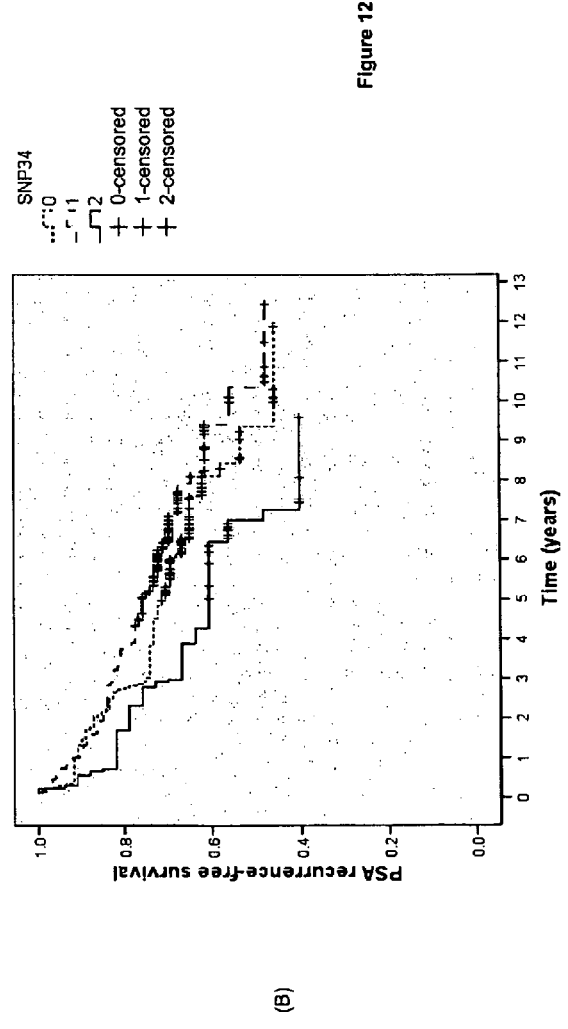
Figure 13:
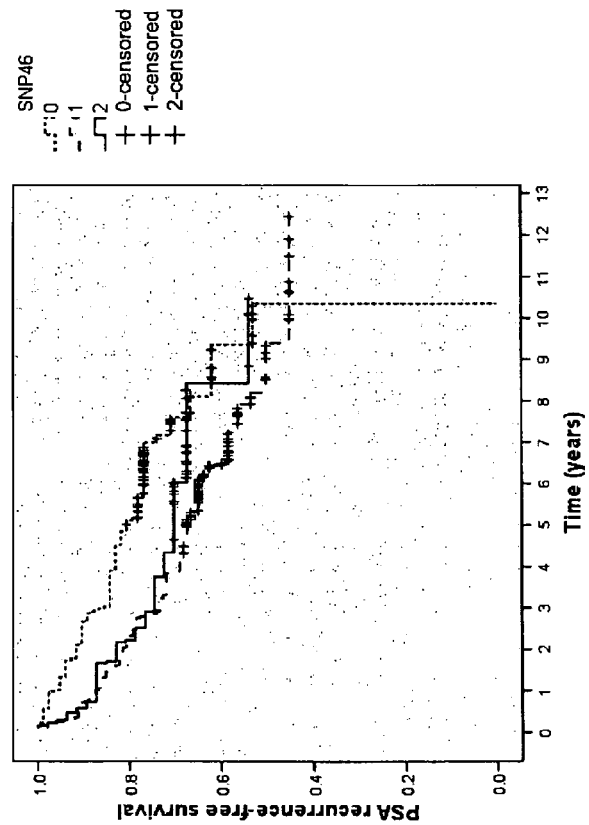
Figure 14:
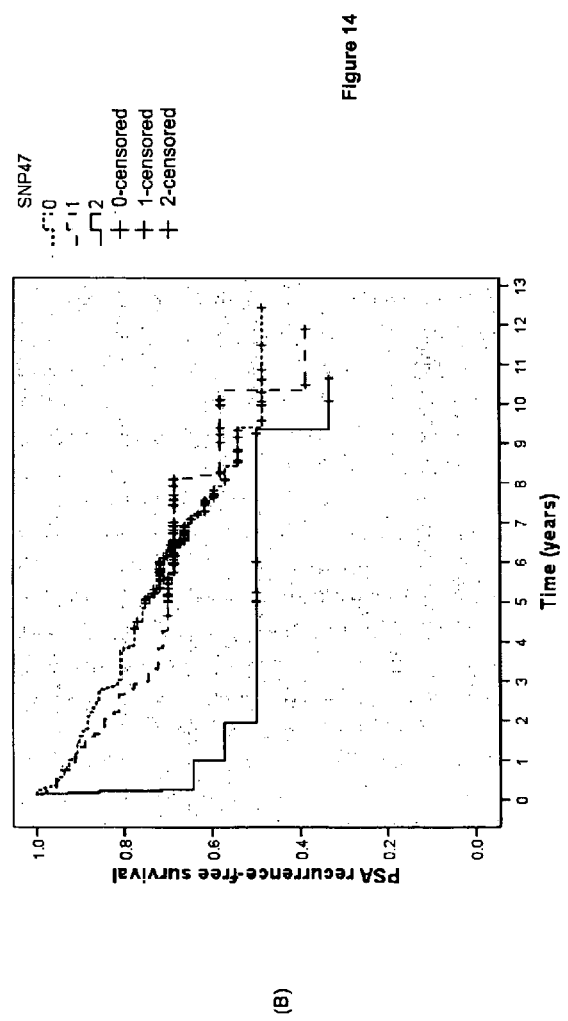
Figure 15:
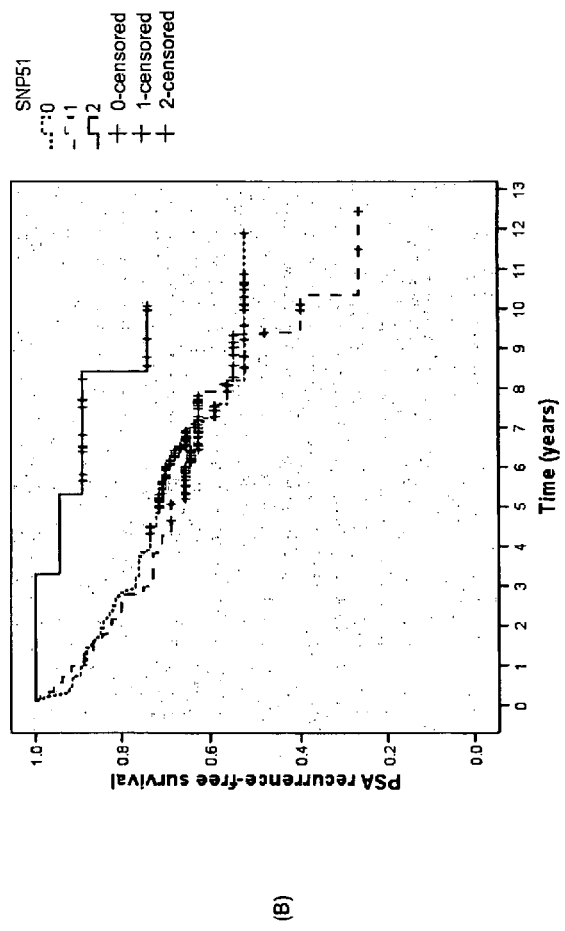
Figure 16:
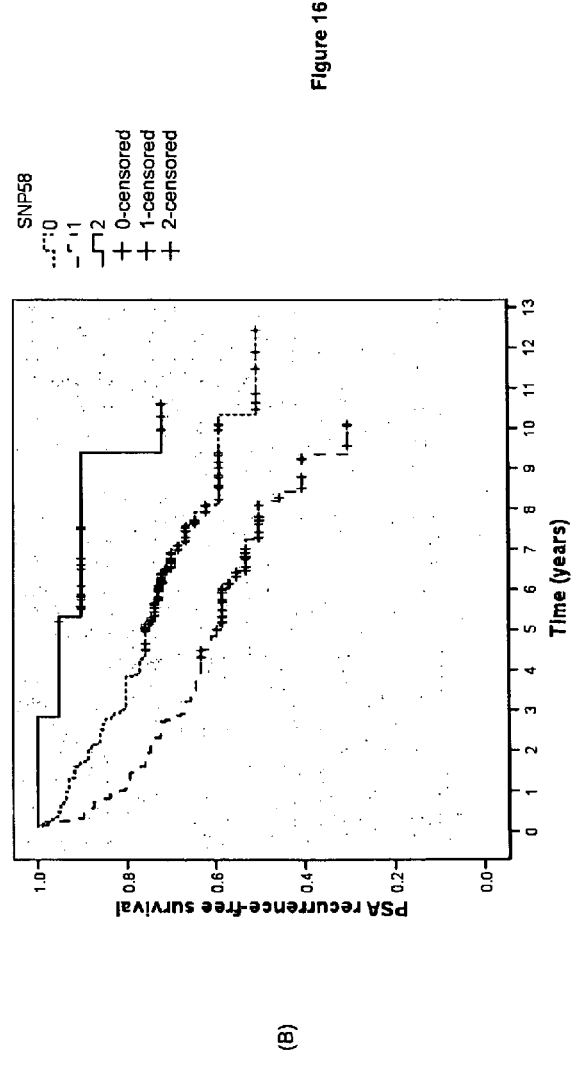
Figure 17:
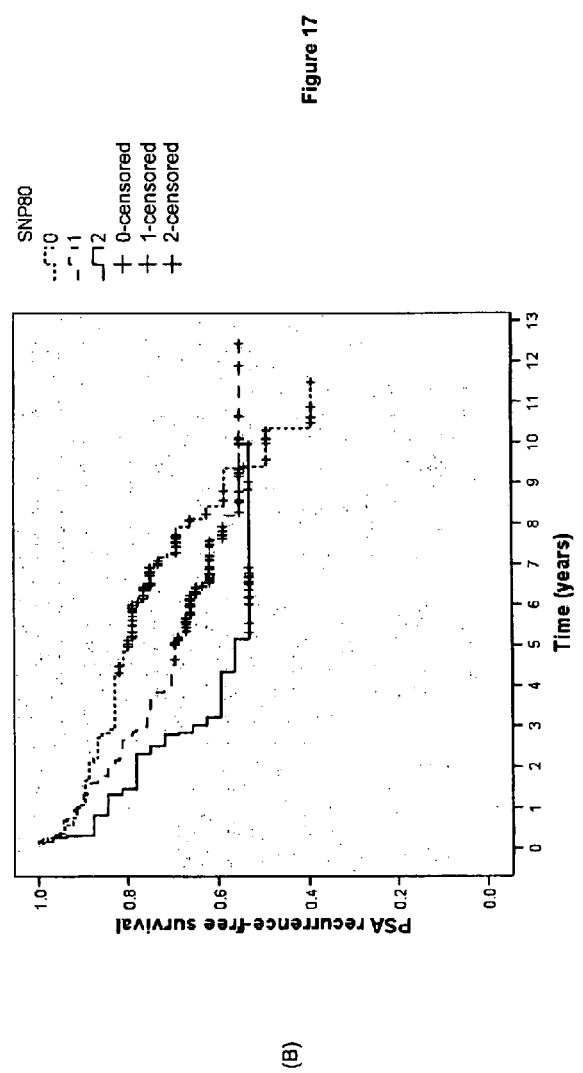

The inventors also investigated the association of individual genetic markers to early PSA recurrence by performing a survival analysis. In this way, the inventors identified 10 SNPs: SNP 9, 24, 25, 28, 34, 46, 47, 51, 58 and 80 showing a significant association between genotype and risk of recurrence ($P<0.05$). The results are shown in FIGS. 8-17.

Thus, the inventors have identified SNPs which are informative for the prognosis of PCa and in particular predicting the likelihood of PCa recurrence following prostatectomy (Table 1B). The clinical and SNP variables identified, and the models constructed using them, provide new means for predicting the development of the early PCa recurrence phenotype in a subject. Thus the invention provides methods for the prognosis of PCa and in particular for predicting the risk of developing an early PCa recurrence after prostatectomy.

In general PCa recurrence is clinically determined as the subject showing biochemical progression. Biochemical progression refers to an increase in levels of Prostate Specific Antigen (PSA) (Stamey T, et al. N Engl J Med. 1987; 317: 909-16. Pound C R, et al. JAMA. 1999; 281:1591-1597)

There is some dispute in the art as to the PSA threshold which indicates biochemical progression. Some sources indicate that the threshold is a serum PSA level>0.2 ng/ml; others that the threshold is PSA level>0.4 ng/ml. Recurrence herein may be defined according to either threshold. Models 1 and 3 described herein may be used to determine likelihood of recurrence defined according to the >0.2 ng/ml threshold. Models 2 and 4 may be used to determine likelihood of recurrence defined according to the >0.2 ng/ml or the 0.4 ng/ml threshold.

In general early recurrence is a recurrence which occurs within 5 years of prostatectomy.

In general the subject is a human male. The subject may be for example, Chinese, Japanese or a Caucasian. Preferably the subject is a Caucasian, such as a Spanish male.

Typically the subject has been diagnosed as having localised PCa. Localised PCa is cancer that has not spread beyond the prostate gland and accounts for about 90 percent of all PCa at diagnosis. A diagnosis of localised PCa is typically made according to four standard tests: Digital rectal examination (DRE), Prostate Specific Antigen (PSA) serum levels, Transrectal ultrasound (TRUS) and TRUS-guided biopsy. (AUA Guidelines 2007, American Urological Association. AUA 2007 Annual Meeting: Media Advisory session. May, 2007).

The subject may be pre-operative or post-operative. Models 3 and 4 are for use post-operatively. Models 1 and 2 may be used pre- or post-operatively. For use of individual SNPs the subject may be pre-operative or post-operative. Pre- or post-operative refers to the period before (pre) or after (post) radical prostatectomy in a patient.

The present prognostic methods involve determining an outcome for each of a number of single nucleotide polymorphism (SNP) variables or predictors. The SNP variables are listed in Table 1B. The SNPs included in models 1 to 4 are listed in FIGS. 4-7 and in FIG. 18. RefSNP codes (rs#) for each SNP are taken from the Single Nucleotide Polymorphism Database (dbSNP) curated by the National Center for Biotechnology Information (NCBI) as found at ncbi.nlm.nih.gov/entrez/query.fcgi?CMD=search&DB=snp, as at 4 Jul. 2007).

An outcome for a given SNP is the identity of the nucleotide at that position in the genomic DNA sequence of a subject, or the genotype of the subject at that SNP. Thus an outcome for a given SNP may be A, T, C or G.

Table 1B lists the alternative genotypes (0, 1 and 2) at each of the SNPs which are useful for prognosis. For SNPs 9, 24, 25, 28, 34, 46, 47, 31 and 80, allele 2 is associated with poor prognosis. For SNPs 51, 58, 32 and 56 allele 0 is associated with poor prognosis.

The inventors found that by determining or obtaining outcomes for these informative SNPs (i.e. nucleotide identities at the SNPs), or particular combinations thereof, it is possible to assess the likelihood of recurrence in a subject.

The present prognostic methods may also comprise determining an outcome for one or more clinical variables for a subject. These clinical variables are also listed in Table 18. The Table also shows which outcomes are linked to a poorer prognosis.

The pre-operative clinical variables included in one or more of the models 1 to 4 are: PSA level; onset age; clinical stage. The post-operative clinical variables included in one or more of the models are: prostatectomy Gleason grade; surgical oncologic margins; and surgical gland margins.

PSA level refers to the preoperative level of the PSA antigen in the blood of the patient. Typically this is determined at diagnosis (typically at routine screenings) and provides a measure in ng/mL. Thus an outcome for this variable a number from 0-1000, typically with one decimal.

Onset age refers to the age in years at which the patient was diagnosed with localised PCa according to the criteria described herein. Thus, an outcome for this variable is a number ranging between 0-150 years.

Clinical stage refers to the stage assigned by the doctor based on the results of all diagnostic tests and biopsies before prostatectomy. Typically this is clinically determined as follows and is in general represented by a T number or value, assigned as follows. T1 is non-palpable PCa, T2 involves a palpable tumor apparently confined within the prostate. If the tumor has penetrated through the prostate capsule it is called T3 and T4 if local invasion of a structure adjacent to the prostate is present. Those 4 major categories are subdivided (a, b or c) based on details from diagnostic tests. Thus an outcome for this variable is T1a, T1b, T1c (those are codified as 0), T2a, T2b (those are codified as 1) and T2c, T3a, T3b, T3c, T4a and T4b (those are codified as 2).

Prostatectomy Gleason grade refers to the degree of aggressiveness of a particular tumor based on the appearance of the tumor cells. Typically this is determined by microscopic analysis of the tissue from the tumor that has been extracted via prostatectomy. In general the grade is a number between 2 and 10. A higher Gleason grade indicates a poorly differentiated cancer, or more aggressive or more likely to spread. Thus the outcome for this variable is a number from 2 to 10. The numbers 2, 3, 4, 5, 6 (codified as 0), 7 (codified as 1), 8, 9, 10 (codified as 2).

Surgical oncologic margins refers to the presence or absence of tumor cells at the borders of surgically resected tumors. Typically this is determined by microscopic analysis of tumor tissues after prostatectomy. Thus the outcome for this variable is a No (Absence, codified as 0) or Yes (Presence, codified as 1).

Surgical gland margins refers to the presence or absence of tumor cells at the borders of prostatic gland. Typically this is determined by microscopic analysis of prostatic tissues after prostatectomy. Thus the outcome for this variable is a No (Absence, codified as 0) or Yes (Presence, codified as 1).

Table 18 shows which SNP variables and clinical variables are included in each of the four models for prognosing recurrence. As used herein, the "(model no.)" variables for a particular model are the SNP variables and clinical variables, selected from those in the first column of Table 18, which are included in the model, and which are informative for predicting the likelihood of recurrence occurring. For example, the "model 1 variables" are the SNP variables and clinical variables, selected from those in the first column of Table 18, which are included in model 1 and which are informative for prognosing the likelihood of recurrence (i.e. SNP46 and PSA).

For each of the variables included in each, Table 18 also indicates which outcome (SNP allele or clinical outcome) is associated with or suggestive of a poor prognosis.

Accordingly the invention in one aspect provides a method for determining the likelihood of PCa recurrence as described herein for a subject, comprising the step of determining or obtaining, for that subject, outcomes for one or more SNP variables and/or one or more clinical variables listed in Table 18 or Table 1B.

In one aspect the method is for predicting early PCa recurrence in a subject and comprises determining outcomes for the model 1 variables, and/or the model 2 variables and/or the model 3 variables, and/or the model 4 variables, listed in Table 18.

A method may comprise determining or obtaining outcomes for the model 1 variables (Table 18). Use of these variables allows discrimination of early PCa recurrence (defined as PSA>0.2 ng/ml) in a Spanish population with an LR+ of 2.7 (see Example 2 and FIG. 4). Details for the calculation of a probability function using these variables are given in Table 4.

A method may comprise determining or obtaining outcomes for the model 2 variables (Table 18). Use of these variables allows discrimination of early PCa recurrence (defined as PSA>0.4 ng/ml) in a Spanish population with an LR+ of 6.5 (see Example 2 and FIG. 5). Details for the calculation of a probability function using these variables are given in Table 5.

A method may comprise determining or obtaining outcomes for the model 3 variables (Table 18). Use of these variables allows discrimination of early PCa recurrence (defined as PSA>0.2 ng/ml) in a Spanish population with an LR+ of 5.7 (see Example 2 and FIG. 6). Details for the calculation of a probability function using these variables are given in Table 6.

A method may comprise determining or obtaining outcomes for the model 4 variables (Table 18). Use of these variables allows discrimination of early PCa recurrence (defined as PSA>0.4 ng/ml) in a Spanish population with an LR+ of 8.5 (see Example 2 and FIG. 7). Details for the calculation of a probability function using these variables are given in Table 7.

A method may comprise determining outcomes or obtaining for the variables of one or more of the present models 1 to 4. The method may comprise determining outcomes for variables of models which use post-operative variables (model 3 and/or model 4). The method may comprise determining outcomes for variables of models which determine risk of recurrence based on a recurrence PSA threshold of >0.4 ng/ml (model 2 and/or model 4).

In some aspects the present methods may include determining other factors for a subject. For example, the subject may be genotyped for one or more other genetic variations (such as other SNPs not listed in Table 18). These may be mutations associated with PCa or another condition. For example, a subject may be genotyped at one or more of the remaining SNPs listed in Table 1B, and/or at one or more of the remaining SNPs listed in Table 1A. Other markers (e.g. SNPs) associated with other diseases may also be determined.

The present methods may also be used in conjunction with or in addition to standard clinical tests. For example, the methods may be used in conjunction with or in addition to one or more nomograms aimed at predicting the probability of biochemical progression, e.g. based on clinical parameters such as PSA level, Gleason grade or clinical stage.

The present methods may be used together with clinical tests for PCa recurrence. As such the present methods may be used to confirm a clinical diagnosis of recurrence.

The present methods allow accurate prediction of PCa recurrence phenotypes based on a relatively small number of informative SNPs and clinical variables. This can be advantageous in that it allows use of genotyping techniques that would not necessarily be suitable for large scale SNP screening, as well as larger scale genotyping methods.

In general, even if a larger number of SNPs or genetic variations or factors are tested in the present methods, prediction of PCa recurrence can be made based only on outcomes of the variables listed for any one of the models in Table 18. These variables are sufficient for the prediction. Therefore in one example, the present methods allow differential prognosis of early recurrence of PCa or not, based on (at a maximum) the outcomes for the variables for any one or more of the models as in Table 18. The models may be used in combination as described herein.

In some instances though, it may be that some additional variables such as SNPs or other factors are used in the prediction. For example, in the present methods, prognosis may be made based on the outcomes of a maximum of 100, 90, 80, 70, 60, 50, 45, 40, 35, 30, 25, 20, 19, 18, 17, 16, 15, 14, 13, 12, 11, 10, 9, 8, 7, 6, 5, 4, 3, or 2 variables, such as SNPs or PCa associated SNPs. The SNPs may comprise (or consist of), or be selected from the Table 1B or Table 1A SNP variables.

In one aspect the method may involve genotyping a maximum of 100, 90, 80, 70, 60, 50, 40, 30, 25, 20, 19, 18, 17, 16, 15, 14, 13, 12, 11, 10, 9, 8, 7, 6, 5, 4, 3, or 2 SNPs or PCa-associated SNPs. The method may involve genotyping a maximum of (no more than) all the SNPs in Table 18, Table 1B or Table 1A. In some instances, the method comprises genotyping at a maximum, SNP variables for one or more of models 1 to 4, selected as described above.

Preferably the number and combination of variables such as SNPs used to construct a model for predicting recurrence according to the invention, is such that the model allows prediction to be made with an LR+ value of at least 2, such as at least 3, 4, 5, 6, 7, 8, 9, or 10. Calculation of LR+ values is described herein.

Once outcomes are determined for a test subject for each of the variables listed for a model, these outcomes are used in or inserted in a suitable probability function (for prediction of that phenotype), as described herein a probability function value may be calculated. Outcomes may be codified as described herein for use in the probability function and calculation of the probability function value. That probability function value can then be compared to probability function values obtained from a population of individuals of known, clinically determined phenotype (with respect to PCa recurrence, as described herein). Typically this may be done by comparison with a graph showing the distribution of values in the population. It can thus be determined whether a test individual is at high or low risk of recurrence based on the phenotypic group to which the test probability function value belongs.

A suitable probability function for determining a given phenotype may be derived by methods as set out in the present Examples and described herein. Typically a study population of individuals is provided. These individuals are of known (clinically determined) phenotype with respect to the phenotype that the probability function will be used to determine. In the present case, the phenotype is PCa recurrence (yes or no) within 5 years of prostatectomy. The PCa recurrence may be clinically determined as described herein. Where the probability function is to be derived from the model 1 or model 3 variables, PCa recurrence is generally established using a PSA threshold of >0.2 ng/ml. Where the probability function is to be derived from the model 2 or model 4 variables, PCa recurrence is generally established using a PSA threshold of >0.4 ng/ml.

Typically the individuals in the study population will be males who have been diagnosed with clinically localised PCa according to the criteria described herein. In general the males may be pre- or post-prostatectomy. Typically there will be at least 5 years follow up after surgery. In one example, the study population does not include patients who are receiving adjuvant therapy. The population may be for example, a Chinese, Japanese or a Caucasian male population, such as Spanish male population. Preferably the population used for deriving a probability function comprises a representative sample of the population in which the probability function will be applied.

In general at least n individuals are included in the study population. Typically n is 200-1000, for example 300, 400, 500 or 600. Where a probability function is for determining between alternative phenotypes, preferably there are approximately equal numbers of individuals with each of the alternative phenotypes in the population. Thus where there are two alternative phenotypes, A and B, the population is preferably approximately 50% phenotype A and 50% phenotype B. However, the ratios may be for example, 60/%40%, 70%/30%, 80/%20%, 90%/10% or any statistically acceptable distribution.

Each individual in the study population is then tested to determine outcomes for the particular variables on which the probability function is to be based. For example, these variables may be the variables listed for model 1, 2, 3, or 4 in Table 18. This provides a number of outcomes for each individual.

Multiple genotype-phenotype associations may then be analysed using stepwise multivariate logistic regression analysis, using as the dependent variable the clinically determined phenotype (PCa recurrence or not) and as independent variables the outcomes of the informative variables, e.g. as recommended by Balding D J. (2006[35]). The goodness of fit of the models obtained may be evaluated using Hosmer-Lemeshow statistics and their accuracy assessed by calculating the area under the curve (AUC) of the Receiver Operating Characteristic curve (ROC) with 95% confidence intervals (see, e.g. (Janssens A C J W et al., 2006[36]. Suitable methods are described in the Examples.

The sensitivity, specificity, and positive likelihood ratio (LR+=sensitivity/(1−specificity)) may be computed by means of ROC curves. Preferably the model obtained has an LR+ value of at least 2, for example, at least 3, 4, 5, 6, 7, 8, 9 or 10.

Mean probability function values for each of the alternative phenotypes in the population can be compared using a t test. In general the probability functions are able to distinguish between the different phenotypes in the study population in a statistically significant way, for example, at $p \leq 0.05$ in a t-test. Thus the probability functions produce a statistically significant separation between individuals of different phenotype in the population.

Statistical, analyses may be performed, for example, using the Statistical Package for the Social Sciences (SPSS Inc. Headquarters, Chicago, Ill., USA) version 14.0.

Probability function values can be calculated for each individual of known phenotype in the study population and plotted in a suitable graph.

In order to carry out the present methods of prognosis, a probability function value is calculated for the test individual, and this is compared with the probability function values for the individuals of known phenotype in the study population in order to determine the risk of a given phenotype in that individual. The comparison may be done by comparison with a graph or by any other suitable means known to those skilled in the art.

Thus in one aspect the invention further provides a method of deriving a probability function for use in predicting or determining early PCa recurrence as described herein, comprising:
(i) providing a study population of individuals, wherein each Individual is of known clinically determined phenotype with respect to PCa recurrence as described herein;
(ii) determining for each individual outcomes for each of a set of informative variables, thereby obtaining a set of outcomes for each individual;
(iii) applying stepwise multiple logistic regression analysis to the outcomes obtained in (ii) and the known phenotypes referred to in (i); and
(iv) thereby deriving a probability function which produces a statistically significant separation between individuals of different phenotype in the population;
wherein:
(a) the probability function is for prognosing early PCa recurrence according to the invention, and the set of variables for which outcomes are determined or obtained in step (ii) is selected from or consists of the model 1 variables listed in Table 18;
(b) the probability function is for prognosing early PCa recurrence according to the invention, and the set of variables for which outcomes are determined or obtained in step (ii) is selected from or consists of the model 2 variables listed in Table 18;
(c) the probability function is for prognosing early PCa recurrence according to the invention, and the set of variables for which outcomes are determined or obtained in step (ii) is selected from or consists of the model 3 variables listed in Table 18; and/or
(d) the probability function is for prognosing early PCa recurrence according to the invention, and the set of variables for which outcomes are determined or obtained in step (ii) is selected from or consists of the model 4 variables listed in Table 18.

Derivation of the probability functions may be carried out by a computer. Therefore in one aspect, the invention also relates to a computational method of deriving a probability function for use in prognosing PCa recurrence which method comprises applying stepwise multiple logistic regression analysis to outcomes data and phenotype data obtained from a suitable study population of individuals, wherein each individual is of known clinically determined phenotype with respect to PCa recurrence, thereby deriving a probability function which produces a statistically significant separation between individuals of different phenotype in the population; wherein:
(i) the phenotype data comprises the known clinically determined phenotype of each individual;
(ii) the outcomes data for each individual comprises outcomes for one or more single nucleotide polymorphism variables and one or more clinical variables listed in column 1 of Table 18;
and wherein:
(a) the probability function is for prognosing early PCa recurrence according to the invention, and the variables for which outcomes data is obtained (and referred to in (ii)) comprise or consist of the model 1 variables listed in Table 18;
(b) the probability function is for prognosing early PCa recurrence according to the invention, and the variables for which outcomes data is obtained (and referred to in (ii)) comprise or consist of the model 2 variables listed in Table 18;
(c) the probability function is for prognosing early PCa recurrence according to the invention, and the variables for which outcomes data is obtained (and referred to in (ii)) comprise or consist of the model 3 variables listed in Table 18; and/or
(d) the probability function is for prognosing early PCa recurrence according to the invention, and the variables for which outcomes data is obtained (and referred to in (ii)) comprise or consist of the model 4 variables listed in Table 18.

Suitable study populations and statistical analysis methods are described above. Reference may also be made to the present Examples.

Details for calculation of a probability function using the variables listed for each of models 1 to 4 are given in Tables 4 to 7 respectively. Statistical analyses may be performed, for example, using the Statistical Package for the Social Sciences (SPSS Inc. Headquarters, Chicago, Ill., USA) version 14.0. These may be used for calculation of probability function values for use in the methods herein. The probability functions may be used to determine a prognosis according to the invention.

In one aspect the invention relates to probability functions constructed or derived using the data in any of Tables 4 to 7, and to their use in a method, e.g. a computational method, for prognosing PCa recurrence. The invention further relates to associated computer programs and computer systems as described herein. The invention also relates to the probability functions derived according to the present methods and to their use in the methods described herein.

The invention also relates to the probability functions derived according to the present methods and to their use in the methods described herein.

The process of calculating a probability function value for a test subject and comparing the value to values obtained from a study population of individuals of known phenotypes in order to evaluate the risk of developing a phenotype in the test subject may also be carried out using appropriate software.

Therefore in one aspect the invention relates to a computational method for prognosing PCa recurrence using the outcomes of discriminating variables ("outcomes data") obtained according to the methods described herein (e.g. variables listed for any of models 1 to 4). In the computational method, outcomes data for the discriminating variables obtained from a test subject (test outcomes data) is inputted in a suitable probability function to produce a probability function value for the test subject. The test probability function value is then compared with probability function values for individuals of known phenotype (with respect to PCa recurrence as described herein) in order to prognose the likelihood of PCa recurrence in the test individual. The comparison may be made using the methods described herein.

The invention further relates to a computer system comprising a processor and means for controlling the processor to carry out a computational method described herein, and to a computer program comprising computer program code which when run on a computer or computer network causes the computer or computer network to carry out the computational method. In one aspect, the computer program is stored on a computer readable medium.

As described above and in the Examples, the present inventors have identified a number of single nucleotide polymorphisms (SNPs) which show single locus allelic association with poor PCa recurrence prognosis (likelihood of PCa recurrence, defined according to the 0.4 ng/ml threshold). The SNPs are listed in Table 1B and are SNPs 9. 24, 25, 28, 34, 46, 47, 51, 58 and 80. The single allele studies continued throughout the follow up, and therefore the association is with PCa recurrence at any time in the subject's lifetime.

As shown in FIGS. 8-17, particular genotypes at these SNPs are statistically significantly (P<0.05) associated with poor prognosis. These are: SNP 9 (TT); SNP 24 (GG); SNP 25 (CC); SNP 28 (AA); SNP 34 (AA); SNP 46 (GG); SNP 47 (GG); SNP 51 (AA); SNP 58 (TT); and SNP 80 (TT).

By identifying the nucleotide in the genomic DNA of a subject at one (or more) of these SNPs, it is possible to assess the risk or susceptibility of that individual to PCa recurrence during the individual's lifetime.

In one aspect the invention relates to the use of one or more of the SNPs in Table 1B in a method for prognosing PCa, in particular for determining the likelihood of PCa recurrence, e.g. within 5 years of surgery as described herein. Thus the invention in one aspect relates to a method for prognosing PCa recurrence (as described herein) comprising determining the genotype of an individual at one or more of the SNPs in Table 1B.

In general the present methods are carried out ex vivo or in vitro, e.g. using a sample obtained from the individual. A method may comprise use of the outcomes of clinical variables which have been obtained by the methods described herein.

Various methods are known in the art for determining the presence or absence in a test sample of a particular nucleic acid sequence, for example a nucleic acid sequence which has a particular nucleotide at a position of single nucleotide polymorphism. For example, genotype may be determined by microarray analysis, sequencing, primer extension, ligation of allele specific oligonucleotides, mass determination of primer extension products, restriction length polymorphism analysis, single strand conformational polymorphism analysis, pyrosequencing, dHPLC or denaturing gradient gel electrophoresis (DGGE). Furthermore, having sequenced nucleic acid of an individual or sample, the sequence information can be retained and subsequently searched without recourse to the original nucleic acid itself. Thus, for example, a sequence alteration or mutation may be identified by scanning a database of sequence information using a computer or other electronic means.

In general, a sample is provided, containing nucleic acid which comprises at least one of the genetic variations to be tested. The nucleic acid comprises one or more target regions comprising the genetic variation(s) (SNPs) which are to be characterised.

The nucleic acid may be obtained from any appropriate biological sample which contains nucleic acid. The sample may be taken from a fluid or tissue, secretion, cell or cell line derived from the human body.

For example, samples may be taken from blood, including serum, lymphocytes, lymphoblastoid cells, fibroblasts, platelets, mononuclear cells or other blood cells, from saliva, liver, kidney, pancreas or heart, urine or from any other tissue, fluid, cell or cell line derived from the human body. For example, a suitable sample may be a sample of cells from the buccal cavity.

Preferably nucleic acid is obtained from a blood sample.

In general, nucleic acid is extracted from the biological sample using conventional techniques. The nucleic acid to be extracted from the biological sample may be DNA, or RNA, typically total RNA. Typically RNA is extracted if the genetic variation to be studied is situated in the coding sequence of a gene. Where RNA is extracted from the biological sample, the methods may further comprise a step of obtaining cDNA from the RNA. This may be carried out using conventional methods, such as reverse transcription using suitable primers. Subsequent procedures are then typically carried out on the extracted DNA or the cDNA obtained from extracted RNA. The term DNA, as used herein, may include both DNA and cDNA.

In general the genetic variations to be tested are known and characterised, e.g. in terms of sequence. Therefore nucleic acid regions comprising the genetic variations may be obtained using methods known in the art.

In one aspect, DNA regions which contain the genetic variations (SNPS) to be identified (target regions) are subjected to an amplification reaction in order to obtain amplification products which contain the genetic variations to be identified. Any suitable technique or method may be used for amplification.

For example, the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)) may be used. The nucleic acid used as template in the amplification reaction may be genomic DNA, cDNA or RNA.

Other specific nucleic acid amplification techniques include strand displacement activation, the QB replicase system, the repair chain reaction, the ligase chain reaction, rolling circle amplification and ligation activated transcription.

Allele-specific oligonucleotides may be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the polymorphism on a denaturing polyacrylamide DNA sequencing gel, with specific bands that are linked to the gene variants being selected.

Those skilled in the art are well versed in the design of primers for use in processes such as PCR. Various techniques for synthesizing oligonucleotide primers are well known in the art, including phosphotriester and phosphodiester synthesis methods.

A further aspect of the present invention provides a pair of oligonucleotide amplification primers suitable for use in the methods described herein.

PCR primers suitable for amplification of target DNA regions comprising the SNPs in Table 1A are listed in Table 3A and Table 3B. The present methods may comprise the use of one or more of these primers or one or more of the listed primer pairs, according to the SNPs to be genotyped, wherein these SNPs are selected as described herein. In one aspect the method comprises use of all of the primers listed in Tables 3A and 3B. Suitable reaction conditions may be determined using the knowledge in the art.

The amplified nucleic acid may then be sequenced and/or tested in any other way to determine the presence or absence of a particular feature. Nucleic acid for testing may be prepared from nucleic acid removed from cells or in a library using a variety of other techniques such as restriction enzyme digest and electrophoresis.

For example, the allele of the at least one polymorphism (i.e. the identity of the nucleotide at the position of single nucleotide polymorphism) may be determined by determining the binding of an oligonucleotide probe to the amplified region of the genomic sample. A suitable oligonucleotide probe comprises a nucleotide sequence which binds specifically to a particular allele of the at least one polymorphism and does not bind specifically to other alleles of the at least one polymorphism. Such a probe may correspond in sequence to a region of genomic nucleic acid, or its complement, which contains one or more of the SNPs described herein. Under suitably stringent conditions, specific hybridisation of such a probe to test nucleic acid is indicative of the presence of the sequence alteration in the test nucleic acid. For efficient screening purposes, more than one probe may be used on the same test sample.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridization overnight at 42° C. in 6×SSC and washing in 6×SSC at a series of increasing temperatures from 42° C. to 65° C.

Other suitable conditions and protocols are described in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

A further aspect of the present invention provides an oligonucleotide which hybridises specifically to a nucleic acid sequence which comprises a particular allele of a polymorphism selected from the group consisting of the single nucleotide polymorphisms shown in Table 1A, 1B or Table 18, and does not bind specifically to other alleles of the SNP. Hybridisation may be determined under suitable selective hybridisation conditions as described herein.

Such oligonucleotides may be used in a method of screening nucleic acid.

In some preferred embodiments, oligonucleotides according to the present invention are at least about 10 nucleotides in length, more preferably at least about 15 nucleotides in length, more preferably at least about 20 nucleotides in length. Oligonucleotides may be up to about 100 nucleotides in length, more preferably up to about 50 nucleotides in length, more preferably up to about 30 nucleotides in length. The boundary value 'about X nucleotides' as used above includes the boundary value 'X nucleotides'. Oligonucleotides which specifically hybridise to particular alleles of the SNPs listed in Table 1A are listed in Table 2 and are described herein.

Where the nucleic acid is double-stranded DNA, hybridisation will generally be preceded by denaturation to produce single-stranded DNA. The hybridisation may be as part of an amplification, e.g. PCR procedure, or as part of a probing procedure not involving amplification. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mismatch between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid.

Nucleic acid in a test sample, which may be a genomic sample or an amplified region thereof, may be sequenced to identify or determine the identity of a polymorphic, allele. The allele of the SNP in the test nucleic acid can therefore be compared with the susceptibility alleles of the SNP as described herein to determine whether the test nucleic acid contains one or more alleles which are associated with disease.

Typically in sequencing, primers complementary to the target sequence are designed so that they are a suitable distance (e.g. 50-400 nucleotides) from the polymorphism. Sequencing is then carried out using conventional techniques. For example, primers may be designed using software that aims to select sequence(s) within an appropriate window which have suitable Tm values and do not possess secondary structure or that will hybridise to non-target sequence.

Sequencing of an amplified product may involve precipitation with isopropanol, resuspension and sequencing using a TaqFS+ Dye terminator sequencing kit. Extension products may be electrophoresed on an ABI 377 DNA sequencer and data analysed using Sequence Navigator software.

Genotype analysis may be carried out by microarray analysis. Any suitable microarray technology may be used. The methodology reported in Tejedor et al 2005 (Clinical Chemistry, 51: 1137-1144) including the MG 1.0 software, and in International Patent Application No. PCT/IB2006/00796 filed 12 Jan. 2006 (the contents of which are hereby incorporated by reference) may be used. This technology uses a low-density DNA array and hybridisation to allele-specific oligonucleotide probes to screen for SNPs. Thus in one aspect the ProScan microarray and technology of the present invention may be used to determine the genotype of the informative SNPs as described herein.

Once a subject has received a prognosis of aggressive PCa (a significant risk of PCa recurrence according to the invention), the most appropriate treatment for that subject can be selected. In this way, the invention allows better targeting of therapies to patients.

Thus in a further aspect, the invention provides a method of selecting a suitable treatment for a subject diagnosed as having localised PCa, the method comprising:
(a) determining the likelihood of PCa recurrence post-surgery in the subject by a method described herein; and
(b) selecting a suitable treatment.

The selected treatment may then be administered to the subject. Thus the invention also relates to a method of treating localised PCa in a subject comprising:
(a) determining the likelihood of PCa recurrence post-surgery in the subject by a method described herein; and
(b) treating the subject with a suitable treatment.

For example, where risk of recurrence is determined for a pre-operative subject, this may be used to determine whether surgery is required or desirable, or to select another local therapy. Where recurrence is determined for a post-operative subject, this will help to assess whether an adjuvant therapy, e.g radiation or chemotherapy, is required or advisable.

Means for carrying out the present prognostic methods may be provided in kit form e.g. in a suitable container such as a vial in which the contents are protected from the external environment. Therefore in one aspect the invention further relates to prognostic kits suitable for use in the methods described herein. Typically a kit comprises:
(i) means for determining outcomes for the selected variable(s) or SNP variables; and
(ii) instructions for determining prognosis based on the outcomes of the variables.

The means (i) may comprise one or more oligonucleotide probes suitable for detection of one or more SNP variables to be determined. For example, the means (i) may comprise one or more probe pairs or probe sets listed in Table 2. In one instance the kit may comprise all of the probe sets in Table 2.

The means (i) may comprise a suitable microarray, as described herein. The means (i) may comprise one or more pairs of sequencing primers suitable for sequencing one or more of the SNP variables to be determined.

The instructions (ii) typically comprise instructions to use the outcomes determined using the means (i) for the prognosis. The instructions may comprise a chart showing risks of PCa recurrence. The kit may include details of probability functions which may be used in prognosis, such as those described herein.

A kit may in some cases include a computer program as described herein.

A kit may include other components suitable for use in the present methods. For example, a kit may include primers suitable for amplification of target DNA regions containing the SNPs to be determined, such as those described herein. For example, a kit may contain one or more primer pairs listed in Tables 3A & 3B. A kit may also include suitable labelling and detection means, controls and/or other reagents such as buffers, nucleotides or enzymes e.g. polymerase, nuclease, transferase.

Nucleic acid according to the present invention, such as an oligonucleotide probe and/or pair of amplification primers, may be provided as part of a kit. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled.

A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

In a further aspect the present invention also relates to DNA chips or microarrays and methods for their use, which allow reliable genotyping of individuals with respect to multiple PCa associated genetic variations simultaneously and for clinical purposes.

Thus in one aspect, the invention further provides a method of genotyping PCa associated genetic variations in an individual, which is sufficiently sensitive, specific and reproducible for clinical use. The inventors have developed low density DNA-microarrays with specifically designed probes for use in the method, and a computational method or algorithm for interpreting and processing the data generated by the arrays.

In one aspect, the invention relates to an in vitro method for genotyping PCa associated genetic variations in an individual. The method allows simultaneous genotyping of multiple human genetic variations present in one or more genes of a subject. The method of the invention allows identification of nucleotide changes, such as, insertions, duplications and deletions and the determination of the genotype of a subject for a given genetic variation.

Genetic variation or genetic variant refers to mutations, polymorphisms or allelic variants. A variation or genetic variant is found amongst individuals within the population and amongst populations within the species.

A PCa associated genetic variation may refer to a genetic variation that is associated with PCa in a statistically significant way and that can be used as an aid in the diagnosis, prognosis or prediction of response to therapy in an individual.

Polymorphism refers to a variation in the sequence of nucleotides of nucleic acid where every possible sequence is present in a proportion of equal to or greater than 1% of a population; in a particular case, when the said variation occurs in just one nucleotide (A, C, T or G) it is called a single nucleotide polymorphism (SNP).

Genetic mutation refers to a variation in the sequence of nucleotides in a nucleic acid where every possible sequence is present in less than 1% of a population Allelic variant or allele refers to a polymorphism that appears in the same locus in the same population.

Thus a genetic variation may comprise a deletion, substitution or insertion of one or more nucleotides. In one aspect the genetic variations to be genotyped according to the present methods comprise SNPs.

A given gene may comprise one or more genetic variations. Thus the present methods may be used for genotyping of one or more genetic variations in one or more genes.

Typically the individual is a human.

Typically, for a given genetic variation there are three possible genotypes:
AA the individual is homozygous for genetic variation A (e.g. homozygous for a wild type allele)
BB the individual is homozygous for genetic variation B (e.g. homozygous for a mutant allele)
AB the individual is heterozygous for genetic variations A and B (e.g. one wild type and one mutant allele)

The genetic variations, such as SNPs, to be analysed according to the present methods, are associated with PCa.

Examples of genetic variations associated with PCa which may be assessed by the present methods include those in Table 1A (FIG. 1A).

The sequences of all the genes mentioned in Table 1A are known and recognized on the following websites: GeneBank (NCBI), GeneCard (Weizmann Institute of Sciences) and Snpper.chip.org (Innate Immunity PGA). RefSNP codes (rs#) for each SNP are taken from the Single Nucleotide Polymorphism Database (dbSNP) curated by the National Center for Biotechnology Information (NCBI) as found at ncbi.nlm.nih.gov/entrez/query.fcgi?CMD=search&DB=snp, as at 4 Jul. 2007).

By permitting clinical genotyping of one or more of the above genetic variations, the present method has use in for example, diagnosing susceptibility to or the presence of PCa in a subject. The present genotyping methods are also be useful in prognosing PCa phenotypes, as described herein.

At least one PCa associated genetic variation, e.g. SNP, is analysed in the present genotyping methods. The present methods allow simultaneous genotyping of multiple variations in an individual and typically multiple variations are analysed, in general, at least 10, 12, 14, 16, 18 or 20 PCa associated genetic variations. For example, at least 25, 30, 35, 40, 45, 50, 55, 60, 65, 70, 75, 80, 85, 90, 95, 100, 105 or 110 variations or up to 150, 200, 300, 400, 500, or 600 variations may be tested, such as 250, 350 or 450 variations.

Thus the genotyping methods may be used for genotyping an individual with respect to all of or a selection of the variations in Table 1A, as described herein. For example, at least 1, 2, 3, 4, 5, 10, 15, 20, 25, 10, 35, 40, 45, 50, 55, 60, 65, 70, 75, 80, 85 or all of the Table 1 variations may be genotyped. The variations to be detected may additionally include other PCa associated genetic variations.

The present invention also encompasses methods in which other genetic variations are assessed in addition to the PCa associated genetic variations.

According to the present methods, a sample is provided, containing nucleic acid which comprises at least one of the genetic variations to be tested (the target DNA). Suitable samples and methods for obtaining the samples are described herein in relation to the prognostic methods.

As described, DNA regions which contain the genetic variations to be identified (target DNA regions) may be subjected to an amplification reaction in order to obtain amplification products which contain the genetic variations to be identified. Any suitable technique or method may be used for amplification. In general, the technique allows the (simultaneous) amplification of all the DNA sequences containing the genetic variations to be identified. In other words, where multiple genetic variations are to be analysed, it is preferable to simultaneously amplify all of the corresponding target DNA regions (comprising the variations). Carrying out the amplification in a single step (or as few steps as possible) simplifies the method.

For example, multiplex PCR may be carried out, using appropriate pairs of oligonucleotide PCR primers which are capable of amplifying the target regions containing the genetic variations to be identified. Any suitable pair of primers which allow specific amplification of a target DNA region may be used. In one aspect, the primers allow amplification in the least possible number of PCR reactions. Thus, by using appropriate pairs of oligonucleotide primers and appropriate conditions, all of the target DNA regions necessary for genotyping the genetic variations can be amplified for genotyping (e.g. DNA-chip) analysis with the minimum number of reactions. Suitable PCR primers for amplification of target DNA regions comprising the PCa-associated genetic variations in Table 1A are listed in Tables 3A & 3B. The present method may comprise the use of one or more of these primers or one or more of the listed primer pairs. For example, the present methods may be used for genotyping of Table 1A variations selected as described above. The corresponding primers in Table 3A & 3B may be selected for use accordingly.

In one instance, the amplification products can be labelled during the amplification reaction with a detectable label. The aim is to be able to later detect hybridisation between the fragments of target DNA containing the genetic variations being analysed and probes fixed on a solid support. The greater the extent of hybridisation of labelled target DNA to a probe, the greater the intensity of detectable label at that probe position.

The amplification products may be labelled by conventional methods. For example, a labelled nucleotide may be incorporated during the amplification reaction or labelled primers may be used for amplification.

Labelling may be direct using for example, fluorescent or radioactive markers or any other marker known by persons skilled in the art. Examples of fluorophores which can be used, include for example, Cy3 or Cy5. Alternatively enzymes may be used for sample labelling, for example alkaline phosphatase or peroxidase. Examples of radioactive isotopes which can be used include for example $^{33}P$, $^{125}I$, or any other marker known by persons skilled in the art. In one instance, labelling of amplification products is carried out using a nucleotide which has been labelled directly or indirectly with one or more fluorophores. In another example, labelling of amplification products is carried out using primers labelled directly or indirectly with one or more fluorophores.

Labelling may also be indirect, using, for example, chemical or enzymatic methods. For example, an amplification product may incorporate one member of a specific binding pair, for example avidin or streptavidin, conjugated with a fluorescent marker and the probe to which it will hybridise may be joined to the other member of the specific binding pair, for example biotin (indicator), allowing the probe/target binding signal to be measured by fluorimetry. In another example, an amplification product may incorporate one member of a specific binding pair, for example, an anti-dioxigenin antibody combined with an enzyme (marker) and the probe to which it will hybridise may be joined to the other member of the specific binding pair, for example dioxigenin (indicator). On hybridization of amplification product to probe the enzyme substrate is converted into a luminous or fluorescent product and the signal can be read by, for example, chemiluminescence or fluorometry.

The nucleic acid comprising the genetic variation(s) to be tested, e.g. the (optionally labelled) amplification products, may further undergo a fragmentation reaction, thereby obtaining some fragmentation products which comprise or contain the genetic variations to be identified or analysed. Typically fragmentation increases the efficiency of the hybridisation reaction. Fragmentation may be carried out by any suitable method known in the art, for example, by contacting the nucleic acid, e.g. the amplification products with a suitable enzyme such as a DNase.

If the nucleic acid has not been previously labelled; e.g. during the amplification reaction, (and, typically, where no posthybridisation amplification or ligation is carried out on the solid support) then labelling with a detectable label may be carried out prehybridisation by labelling the fragmentation products. Suitable labelling techniques are known in the art and may be direct or indirect as described herein. Direct labelling may comprise the use of, for example, fluorophores, enzymes or radioactive isotopes. Indirect labelling may comprise the use of, for example, specific binding pairs that incorporate e.g. fluorophores, enzymes, etc. For example, if amplification products have not been labelled during the amplification reaction the fragmentation products may undergo a direct or indirect labelling with one or various markers, for example one or various fluorophores, although other known markers can be used by those skilled in the art.

According to the present methods the nucleic acid, e.g. the amplification or fragmentation products, comprising the genetic variation(s) to be detected (target DNA), is contacted with oligonucleotide probes which are capable of detecting the corresponding genetic variations by hybridisation under suitable conditions.

Typically the hybridisation conditions allow specific hybridisation between probes and corresponding target nucleic acids to form specific probe/target hybridisation complexes while minimising hybridisation between probes carrying one or more mismatches to the DNA. Such conditions may be determined empirically, for example by varying the time and/or temperature of hybridisation and/or the number and stringency of the array washing steps that are performed following hybridisation and are designed to eliminate all probe-DNA interactions that are inspecific.

In the method, the probes are provided deposited on a solid support or surface. The probes are deposited at positions on the solid support according to a predetermined pattern, forming a "DNA-chip". It has been found that the chips should comply with a number of requirements in order to be used in the present methods, for example in terms of the design of the probes, the number of probes provided for each genetic variation to be detected and the distribution of probes on the support. These are described in detail herein. The inventors have developed suitable genotyping chips for use in the present methods and accordingly in one aspect the invention provides a DNA-chip or (micro)array comprising a plurality of probes deposited or immobilised on a solid support as described herein.

In general the solid support or phase comprises oligonucleotide probes suitable for detection of each genetic variation to be tested in the present method. The number and type of genetic variations to be tested using a chip may be selected as described herein.

Typically there will be at least one probe which is capable of hybridising specifically to genetic variation A (e.g. a wild-type or normal allele) (probe 1) and one probe which is capable of hybridising specifically to genetic variation B (e.g. a mutant allele) (probe 2) under the selected hybridisation conditions. These probes form a probe pair. Probe 1 is for detection of genetic variation A and probe 2 for detection of genetic variation B. Typically the probes can be used to discriminate between A and B (e.g. the wildtype and mutant alleles).

The probes may examine either the sense or the antisense strand. Typically, probes 1 and 2 examine the same nucleic acid strand (e.g. the sense strand or antisense strand) although in some cases the probes may examine different strands. In one aspect probes 1 and 2 have the same sequence except for the site of the genetic variation.

In one instance, the probes in a probe pair have the same length. In some aspects, where two or more pairs of probes are provided for analysis of a genetic variation, the probes may all have the same length.

Preferably more than one probe pair is provided for detection of each genetic variation. Thus, at least 2, 3, 4, 5, 6, 7, 8, 9, 10 or more probe pairs may be provided per genetic variation. In one aspect, (at least) 2 probe pairs are provided. The aim is to reduce the rate of false positives and negatives in the present methods.

For example, for a given genetic variation there may be:
Probe 1 which is capable of hybridising to genetic variation A (e.g. a normal allele)
Probe 2 which is capable of hybridising to genetic variation B (e.g. a mutant allele)
Probe 3 which is capable of hybridising to genetic variation A (e.g. a normal allele)
Probe 4 which is capable of hybridising to genetic variation B (e.g. a mutant allele).

The probes may examine the same or different strands. Thus in one embodiment, probes 3 and 4 are the complementary probes of probes 1 and 2 respectively and are designed to examine the complementary strand. In one aspect it is preferred that the probes provided for detection of each genetic variation examine both strands.

More than 2 pairs of probes may be provided for analysis of a genetic variation as above. For example, where a genetic variation exists as any one of 4 bases in the same strand (e.g. there are three mutant possibilities), at least one pair of probes may be provided to detect each possibility. Preferably, at least 2 pairs of probes are provided for each possibility.

Thus, for example, for an SNP G2677T/A/C, at least one pair of probes may be provided for detection of G2677T, one pair for detection of G2677/A, and one pair for detection of G2677C. Preferably at least two pairs of probes are provided for each of these substitutions.

A number of methods are known in the art for designing oligonucleotide probes suitable for use in DNA-chips.

A "standard tiling" method may be used. In this method, 4 oligonucleotides are designed that are totally complementary to the reference sequence except in the central position where, typically the 4 possible nucleotides A, C, G and T are examined. An illustrative example of this strategy is the DNA-chip for genotyping of HIV-1 (Affymetrix).

In "alternative tiling" 5 oligonucleotides are designed, so that the fifth examines a possible deletion in the sequence. An example of this strategy is the DNA-chip to detect mutations in p53 (Affymetrix).

In "block tiling" 4 oligonucleotides are designed that are totally complementary to the normal sequence and another 4 totally complementary to the mutant sequence. The nucleotide which changes is placed in the central position, but a mismatch of one of the 4 bases (A, C, T or G) is placed 2 nucleotides before or after the nucleotide position that it is wished to interrogate. An example of this strategy is the DNA-chip for the detection of mutations in cytochrome p450 (Roche and Affymetrix).

A further example is "alternative block tiling" where the "mismatch" is used to increase the specificity of the hybrid not only in one position but also in the positions −4, −1, 0, +1 and +4 to identify the change produced in the central position or 0. An example is the DNA-chip to detect 1,500 SNPs (Affymetrix).

Any one or more of these strategies may be used to design probes for the present invention. Preferably standard tiling is used, in particular with 2 pairs of probes e.g. 2 pairs of complementary probes as above. Thus it is preferable that the oligonucleotide sequence is complementary to the target DNA or sequence in the regions flanking the variable nucleotide(s). However, in some cases, one or more mismatches may be introduced, as described above.

The oligonucleotide probes for use in the present invention typically present the base to be examined (the site of the genetic variation) at the centre of the oligonucleotide. This is particularly the case where differential hybridisation methods are used, as in general this allows the best discrimination between matched and mismatched probes. In these methods, typically there is formation of specific detectable hybridisation complexes without post-hybridisation on-chip amplification. For example, for precise (single base) mutations, the base which differs between the normal and the mutant allele is typically placed in the central position of the probe. In the case of insertions, deletions and duplications, the first nucleotide which differs between the normal and the mutant sequence is placed in the central position. It is believed that placing the mutation at the centre of the probe maximises specificity.

Where post-hybridisation on-chip amplification (e.g. ligation or primer extension methods) is employed, oligonucleotide probes typically present the variable base(s) at the 3' end of the probe. Where OLA methodology is used, oligonucleotides (labelled directly or indirectly) are also designed which hybridise to probe-target complexes to allow ligation.

In general the probes for use in the present invention comprise or in some embodiments consist (essentially) of 17 to 27 nucleotides, for example, 19, 21, 23, or 25 nucleotides or 18, 20, 22, 24 or 26 nucleotides.

Preferably the individual probes provided for detection of a genetic variation are capable of hybridising specifically to the normal and mutant alleles respectively under the selected hybridisation conditions. For example, the melting temperature of the probe/target complexes may occur at 75-85° C. and hybridisation may be for one hour, although higher and lower temperatures and longer or shorter hybridisations may also suffice.

The probes provided for (suitable for) detection of each genetic variation (as described above) are typically capable of discriminating between genetic variation A and B (e.g. the normal and mutant alleles) under the given hybridisation conditions as above. Preferably the discrimination capacity of the probes is substantially 100%. If the discrimination capacity is not 100%, the probes are preferably redesigned. Preferably the melting temperature of the probe/target complexes occurs at 75-85 degrees C. Methods for testing discrimination capacity are described herein.

In one example, the probes provided for detection of a genetic variation examine both strands and have lengths ranging from 19-27 nucleotides. Preferably the probes have 100% discrimination capacity and the melting temperature of probe/target complexes is 75-85 degrees C.

Typically in order to obtain probes for use in the present methods, a number of probes are designed and tested experimentally for, e.g. hybridisation specificity and ability to discriminate between genetic variants (e.g. a normal and a mutant allele). Candidate oligonucleotide probe sequences may be designed as described above. These may vary for example in length, strand specificity, position of the genetic variation and degree of complementarity to the sequence flanking the genetic variation in the target DNA. Once probe pairs have been designed, these can be tested for hybridisation specificity and discrimination capacity. The capacity of specific probes to discriminate between the genetic variations A and B (e.g. normal and mutant alleles) depends on hybridisation conditions, the sequence flanking the mutation and the secondary structure of the sequence in the region of the mutation. By using stable hybridisation conditions, appropriate parameters such as strand specificities and lengths can be established in order to maximise discrimination. Preferably, the genetic variation is maintained at the central position in the tested probes.

Methods for testing discrimination capacity of probes are described herein. Typically a number of candidate probe pairs are provided and used in a training method as described below. In general two pairs of probes (probes 1 and 2, and probes 3 and 4) are tested in the method. For example, two pairs of probes examining both strands (complementary to each other) may be tested. If it is not possible to obtain 100% discrimination between the three genotyping groups using the probes, the probes are typically redesigned. Hybridisation conditions in the training method are generally maintained stably. Typically the melting temperature of probe/target complexes is 75-85° C.

For example, starting from probes of 25 nucleotides which detect a genetic variation (e.g. the normal allele) and another genetic variation (e.g. a mutant allele) in both strands (sense and antisense), in general an average of 8 probes may be experimentally tested to identify two definite pairs.

Probes are chosen to have maximum hybridisation specificity and discrimination capacity between genetic variants (e.g. a normal and a mutant allele) under suitable hybridisation conditions. For example, the probes for detection of a given genetic variation, e.g. two probe pairs, typically have substantially 100% discrimination capacity. Typically the melting temperature of probe/target complexes is at 75-85° C.

Using the methods herein the inventors have developed oligonucleotide probes suitable for detection of the PCa-associated genetic variations in Table 1A. These probes are presented as SEQ ID NOS 1-360 (Table 2). The probes are listed in probe sets (90 sets in total), according to the genetic variation to be detected. At least two pairs of probes are listed in each set.

In one aspect the invention relates to any one or more of the oligonucleotide probes, pairs of probes or sets of probes set out in SEQ ID NOS 1-360 (Table 2), and to their use in the genotyping, diagnostic or therapeutic methods of the invention. The invention further relates to any one or more of the oligonucleotide probes, pairs of probes or sets of probes set out in SEQ ID NOS 1-360 for use in medicine, for example in a diagnostic or therapeutic method described herein. A chip of the invention may comprise one or more of the listed probe pairs or sets as described herein.

In general probes are provided on the support in replicate. Typically, at least 4, 6, 8, 10, 12, 14, 16, 18 or 20 replicates are provided of each probe, in particular, 6, 8 or 10 replicates. Thus for example, the support (or DNA-chip) may comprise or include 10 replicates for each of (at least) 4 probes used to detect each genetic variation (i.e. 40 probes). Alternatively the support (or DNA-chip) may comprise or include 8 replicates for each of (at least) 4 probes used to detect each genetic variation (i.e. 32 probes). Still further the support (or DNA-chip) may comprise or include 6 replicates for each of (at least) 4 probes used to detect each genetic variation (i.e. 24 probes). Using probe replicates helps to minimise distortions in data interpretation from the chip and improves reliability of the methods.

In general the support also comprises one or more control oligonucleotide probes. These are also provided in replicate as above. Thus the support (or DNA-chip) may additionally comprise one or more oligonucleotides deposited on the support which are useful as positive and/or negative controls of the hybridisation reactions. If post-hybridisation amplification or ligation reactions are carried out on the chip, there may also be one or more positive or negative controls of these reactions.

Typically the chip or array will include positive control probes, e.g., probes known to be complementary and hybridisable to sequences in the target polynucleotide molecules, probes known to hybridise to an external control DNA, and negative control probes, e.g., probes known to not be complementary and hybridizable to sequences in the target polynucleotide molecules. The chip may have one or more controls specific for each target, for example, 2, 3, or more controls. There may also be at least one control for the array.

Positive controls may for example be synthesized along the perimeter of the array or in diagonal stripes across the array. The reverse complement for each probe may be synthesized next to the position of the probe to serve as a negative control. In yet another example, sequences from other species of organism may be used as negative controls in order to help determine background (non-specific) hybridisation.

As above, the support (or DNA-chip) may include some (one or more) oligonucleotides deposited on the support which are useful as positive and negative controls of the hybridization reactions. In general, each one of the sub-arrays, for example 16, which typically constitute a DNA-chip, is flanked by some external hybridization controls, which serve as reference points allowing allow the points within the grid to be located more easily.

In one instance, the nucleotide sequence of an external control DNA is the following (5'→3):

```
CEH:                                            (SEQ ID NO: 539)
GTCGTCAAGATGCTACCGTTCAGGAGTCGTCAAGATGCTACCGTTCAGGA
``` and the sequences of the oligonucleotides for its detection are the following:

```
ON1:    CTTGACGACTCCTGAACGG      (SEQ ID NO: 540)

ON2:    CTTGACGACACCTGAACGG      (SEQ ID NO: 541)
```

Positive control probes are generally designed to hybridise equally to all target DNA samples and provide a reference signal intensity against which hybridisation of the target DNA (sample) to the test probes can be compared. Negative controls comprise either "blanks" where only solvent (DMSO) has been applied to the support or control oligonucleotides that have been selected to show no, or only minimal, hybridisation to the target, e.g. human, DNA (the test DNA). The intensity of any signal detected at either blank or negative control oligonucleotide features is an indication of non-specific interactions between the sample DNA and the array and is thus a measure of the background signal against which the signal from real probe-sample interactions must be discriminated.

Desirably, the number of sequences in the array will be such that where the number of nucleic acids suitable for detection of genetic variations is n, the number of positive and negative control nucleic acids is n', where n' is typically from 0.01 to 0.4n.

In general, the support or chip is suitable for genotyping PCa associated genetic variations, in particular, genotyping according to the present methods. The chip typically comprises probes suitable for detection of at least one but preferably multiple, PCa associated genetic variation(s), typically at least 10, 12, 14, 16, 18 or 20 variations. For example, at least 25, 30, 35, 40, 45, 50, 55, 60, 65, 70, 75, 80, 85, 90, 95, 100, 105 or 110 variations or up to 150, 200, 300, 400, 500, or 600 variations may be tested, such as 250, 350 or 450 variations.

The PCa associated genetic variations may include any or all of those in Table 1A. Thus an array or chip may comprise probes suitable for genotyping an individual with respect to all of the variations in Table 1A, or a selection of the variations in the Table, as described herein.

A DNA-chip according to the invention ('Proscan') allows simultaneous, sensitive, specific and reproducible genotyping of genetic variations associated with PCa. Non-limiting examples of such variations are given in Table 1A. Nevertheless, the number of genetic variations contained in the Table can be increased as other genetic variations are subsequently identified and are associated with PCa. Thus the genetic variations detectable by the chip may comprise, or consist (essentially) of those listed in Table 1A or Table 1B or FIG. 18 or a selection of these, as described in relation to the present methods. The chip will comprise probes suitable for detection of these genetic variations as described herein. Preferably where a chip comprises probes for detection of a genetic variation in Table 1A the chip comprises one or more of the probes listed in SEQ ID NOS 1-360 (Table 2) as suitable for detection of that genetic variation, e.g. the probes set listed in SEQ ID NOs 1-360 for detection of that variation. In one aspect the present chip comprises one or more probes selected from those in SEQ ID NOS 1-360. The probes are listed in probe sets, according to the genetic variation to be detected. At least two pairs of probes are provided in each set. A chip may comprise at least one probe pair or at least one probe set, or a selection of the probe sets, for example a probe pair or a probe set from at least 5, 10, 15, 20, 25, 30, 35, 40, 45, 50, 55, 60, 65, 70, 75, 80, 85 or all 90 sets, according to the genetic variations being tested. A chip may comprise other probes for detection of variations in Table 1A or other variations associated with PCa instead of or in addition to those specifically listed.

Proscan may additionally comprise oligonucleotide probes for detection of genetic variations not associated with PCa. For example, the chips may comprise probes for detection of genetic variations such as SNPs associated with another (related) condition such as colon, rectal or bladder cancer. Typically, in Proscan, the number of nucleic acids suitable for detection of genetic variations associated with PCa (e.g. those in Table 1A or Table 1B or FIG. 18) represent at least 50%, 60%, 70%, 75%, 80%, 85%, 90%, 95%, 97%, 98%, 99% or more of the nucleic acids in the array.

In general the support or chip has from 300 to 40000 nucleic acids (probes), for example, from 400 to 30000 or 400 to 20000. The chip may have from 1000 to 20000 probes, such as 1000 to 15000 or 1000 to 10000, or 1000 to 5000. A suitable chip may have from 2000 to 20000, 2000 to 10000 or 2000 to 5000 probes. For example, a chip may have 1000, 2000, 3000, 4000, 5000, 6000, 7000, 8000, 9000, 10000, 12000, 14000, 16000, 18000 or 20000 probes. Smaller chips 400 to 1000 probes, such as 400, 500, 600, 700, 800, 900 or 950 probes are also envisaged.

In general the array or chip of the invention comprises a support or surface with an ordered array of binding (e.g. hybridisation) sites or probes. Thus the arrangement of probes on the support is predetermined. Each probe (i.e. each probe replicate) is located at a known predetermined position on the solid support such that the identity (i.e. the sequence) of each probe can be determined from its position in the array. Typically the probes are uniformly distributed in a predetermined pattern.

Preferably, the probes deposited on the support, although they maintain a predetermined arrangement, are not grouped by genetic variation but have a random distribution. Typically they are also not grouped within the same genetic variation. If desired, this random distribution can be always the same. Therefore, typically the probes are deposited on the solid support (in an array) following a predetermined pattern so that they are uniformly distributed, for example, between the two areas that may constitute a DNA-chip, but not grouped according to the genetic variation to be characterised. Distributing probe replicates across the array in this way helps to reduce or eliminate any distortion of signal and data interpretation, e.g. arising from a non-uniform distribution of background noise across the array.

As explained above, probes may be arranged on the support in subarrays.

The support, on which the plurality of probes is deposited, can be any solid support to which oligonucleotides can be attached. Practically any support, to which an oligonucleotide can be joined or immobilized, and which may be used in the production of DNA-chips, can be used in the invention. For example, the said support can be of a non-porous material, for example, glass, silicone, plastic, or a porous material such as a membrane or filter (for example, nylon, nitrocellulose) or a gel. In one embodiment, the said support is a glass support, such as a glass slide.

Microarrays are in general prepared by selecting probes which comprise a given polynucleotide sequence, and then immobilizing such probes to a solid support or surface. Probes may be designed, tested and selected as described herein. In general the probes may comprise DNA sequences. In some embodiments the probes may comprise RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Microarrays or chips can be made in a number of ways. However produced, microarrays typically share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 0.25 to 25 or 0.5 to 20 $cm^2$, such 0.5 to 20 $cm^2$ or 0.5 to 15 $cm^2$, for example, 1 to 15 $cm^2$ or 1 to 10 $cm^2$, such as 2, 4, 6 or 8 $cm^2$.

Probes may be attached to the present support using conventional techniques for immobilization of oligonucleotides on the surface of the supports. The techniques used depend, amongst other factors, on the nature of the support used [porous (membranes, micro-particles, etc.) or non-porous (glass, plastic, silicone, etc.)] In general, the probes can be immobilized on the support either by using non-covalent immobilization techniques or by using immobilization techniques based on the covalent binding of the probes to the support by chemical processes.

Preparation of Non-Porous Supports (e.g., Glass, Silicone, Plastic) Requires, in General, Either Pre-treatment with reactive groups (e.g., amino, aldehyde) or covering the surface of the support with a member of a specific binding pair (e.g. avidin, streptavidin). Likewise, in general, it is advisable to pre-activate the probes to be immobilized by means of corresponding groups such as thiol, amino or biotin, in order to achieve a specific immobilization of the probes on the support.

The immobilization of the probes on the support can be carried out by conventional methods, for example, by means of techniques based on the synthesis in situ of probes on the support (e.g., photolithography, direct chemical synthesis, etc.) or by techniques based on, for example, robotic arms which deposit the corresponding pre-synthesized probe (e.g. printing without contact, printing by contact).

In one embodiment, the support is a glass slide and in this case, the probes, in the number of established replicates (for example, 6, 8 or 10) are printed on pre-treated glass slides, for example coated with aminosilanes, using equipment for automated production of DNA-chips by deposition of the oligonucleotides on the glass slides ("micro-arrayer"). Deposition is carried out under appropriate conditions, for example, by means of crosslinking with ultraviolet radiation and heating (80° C.), maintaining the humidity and controlling the temperature during the process of deposition, typically at a relative humidity of between 40-50% and typically at a temperature of 20° C.

The replicate probes are distributed uniformly amongst the areas or sectors (sub-arrays), which typically constitute a DNA-chip. The number of replicas and their uniform distribution across the DNA-chip minimizes the variability arising from the printing process that can affect experimental results. Likewise, positive and negative hybridisation controls (as described herein) may be printed.

To control the quality of the manufacturing process of the DNA-chip, in terms of hybridization signal, background noise, specificity, sensitivity and reproducibility of each replica as well as differences caused by variations in the morphology of the spotted probe features after printing, a commercial DNA can be used. For example, as a quality control of the printing of the DNA-chips, hybridization may be carried out with a commercial DNA (e.g. k562 DNA High Molecular Weight, Promega)

In the first place, the morphology and size of the printed spots are analyzed. In the hybridization with control DNA the parameters described below for determining reliability of genotype determination, are adhered to; specifically the relationship between the signal intensity and background noise, average specificity and sensitivity and reproducibility between replicated copies of the same probe. This method allows the correct genotype of the control DNA to be determined.

As above, in accordance with the present method, a nucleic acid sample, e.g. amplification or fragmentation products, comprising the genetic variation(s) to be detected (target DNA) is contacted with a probe array as described herein, under conditions which allow hybridisation to occur between target DNA and the corresponding probes. Specific hybridisation complexes are thus formed between target nucleic acid and corresponding probes.

The hybridization of e.g. fragmentation products, with probes capable of detecting corresponding genetic variations deposited on a support may be carried out using conventional methods and devices. In one instance, hybridization is carried out using an automated hybridisation station. For hybridization to occur, the e.g. fragmentation products, are placed in contact with the probes under conditions which allow hybridization to take place. Using stable hybridization conditions allows the length and sequence of the probes to be optimised in order to maximize the discrimination between genetic variations A and B, e.g. between wild type and mutant sequences, as described herein.

In one instance, the method relies on differential hybridisation, in particular an increase in hybridisation signal. The method involves formation of specific hybridisation complexes between target DNA and corresponding probes. Thus target DNA bearing the wild type sequence will hybridise to the probes designed to detect the wild type sequence, whereas target DNA bearing a mutant sequence will hybridise to the probes designed to detect that mutant sequence. The hybridisation complexes are detectably labelled by means described herein (e.g. the target DNA is directly labelled, or both target and probe are labelled in such a way that the label is only detectable on hybridisation). By detecting the intensity of detectable label (if any) at the predetermined probe positions it is possible to determine the nature of the target DNA in the sample. In this instance the probes (also referred to as allele specific oligonucleotides, ASOs) preferably have the variable nucleotide(s) at the central position, as described herein.

In another instance, hybridisation of target DNA to probes on the solid support (chip) may be followed by on-chip amplification, for example, using primer extension or ligation, e.g. oligonucleotide ligation assay (OLA) technologies (Eggerding F A, Iovannisci D M, Brinson E., Grossman P., Winn-Deen E. S. 1995 Human Mutation, 5:153-65). In this case, the probes on the support typically comprise the variable nucleotide(s) at the 3' end of the probe.

Labelling can be carried out during post hybridisation amplification. The labelling can be by direct labelling using, for example, fluorophores, enzymes, radioactive isotopes, etc. or by indirect labelling using, for example, specific binding pairs which incorporate fluorophores, enzymes etc., by using conventional methods, such as those previously mentioned in relation to labelling amplification or fragmentation products.

Post-hybridization amplification may be carried out, for example, using the "primer extension" methodology. Typically, after hybridization, an extension reaction of the hybrid oligonucleotides is carried out on the support (e.g. a glass slide). Extension may be carried out with directly or indirectly labelled nucleotides and will only happen if the extreme 3' of the oligonucleotide hybridizes perfectly with the amplification product.

Primer extension is a known method for genotype discrimination (Pastinen T, Raitio M, Lindroos K, Tainola P, Peltonen L, Syvanen A C. 2000 Genome Research 10:1031-42) and can be performed in a number of different ways. In a commonly used approach a set of allele specific oligonucleotide probes are designed to hybridise to the target sequences. The probes differ from one another in their extreme 3' nucleotide, which for each probe is designed to complement one of the possible polymorphic nucleotides at a given position.

When the 3' nucleotide of the probe complements the sequence under test then the ensuing base pairing allows a DNA polymerase to extend the oligonucleotide primer by incorporation of additional nucleotides that can be directly or indirectly labelled thereby allowing the subsequent identification of those probes that have been extended and those that have not. Probes that are successfully extended carry the complementary nucleotide to the SNP at their 3' end thus allowing the genotype of the test sample to be determined. Similar approaches, for example the Amplification Refractory Mutation System (ARMS) have also been developed.

Alternatively, a post hybridization ligation reaction may be carried out, for example using OLA methodology. After hybridization, a ligation reaction of the hybridised oligonucleotides is carried out on the support (e.g. glass slide) with labelled oligonucleotides. A ligation will only take place if the extreme 3' end of the probe deposited on the support hybridizes perfectly with the target DNA (e.g. amplification product).

The oligonucleotide ligation assay (OLA) is another method for interrogating SNPs (Eggerding F A, Iovannisci DM, Brinson E., Grossman P., Winn-Deen E. S. 1995 Human Mutation, 5:153-65). OLA uses a pair of oligonucleotide probes that hybridize to adjacent segments of target DNA including the variable base. The probe designed to hybridise to the 5' side of the polymorphic nucleotide is an allele-specific oligonucleotide (ASO) to one of the target alleles. The last base at the 3' end of this ASO is positioned at the site of the target DNA's polymorphism; the ASO typically also has a biotin molecule at its 5' end that functions as a "hook" that can subsequently be used to recover the oligonucleotide by virtue of the highly specific interaction that biotin undergoes with streptavidin.

The oligomer on the 3' or right-hand side of the pair is the common oligomer (the sequence is the same for the two or more different alleles it is wished to test.) The common oligomer is positioned at an invariable site next to the target DNA's polymorphism and is fluorescently labelled at its 3' end.

If the ASO is perfectly complementary to the target sequence the ASO hybridizes completely when annealed and will lie flat against that target allowing DNA ligase to covalently join the ASO to the common oligomer. After the ligation reaction the biotin hook is used to remove the ASO and the e.g. fluorescently labeled common oligomer will also be removed, producing detectable fluorescence.

When the ASO is not a perfect match to the target sequence hybridization is incomplete and the 3' base of the oligomer will not be base-paired to the target DNA thus preventing ligation. Under these circumstances when the biotin hook is used to remove the ASO, the common oligonucleotide will not be removed and therefore there is no detectable label, e.g. fluorescence, in the molecule removed.

To distinguish between two known alleles that differ by a single base, three oligonucleotides are necessary: Two are allele-specific oligonucleotides (ASOs) that differ from each other only in the single 3' terminal base; the first is complementary to one allele and the second is complementary to the second allele. The third oligonucleotide is complementary to the invariable sequence adjacent to the variant base.

Once hybridisation (and optionally post-hybridisation amplification) has taken place, the intensity of detectable label at each probe position (including control probes) can be determined. The intensity of the signal (the raw intensity value) is a measure of hybridisation at each probe.

The intensity of detectable label at each probe position (each probe replica) may be determined using any suitable means. The means chosen will depend upon the nature of the label. In general an appropriate device, for example, a scanner, collects the image of the hybridized and developed DNA-chip. An image is captured and quantified.

In one instance, e.g. where fluorescent labelling is used, after hybridization, (optionally after post-hybridization amplification or ligation) the hybridized and developed DNA-chip is placed in a scanner in order to quantify the intensity of labelling at the points where hybridization has taken place. Although practically any scanner can be used, in one embodiment a fluorescence confocal scanner is used. In this case, the DNA-chip is placed in the said apparatus and the signal emitted by the fluorophore due to excitation by a laser is scanned in order to quantify the signal Intensity at the points where hybridization has taken place. Non-limiting examples of scanners which can be used according to the present invention, include scanners marketed by the following companies: Axon, Agilent, Perkin Elmer, etc.

Typically, in determining the intensity of detectable label at each probe position (i.e. for each probe replica), account is taken of background noise, which is eliminated. Background noise arises because of non-specific binding to the probe array and may be determined by means of controls included in the array. Once the intensity of the background signal has been determined, this can be subtracted from the raw intensity value for each probe replica in order to obtain a clean intensity value. Typically the local background, based on the signal intensity detected in the vicinity of each individual feature is subtracted from the raw signal intensity value. This background is determined from the signal intensity in a predetermined area surrounding each feature (e.g. an area of X, Y or Z µm2 centred on the position of the probe).

The background signal is typically determined from the local signal of "blank" controls (solvent only). In many instances the device, e.g. scanner, which is used to determine signal intensities will provide means for determining background signal.

Thus, for example, where the label is a fluorescent label, absolute fluorescence values (raw intensity values) may be gathered for each probe replica and the background noise associated with each probe replica can also be assessed in order to produce "clean" values for signal intensity at each probe position.

Once the target DNA has been hybridised to the chip and the intensity of detectable label has been determined at the probe replica positions on the chip (the raw intensity values), it is necessary to provide a method (model) which can relate the intensity data from the chip to the genotype of the individual.

The inventors have found that this can be done by applying a suitable algorithm to the intensity data. The algorithm and computer software developed by the inventors allows analysis of the genetic variations with sufficient sensitivity and reproducibility as to allow use in a clinical setting. The algorithm uses three linear functions which characterise each of the three genotypes AA, AB and BB for a given genetic variation. The method generally involves collating the intensity values for all of the replicas of each probe, to calculate an average intensity value for each probe. Optionally, the raw intensity values for each replica may be amended to take account of background noise (to obtain a clean intensity value) before the intensity values for each of the replicas are collated.

In general, for a given genetic variation, analysis and interpretation of a chip comprises the following steps:

(a) providing the intensity of detectable label at each replica for each of at least four probes (probes 1, 2, 3 and 4) provided for detection of the genetic variation (the raw intensity value), wherein:

probe 1 detects (is capable of specifically hybridising to) genetic variation A (e.g. a normal allele), and probe 2 detects (is capable of specifically hybridising to) genetic variation B (e.g. a mutant allele);

probe 3 detects (is capable of specifically hybridising to) genetic variation A (e.g. a normal allele) and probe 4 detects (is capable of specifically hybridising to) genetic variation B (e.g. a mutant allele); and probes 1 and 2 form a first probe pair and probes 3 and 4 form a second probe pair;

(b) optionally amending the raw intensity value for each replica to take account of background noise, thus obtaining a clean intensity value;

(c) collating the (optionally clean) intensity values for each of the replicas of each probe and determining an average intensity value for each probe;

(d) calculating ratios 1 and 2 wherein:

$$\text{Ratio 1} = \frac{\text{average intensity value for probe 1}}{\text{average intensity value for probe 1} + \text{average intensity value for probe 2}}$$

and $$\text{Ratio 2} = \frac{\text{average intensity value for probe 3}}{\text{average intensity value for probe 3} + \text{average intensity value for probe 4}}$$

(e) inputting ratios 1 and 2 into each of three linear functions which characterise each of the three possible genotypes, AA, AB and BB, wherein:

Function 1 is the linear function that characterises individuals with the genotype AA and consists of a linear combination of ratios 1 and 2;

Function 2 is the linear function that characterises individuals with the genotype AB and consists of a linear combination of ratios 1 and 2;

Function 3 is the linear function that characterises individuals with the genotype BB and consists of a linear combination of ratios 1 and 2;

the linear functions are formed by coefficients which accompany the variables ratio 1 and 2;

(f) determining which of the three linear functions has the highest value; and (g) thereby determining the genotype of the individual for the genetic variation.

Thus the linear function corresponding to the genotype of that individual will have the highest absolute value.

The inventors have found that the use of replicas and averages calculated from replicas is important for reliable working of the invention. Use of the functions speeds up analysis and allows better discrimination.

Preferably the discrimination capacity between the three genotypes is (approximately) 100%. If the discrimination is less than 100% the probes are preferably redesigned.

The raw intensity value for each probe replica may be determined according to the methods described above. Thus probe sequences and replicas can be selected as described herein. In one example, 4 probes are used per genetic variation and 6, 8 or 10 replicas are used per probe.

Typically, amending the raw intensity value to obtain the clean intensity value for each probe replica comprises subtracting background noise from the raw value. Background noise is typically determined using appropriate controls as described herein.

Typically calculating the average intensity value comprises eliminating extreme values or outliers. Thus, when the (optionally clean) intensity values from each of the probe replicas are collated, outlying values can be identified and excluded from further consideration. In one embodiment outliers make up between 10% and 50%, for example, 15, 20, 25, 30, 35, 40 or 45% of the values obtained. In one embodiment, 40% of values are eliminated. In one embodiment, 4 probes are used with 6, 8 or 10 replicas per probe and extreme values or outliers make up between 10% and 50% of the values obtained.

A number of suitable linear functions are known in the art. These functions may be used in a linear discriminant analysis for the purposes of the present invention.

In one aspect the invention thus relates to a computational method or model (algorithm) for determining genotype with respect to a given genetic variation using ratios 1 and 2 in the three linear functions as defined above (steps e and f). The method can thus in one embodiment produce an output of genotype (AA, AB or BB) from an input of ratios 1 and 2. The method may also include calculating one or both of ratios 1 and 2 (step d). In some embodiments the method additionally comprises calculating an average intensity value for each probe (step c) and/or calculating a clean intensity value for each probe replica (step b). Thus the input to the model may comprise one or more of the average intensity values, clean replica intensity values or raw replica intensity values. The method may additionally comprise determining the raw intensity value for each probe replica (step a). The method may comprise one or more of the above steps.

In order to carry out the above methods, the coefficients for the linear functions must first be determined in a training process using data from control individuals whose genotype for the genetic variation is already known. Methods for training are known in the art. Typically in such methods, input data (in this case, typically ratios 1 and 2) is used for which the output (in the present case, genotype) is already known. Coefficients are substituted in the three linear equations at random and the output is calculated. Based on that output, one or more coefficients are altered and the input data is entered again to produce another output. The process is continued until coefficients are obtained which optimise the desired output. These optimised coefficients are then used in the linear functions when the method is applied to test data (where the output is as yet unknown).

In order to train the present model, ratios 1 and 2 are obtained for n control individuals having genotype AA (for example, homozygous wild type), n control individuals having genotype AB (heterozygous) and n control individuals having genotype BB (for example, homozygous mutant). The ratios may be obtained using the methods described above. The ratios are inputted as above and the coefficients altered in a discriminatory analysis until three linear functions are obtained which maximise discrimination between the AA, AB and BB groups. These coefficients are then used in the three functions when the model is used on unknown test samples (where the genotype is not predetermined).

Thus in one aspect the invention provides a method of deriving linear functions for use in the present genotyping methods. The method typically comprises carrying out the steps of the genotyping methods as described, for n control individuals having genotype AA (for example, homozygous wild type), n control individuals having genotype AB (heterozygous) and n control individuals having genotype BB (for example, homozygous mutant) with respect to a genetic variation. The intensity values obtained for each of the probe replicas are gathered as described and an algorithm is applied.

As described for the genotyping methods, application of the algorithm comprises calculating an average intensity value for each probe and the algorithm uses three linear functions intended to characterise each of the three possible genotypes, AA, AB and BB for the given genetic variation. Coefficients are inserted in the functions in a repetitive way until functions are derived which maximise discrimination between the genotypes in a discriminatory analysis. This provides the coefficients for use in the linear functions when the method or algorithm is in operational use (i.e. to determine the genotype of test individuals).

The algorithm or method which uses the three linear functions for analysing the intensity data may be as described above.

In some cases, the training method allows feedback optimisation. Thus, as intensity values and ratios are obtained for test individuals and these are genotyped, the intensity data, e.g. the ratios, and genotype are inputted and coefficients recalculated for the linear functions.

In one aspect the invention relates to a computational method for training. The method can be used to derive linear functions for use in the present genotyping methods by using ratios 1 and 2 obtained for each of n individuals having genotype AA, n individuals having genotype AB and n individuals having genotype BB with respect to a genetic variation. The ratios can be obtained by the methods described above. The method typically comprises applying the algorithm which uses the three linear functions (Functions 1, 2 and 3) intended to characterise each of the three possible genotypes AA, AB or BB for the genetic variation such that:
Function 1 is the linear function that characterises individuals with the genotype AA and consists of a linear combination of ratios 1 and 2;
Function 2 is the linear function that characterises individuals with the genotype AB and consists of a linear combination of ratios 1 and 2;
Function 3 is the linear function that characterises individuals with the genotype BB and consists of a linear combination of ratios 1 and 2; and
the linear functions are formed by coefficients which accompany the variables ratio 1 and 2;
and deriving linear functions which maximise discrimination between the three genotype groups AA, AB and BB in a discriminatory analysis, so as to obtain the coefficients which can be used in the linear functions when the algorithm is used in a test method (i.e. is in operational use for determining genotype).

The algorithm or method which uses the three linear functions for analysing the intensity data may be as described above.

The computational training method may additionally involve calculating ratios 1 and 2 from average intensity value provided for each of the probes, and/or collating intensity values from probe replicas to determine an average intensity value for each probe and/or amending a raw intensity value for a probe replica to take account of background noise thereby obtaining clean intensity values for the replica.

In some aspects the computational method also allows a feedback optimisation step as described.

Typically in training n is ≥3, for example, 3, 4, 5, 6, 7, 8, 9 or 10. In one aspect, n is ≥5. In some cases n may be from 10 to 50 or more, for example, 15 to 40, or 25 to 35, such as 20 or 30.

Probes and probe replicas for the training method are selected as described herein. In one embodiment 4 probes are used for each genetic variation, with 6, 8 or 10 replicas of each probe. Once selected, the probes used in training are also used when the model is in operational use (to determine unknown genotype). If the probes are altered, typically the model must be retrained to optimise discrimination with the new probes.

Preferably the coefficients are such that the discrimination between the three genotype groups (both in training and in operational use) is substantially 100%. If the discrimination is not 100%, the probes are preferably redesigned.

As above, the model may also undergo feedback optimisation when it is in operational use. In that case, the model is first used to determine the genotype of an individual (AA, AB or BB). The ratios 1 and 2 for that individual are then inputted into the model and the coefficients in the linear functions altered as necessary in order to optimise discrimination between the three genotype groups. In this way, the additional data gathered as the model is in use can be used to optimise the discrimination capacity of the linear functions.

There are a number of parameters which can be determined and optimised in order to optimise performance and reliability of the analytical model or method.

(i) In one aspect ratios 1 and 2 determined for an individual fall within the range of ratios 1 and 2 used to train the model (i.e. to optimise the three linear functions). If desired this can thus provide a double test for the genotype of an individual.

(ii) In one aspect the average fluorescence intensity of 4n replicas (where "n" is the number of replicas for each probe, e.g. 6, 8 or 10), for example, 40 replicas, with regard to the background noise is greater than 5.

(iii) In one aspect the variation between intensity values (raw or clean) for replicas of the same probe is a minimum. For example, the coefficient of variation between the intensity values for the replicas of a given probe is preferably less than 0.25

(iv) In one aspect the ratio of the sum of the raw intensity values for all probe replicas on a chip to the intensity of the background noise is greater than 15 when a fluorescence scanner is used.

(v) In one aspect the raw signal intensity value obtained for the negative controls is 53 times greater than the intensity value of the background noise. For example, negative controls may include the DMSO "blank" and the non-hybridising oligonucleotides referred to above. The background noise is the signal derived from the regions of the array where no probe has been spotted and may be determined as above.

Preferably any one or more of (i) to (v) applies when intensity is fluorescence intensity of a fluorescent label, in particular where the intensity is determined by means of a confocal fluorescent scanner.

Ensuring that the model meets one or more of the above helps to provide reliability and reproducibility. Any one or more of (i) to (v) may be true for the model. Preferably the model meets (i) above. In one example, (i), (ii) and (iii) are true. In another example, (iii), (iv), (v) are true. Preferably, all of the above are true for the model. This applies both to training and to operational use.

As above, the experimentally derived ratios obtained for a test sample may be compared to the ratios previously obtained for the (n) control samples obtained from individuals of known genotype, where n is as above, usually >5, or >10, or >20. The reference ratios derived from analysis of the control samples permits a genotype to be assigned to the test sample. This can therefore be a double test.

In one instance the analytical method or algorithm of the invention comprises a sequence of the following steps:
using 4 probes (2 pairs of probes) in replicate (6, 8 or 10 replicas), calculating the average intensity of each probe from the collated intensities of the replicas; calculating ratios 1 and 2 as above for the 2 pairs of probes (to detect the genetic variations A and B); substituting ratios 1 and 2 obtained in three linear equations which have been derived in a discriminatory analysis using ratios 1 and 2 calculated for "n" control patients with genotype AA, "n" control patients with genotype AB and "n" control patients with genotype BB (with respect to the genetic variation) (in one experiment "n" is 5); and determining the genotype of a patient for the genetic variation (for each genetic variation included in the DNA-chip) based on which linear function has the greatest absolute value. The test ratios may also be compared to the ratios of the "n" control patients to determine each genotype.

The analysis and interpretation above has been described with respect to one genetic variation. However, it is to be understood that the present chip generally includes probes for detection of multiple genetic variations which can be analysed at the same time. Thus the present methods include analysis of multiple genetic variations, as described herein, in parallel.

In a further aspect the invention relates to a computer system comprising a processor and means for controlling the processor to carry out a computational method of the invention.

The invention additionally relates to a computer program comprising computer program code which when run on a computer or computer network causes the computer or computer network to carry out a computational method of the invention. The computer program may be stored on a computer readable medium.

In addition to the probes and chips described herein, the inventors have also designed and validated oligonucleotide primers which are capable of amplifying, e.g. by means of multiplex PCR, target DNA regions containing the human genetic variations associated with PCa in Table 1A. These primers are useful in preparing nucleic acid for use in the present genotyping, prognostic and therapeutic methods.

Tables 3A & 3B list pairs of primers which amplify target DNA regions containing the PCa associated genetic variations in Table 1A (SEQ ID NOS 361-538) along with the corresponding genetic variation.

The listed oligonucleotide primers have the advantage of allowing specific amplification of the said target DNA regions in a very low number of PCR reactions. The listed primers allow, in a minimum number of multiplex PCR reactions, amplification of all the fragments necessary for genotyping the genetic variations in Table 1A, and which may be analyzed on Proscan.

In a further aspect, the present invention relates to each of the PCR primers listed in Tables 3A & 3B, and in particular to each of the listed pairs of PCR primers and their use in PCR amplification, e.g. in a multiplex PCR reaction, of a target DNA region containing the corresponding genetic variation. The invention in one aspect provides any one of these primers or pairs of primers for use in medicine, in particular for use in the present genotyping, prognostic or therapeutic methods.

The invention further relates to a PCR amplification kit comprising at least one pair of listed PCR primers. The kit may additionally include, for example, a (thermostable) polymerase, dNTPs, a suitable buffer, additional primers, and/or instructions for use, e.g. to amplify a target DNA region containing the corresponding genetic variation. The kit may be used for amplification of target DNA regions from nucleic acid samples, for use in the present methods.

In another aspect the present invention relates to a genotyping or diagnostic (preferably in vitro) kit for genotyping PCa associated genetic variations and/or for diagnosing PCa or susceptibility to PCa. The kit comprises a DNA-chip or array according to the invention. The kit may additionally comprise instructions for use of the chip in a genotyping method of the invention, for example instructions for use in the present analytical method or algorithm. Further components of a kit may include:
  computer software, a computer program or a computer system according to the invention;
  one or more PCR primers or pairs of PCR primers according to the Invention; and/or
  a PCR amplification kit according to the invention.

The probes for the chip or PCR primers may be selected as above depending on the genetic variations to be detected or the diagnostic purpose of the kit.

The kit may contain one or more positive and/or negative controls of the hybridisation reaction.

The invention further relates to the use of the kit in a genotyping, prognostic or therapeutic method of the invention.

As described herein, the present genotyping methods are useful for diagnosing PCa or susceptibility to PCa in a subject. The genotyping results obtained in the methods may be used to determine prognosis and may be useful in determining the appropriate treatment for PCa (e.g. by predicting response to therapy).

PCa presents a number of phenotypes, most notably benign vs malignant and localised vs metastatic cancer. In some cases, PCa may be biologically aggressive and likely to progress to metastatic cancer. There may be a predisposition to suffer therapy related osteoporosis, or androgen-deprivation therapy resistance. Patients may also differ in their response to radiation therapy.

Little is currently known about what makes some PCa biologically aggressive and more likely to progress to metastatic and potentially lethal disease. Identifying genetic variations in some key genes involved in PCa aggressiveness would be extremely valuable for predicting PCa progression and for determining specific treatment options in men diagnosed with the disease.

Some groups of men receiving androgen-deprivation therapy for PCa, an increasingly common treatment, show an increased risk of bone fracture while others never do. Identifying patients with genetic predisposition to suffer from therapy-related osteoporosis could be useful to select individuals for preventive anti-osteoporotic treatment with bisphosphonates.

Genetic variations in hormone metabolism-related genes like androgen receptor (AR) in men have been associated to androgen-deprivation therapy resistance. Detecting germline variations in those genes could be useful to identify patients who would benefit from alternative therapeutic actions such as surgery, radiation and chemotherapy.

External-beam radiotherapy appears to be as effective as surgery in curing prostate cancer. However, a group of patients may experience severe late sequelae, specifically proctitis or cystitis, after high-dose external-beam conformal radiation therapy. Detecting DNA variations associated to individual response to radiation could help identify prospectively those patients and, with dose de-escalation, spare them a great deal of discomfort and suffering.

Particular genetic variations associated with PCa may be predictive of particular phenotypes or development of particular phenotypes and hence disease progression. In other words, it may be that there is a statistically significant association between e.g. the mutant allele B, of a given genetic variation and the occurrence/development of a particular phenotype.

Since the present genotyping methods allow reliable genotyping of multiple genetic variations in a clinical setting, these can be used to genotype individuals of known PCa phenotype, and to thus identify genetic variations predictive of particular PCa phenotypes.

In one aspect the invention therefore relates to a method of identifying genetic variations predictive of a particular PCa phenotype, such as the phenotypes listed above. The method involves genotyping a plurality of individuals with respect to one or more genetic variations associated with PCa using a method of the invention. In such a retrospective study typically 300-1000 individuals are genotyped, for example 400, 500 or 600 individuals may be genotyped. The phenotype of each individual is already known based on standard clinical procedures (e.g. biopsy).

Once the genotypes are obtained, this data is compared with the phenotype data and statistically significant associations between particular genotypes and particular phenotypes are identified. Methods for determining statistical significance are known in the art.

The genetic variations identified as predictive of particular phenotypes/disease course can then be used to diagnose these phenotypes/disease courses in test individuals, by genotyping the individuals with respect to the predictive genetic variation (s). Thus it is possible to determine the likely course of disease progression in the individual. Genotyping can be done by any appropriate method, depending on the number of variations to be tested. For example, a genotyping method of the invention may be used. Alternatively, sequence based or other chip-based methods may be appropriate.

Thus in one aspect the invention further relates to a method of diagnosing PCa phenotype or predicting the likely course of disease progression in an individual by determining the genotype of the individual with respect to one or more genetic variations which have been identified as predictive (of the particular PCa phenotype or disease course) by the methods described herein.

Once the prediction has been made, it will then be possible to select the most suitable therapeutic approach, e.g. to determine the need for surgical intervention.

The present arrays and methods thus provide a means for clinicians to predict the likely course of disease progression in PCa patients and also aid in the selection of the most suitable treatment regime. They are therefore useful prognostic tools. Genotype information obtained according to the present invention may aid in clinical decision making or diagnosis in cases where symptoms (disease phenotype) are ambiguous. Genetic information provided by Proscan or other methods could also help in determining the likelihood of disease development in asymptomatic individuals (e.g. immediate family members of PCa sufferers) allowing, for example, guidance on lifestyle and diet to be provided and indicating the need for continued monitoring of individuals who have a genetic constitution that indicates possible susceptibility to disease development.

In one aspect the invention therefore relates to a method of diagnosing PCa or susceptibility to PCa in an individual, or determining the likely course of disease progression in an individual as above. Preferably the method is in vitro. The invention further relates to a method of selecting a treatment, for an individual having PCa, in some cases where the individual has been diagnosed or tested according to the methods of the invention. Still further the invention in some aspects relates to methods of treating an individual suffering from PCa, wherein, after the treatment is selected, the treatment is administered to the individual.

The diagnostic, predictive and therapeutic methods may comprise carrying out a genotyping method of the invention as described herein. Any of the methods may involve carrying out a training method of the invention as described herein in order to derive linear functions for use in determining genotype. Further the methods may comprise the use of a chip, computer system, computer program, oligonucleotide probes or pair or set of probes, oligonucleotide primer or pair of primers, PCR amplification kit or diagnostic kit of the invention as described herein.

Apart from the contribution to the diagnosis and treatment of PCa and the development of new therapeutic strategies for this disease, the present invention is useful for elucidating the molecular origin of PCa and the biology of other cancers.

In one aspect the present invention relates to a microarray adapted for use in the present methods as described herein.

The invention further relates to the use of one or more oligonucleotide probe(s) and/or one or more primer(s) or primer pair(s) of the invention in a method for prognosing PCa, such as a method described herein.

Further aspects of the invention will now be illustrated with reference to the accompanying Figures and experimental exemplification, by way of example and not limitation. Further aspects and embodiments will be apparent to those of ordinary skill in the art. All documents mentioned in this specification are hereby incorporated herein by reference.

EXAMPLES

Although in general, the techniques mentioned herein are well known in the art, reference may be made in particular to Sambrook et al, 1989, Molecular Cloning: a laboratory manual.

Example 1

Detection of PCa Associated Human Genetic Variations Using a DNA-Chip According to the Invention (Proscan)

1.1 Design of the DNA-Chip for Genotyping PCa Associated Genetic Variations

A DNA-chip to detect human genetic variations associated with PCa which permits simultaneous, sensitive, specific and reproducible detection was designed and manufactured. The said genetic variations are related to a greater or lesser risk of suffering from PCa, a better or worse response to treatment and also a better or worse prognosis of the disease. Illustrative examples of human genetic variations associated with antigens connected to PCa which can be determined using this DNA-chip are shown in Table 1A (FIG. 1).

The DNA-chip designed and manufactured consists of a support (glass slide) which shows a plurality of probes on its surface that permits the detection of genetic variations previously mentioned. These probes are capable of hybridizing with the amplified sequences of the genes related to PCa. The DNA sequences of each one of the probes used is referred to in Table 2 (FIG. 2) [in general, the name of the gene and the mutation is indicated (change of nucleotide, "ins": insertion "del" deletion or change of amino acid)]. The listed probes have all been technically validated.

1.2 Production of the DNA-Chip
Printing and Processing of the Glass Slides

The probes capable of detecting the genetic variations previously identified are printed onto aminosilane coated supports (glass slides) using DMSO as a solvent. The printing is carried out using a spotter or printer of oligonucleotides (probes) while controlling the temperature and relative humidity.

The joining of the probes to the support (glass slides) is carried out by means of cros slinking with ultraviolet radiation and heating as described in the documentation provided by the manufacturer (for example, Corning Lifesciences as found at corning.com). The relative humidity during the deposition process is maintained between 40-50% and the temperature around 20° C.

1.3 Validation of the Clinical Usefulness of the DNA-Chip
1.3.1 Preparation of the Sample to be Hybridized The DNA of the individual is extracted from a blood sample by a standard protocol of filtration. (For example, commercial kits from Macherey Nagel, Qiagene etc).

Target DNA regions containing the genetic variations of interest are amplified by multiplex PCR using appropriate pairs of oligonucleotide primers. Any suitable pair of oligonucleotides can be used which allow specific amplification of genetic fragments where a genetic variation to be detected might exist. Advantageously, those pairs of oligonucleotide primers which permit the said amplifications to be performed in the least possible number of PCR reactions are used.

The oligonucleotide primers used to PCR amplify target regions containing the genetic variations in Table 1A are listed in Tables 3A & 3B (FIG. 3) (SEQ ID NOS: 361-538). These primers represent an additional aspect to the invention.

The PCR multiplex reactions are carried out simultaneously under the same conditions of time and temperature which permit specific amplification of the gene fragments in which the genetic variations to be detected might exist. Once the PCR multiplex has finished, agarose gel analysis is used to check that the amplification reaction has taken place.

Next, the sample to be hybridized (products of amplification) is subjected to fragmentation with a DNase and the resulting fragmentation products subjected to indirect labelling. A terminal transferase adds a nucleotide, covalently joined to one member of a pair of molecules that specifically bind to one another (e.g. biotin allowing subsequent specific binding to streptavidin) to the ends of these small DNA fragments.

Before applying the sample to the DNA-chip, the sample is denatured by heating to 95° C. for 5 minutes and then, the "ChipMap Kit Hybridization Buffer" (Ventana. Medical System) is added.

1.3.2 Hybridization

Hybridization is carried out automatically in a hybridisation station such as the Ventana Discovery (Ventana Medical Systems) that has been specifically developed for such a use. Alternatively hybridisation can be performed manually.

The prehybridization and blocking of the slides is carried out with BSA. Next, the hybridization solution {ChipMap Kit Hybridization Buffer, Ventana Medical System) is applied to the surface of the DNA-chip which is maintained at 45° C. for 1 hour following the protocol of Ventana 9.0 Europe (Ventana Medical System). Finally the slides are subjected to different cleaning solutions (ChipMap hybridisation Kit Buffers, Ventana Medical System). Once the process of hybridization has finished, the final cleaning and drying of the slides begins.

When hybridization has taken place, the DNA chip is developed by incubation with a fluorescently labelled molecule that is able to specifically bind to the molecule incorporated into the amplification product by terminal transferase (e.g. in the case of biotin incorporation a fluorophore coupled to streptavidin such as streptavidin-Cy3 can be used) to label the probe positions where hybridization has occurred.

1.3.3. Scanning the Slides

The slides are placed in a fluorescent confocal scanner, for example Axon $4100^a$, and the signal emitted by the fluorophore is scanned when stimulated by the laser.

1.3.4 Quantification of the Image

The scanner's own software allows quantification of the image obtained from the signal at the points where hybridization has taken place.

1.3.5 Interpretation of the Results

From the signal obtained with the probes which detect the different genetic variations, the genotype of the individual is established. In the first instance the scanner software executes a function to subtract the local background noise from the absolute signal intensity value obtained for each probe. Next, the replicates for each of the 4 probes that are used to characterize each genetic variation are grouped. The average intensity value for each of 4 probes is calculated using the average collated from the replicates in order to identify abnormal values (outliers) that can be excluded from further consideration. Once the average intensity value for each of the probes is known then two ratios are calculated (ratio 1 and ratio 2):

$$\text{Ratio 1} = \frac{\text{average intensity for probe 1}}{\text{average intensity for probe 1} + \text{average intensity for probe 2}}$$

$$\text{Ratio 2} = \frac{\text{average intensity for probe 3}}{\text{average intensity for probe 3} + \text{average intensity for probe 4}}$$

wherein probe 1 detects (is capable of specifically hybridising to) genetic variation A (e.g. a normal allele), probe 2 detects (is capable of specifically hybridising to) genetic variation B (e.g. a mutant allele), probe 3 detects (is capable of specifically hybridising to) genetic variation A (e.g. a normal allele) and probe 4 detects (is capable of specifically hybridising to) genetic variation B (e.g. a mutant allele).

These ratios are substituted in three linear functions which characterize each one of the three possible genotypes:

| AA | Function 1 |
| AB | Function 2 |
| BB | Function 3 |

The function which presents the highest absolute value determines the genotype of the patient. In this case, the linear functions are obtained by analyzing 5 subjects for each of the three possible genotypes of the genetic variation (AA, AB, BB). With the results, ratios 1 and 2 are calculated for the 15 subjects. These ratios are classification variables for the three groups to create the linear functions, with which the discriminatory capacity of the two pairs of designed probes are evaluated. If the discriminatory capacity is not 100%, the probes are redesigned. New subjects characterized for each of the three genotypes make up new ratios 1 and 2 to perfect the linear functions and in short, to improve the discriminatory capacity of the algorithm based on these three functions.

When using a confocal fluorescent scanner, to obtain reliable results it is preferable that ratios 1 and 2 are within the range of the ratios used to build the groups, the average fluorescence intensity of the 4n (for example 40) replicates with regard to background noise is greater than 5 and the coefficient of variation of all of the DNA-chip replicates is below 0.25.

Again when a fluorescent confocal scanner is used in the experiment, for a complete hybridization to be considered reliable preferably the ratio of probe fluorescence intensity to background noise of all the DNA-chip probes is above 15. Likewise, the average of all the ratios is preferably above 0.6 and the negative control is preferably less than or equal to 3 times the background noise To sum up, in this case 4 probes (repeated 10 times) are presented on the slide for detection of each mutation. Two of the probes detect one genetic variation (A) and the other two the other genetic variation (B). The examined base is located in the central position of the probes.

A subject homozygous for the genetic variation A will not show genetic variation B. Consequently, in the image obtained from the glass support the probes which detect genetic variation B will show a hybridization signal significantly less than that shown by variation A and vice versa. In this case the ratios 1 and 2 will show 1 and the subjects will be assigned as homozygous AA by the software analysis.

On the other hand, a heterozygous subject for the determined genetic variation shows both the genetic variations. Therefore, the probes which detect them show an equivalent hybridization signal. The ratios 1 and 2 will show 0.5 and the subject will be assigned as heterozygous AB by the software analysis.

Oligonucleotide primers used for PCR amplifications are listed in Tables 3A and 3B (FIG. 3). These correspond to SEQ ID NOS: 361-538, with consecutive numbering of the forward/reverse primer pairs for each of the SNPs. Thus, for example, the forward primer for SNP1 (in BCL2) is SEQ ID NO: 361 and the reverse primer for SNP1 (in BCL2) is SEQ ID NO: 362. Similarly the forward primer for SNP2 (in CDKI1B) is SEQ ID NO: 363 and the reverse primer for SNP2 (in CDKI1B) is SEQ ID NO: 364. For another example, the forward primer for SNP6 (in HSD3B1) is SEQ ID NO: 371 and the reverse primer for SNP6 (in HSD3B1) is SEQ ID NO: 372.

Example 2

Establishing Models for Predicting PCa Phenotypes

Methods
Study Design

Records of 840 patients with Prostate Cancer (PCa) undergoing radical prostatectomy from the Department of Urology of Miguel Servet University Hospital, Zaragoza (Spain) were entered into the PCa HUMS (HUMS: Hospital Universitario Miguel Servet) database between 1986 and 2002. The database was screened for patients with clinically localized PCa with at least 5-years of follow-up after surgery. Individuals matching those criteria (n=375) were invited to participate in the study. A total of 269 patients out of 375 (72%) accepted to donate blood and clinical data for the study and signed informed consents. This group was composed of 85 men who developed PSA recurrence (post-prostatectomy PSA level of >0.2 ng/ml) during the first 5 years after surgery and 182 who did not experience PSA recurrence during this period. When recurrence was defined as post-prostatectomy PSA level of >0.4 ng/ml group composition was 74 and 193 respectively. Patients receiving adjuvant radiation (n=30) were excluded. The remaining 239 patients were used for the study.

The study was in accordance with the Helsinki Declaration (World Medical Association) and the EMEA (European Medicines Agency) recommendations.

Baseline clinical and analytical variables were recorded from every patient before and after surgery. Preoperative clinical variables were: onset age, PSA levels, biopsy Gleason grade and clinical stage. Postoperative clinical variables were: prostatectomy Gleason grade, pathological stage, lymph node involvement and surgical margin status.

Studied Phenotype

For localized PCa patients treated with radical prostatectomy, an increased PSA level usually indicates cancer progression or recurrence. Those who experience early PSA recurrence are more prone to develop metastatic lesions and poor prognosis. In our study presence or absence of biochemical progression (increase in PSA level) after 5-years of follow-up was considered as main outcome. Controversy exists regarding the importance of setting PSA levels>0.2 ng/ml or >0.4 ng/ml as the threshold for defining "biochemical tumor recurrence". The precision and sensibility of PSA assays seems to have improved in the last years. However, most studies concluded that the threshold for biochemical recurrence at 0.4 ng/ml is more reliable. In order to explore all possibilities four different analyses were performed: 1) prediction of PSA progression (defined as PSA>0.2 ng/ml) within 5 years of surgery using pre-operative clinical variables and SNP's. 2) prediction of PSA progression (defined as PSA>0.4 ng/ml) within 5 years of surgery using pre-operative clinical variables and SNP's. 3) prediction of PSA progression (defined as PSA>0.2 ng/ml) within 5 years of surgery using pre-operative and post-operative clinical variables and SNP's. 4) prediction of PSA progression (defined as PSA>0.4 ng/ml) within 5 years of surgery using pre-operative and post-operative clinical variables and SNP's.

Genotypinq and Single Nucleotide Polymorphism (SNP) Selection

Peripheral blood (2 ml) was obtained from each patient and placed in an EDTA-treated tube. DNA was extracted with the QIAamp DNA Blood MiniKit (Qiagen) following the manufacturer's specifications. Genotyping was carried out using PROSCAN DNA microarray. A total of 83 SNPs belonging to genes involved in androgen metabolism and signalling, carcinogen metabolism, cell proliferation, DNA-repair and growth factor signalling pathways, among others, were genotyped for each patient.

The SNP selection was based on previous published data and our own research expertise. The SNP selection in those genes was based on a minor allele frequency of 0.1. Only "TagSNPs" ($R^2>0.8$) were taken into account as this gave more statistical power by reducing the degrees of freedom (df) of our tests.

```
Foward TAG
TAG FW        SEQ ID NO 542 TAATACGACTCACTATAGGGAGA

Reverse TAGs
TAG RW        SEQ ID NO 543 AATTAACCCTCACTAAAGGGAGA
```

From all the SNPs genotyped, only those showing highest association to the studied phenotype were included in the stepwise logistic regression analysis to limit the overall false-positive rate. First of all, chi-squared ($X^2$) tests were performed in order to test the conformity with Hardy-Weinberg expectations (HWE) of the genetic polymorphisms under analysis. Tests of HWE were carried out for all loci among all the different phenotypes described. Only SNPs that conformed to HWE in both separate groups under analysis were included in the study. SNPs with extremely high deviations from the predictions of HWE (p values lower than 0.01) were excluded from the analysis since such deviations could indicate problems such as genotyping errors.

In addition, single locus association tests between SNP allele frequency (allelic associations) and patient status were carried out using the standard contingency $X^2$ test, and p-values were determined, including Bonferroni correction for multiple testing. The SNPs with the smallest p-values were included in the regression analysis. All the genetic analyses were carded out using HelixTree® software (Golden Helix, Inc., Bozeman, Mont., USA).

Statistical Modelling

For each model, the statistical analysis was carried out between the two patient groups (with or without 5-years PSA recurrence) to attempt discrimination between both groups in each of the four different analyses. Four different models were evaluated, one for each of the four analysis: one model to distinguish between patients with or without PSA progression (defined as PSA>0.2 ng/ml) within 5 years of surgery using pre-operative clinical variables and SNP's (model 1); one model to distinguish between patients with or without PSA progression (defined as PSA>0.4 ng/ml) within 5 years of surgery using pre-operative clinical variables and SNP's (model 2); one model to distinguish between patients with or without PSA progression (defined as PSA>0.2 ng/ml) within 5 years of surgery using pre-operative and post-operative clinical variables and SNP's (model 3) and one model to distinguish between patients with or without PSA progression (defined as PSA>0.4 ng/ml) within 5 years of surgery using pre-operative and post-operative clinical variables and SNP's (model 4).

Statistical analyses were performed using the Statistical Package for the Social Sciences (SPSS Inc. Headquarters, Chicago, Ill., USA) version 14.0. Multiple genotype-phenotype associations were analysed by means of multivariate logistic regression (Forward LR) with clinically determined disease phenotypes as dependent variables and the individual loci and clinical and analytical data as independent variables. The goodness of fit of the models was evaluated using Hosmer-Lemeshow statistics and their accuracy was assessed by calculating the area under the curve (AUC) of the Receiver Operating Characteristic curve (ROC) with 95% confidence intervals. The explained variability of the models on the basis of the SNPs was evaluated by means of the $R^2$ Nagelkerke. To measure the impact of the variables included in the models of the analysed phenotypes, the sensitivity, specificity, and positive likelihood ratio (LR+=sensitivity/(1–specificity)) were computed by means of ROC curves.

In order to verify association of individual genetic markers to PSA recurrence all along the follow-up, a survival analysis was performed. Estimates of PSA recurrence (event) were calculated using the Kaplan-Meier method and graphically displayed. Comparation of PSA recurrence probability for patients carrying AA, AB and BB genotypes for each SNP that entered in the models was performed using Log Rank, Breslow and Tarone-Ware statistics.

The Kaplan-Meier figures show on the x-axis "time of follow-up" and on y-axis "proportion of patients without recurrence (cumulated survival) for the 3 alternative genotypes. All along the follow-up the proportion of patients without recurrence decreases, but for some SNPs the decrease is significantly more dramatic for any one of the genotypes For example, in FIG. 9 for SNP24, 3 years after surgery, 80% patients carrying genotype 0 or 1 don't present recurrence but for those carrying genotype 2 only 25% don't present recurrence. To see if those differences are significant or a pairwise comparison can be made of the differences in recurrence-free time between the 3 genotypes (Table 9). The comparison is made by three different statistical tests (Log Rank, Breslow and Tarone). For example, the Log Rank Test shows that significant differences are found between 0 and 2 genotypes (P=0.020) and close to significance differences exists between genotypes 1 and 2 (P=0.059). The Chi-square value is the statistical value that allows calculation of the P-value.

Results

To differentiate between the two phenotypes (recurrence of prostate cancer within five years of surgery, or not), four models were obtained: a) model 1: two predictors (SNP46 [rs7799039]+PSA) entered into the forward LR model, b) model 2: five predictors (SNP46 [rs7799039]+SNP24 [rs328]+PSA+Onset Age+Clinical Stage) entered in the model, 3) model 3: seven predictors (SNP24 [rs328]+SNP31 [rs1048943]+SNP56 [rs4646903]+PSA+Prostatectomy Gleason Grade+Surgical Oncologic Margins+Surgical Gland Margins) entered in the model 4) model 4: Eight predictors (SNP24 [rs328]+SNP25 [rs1042522]+SNP31 [rs1048943]+SNP32 [rs12329760]+PSA+Prostatectomy Gleason Grade+Surgical Oncologic Margins+Surgical Gland Margins) entered in the model. Information regarding the variables (clinical and SNPs) remaining in each function is shown in Tables 4 to 7 (FIGS. 4A to 7A). Regression probability functions are built using the Statistical Package for the Social Sciences (SPSS Inc. Headquarters, Chicago, Ill., USA) version 14.0. SPSSv14. B is the coefficient associated to each genotype in the probability function. ET is the error in the calculation of B. Wald is the statistical test. GL freedom degrees. Sig. P value of B for the Wald test. Exp (B) is Relative Risk.

The contribution of genetic and clinical factors to studied PCa phenotypes can be further demonstrated by the substantial proportion of variance ($R^2$ Nagelkerke) explained by the functions (13% for model 1; 26% for model 2; 33% for model 3 and 39% for model 4). Probability functions and ROC curves were obtained for the analysed phenotype. ROC curves, sensitivity, specificity and positive likelihood ratios (LR+) of all the models are given in FIGS. 4 to 7.

Nagelkerke R2 is a way of measuring the proportion of variants explained by the functions. The area under the ROC-curve (ROC AUC) is a measure of test performance or "diagnostic accuracy". The positive likelihood ratio (LR+) is calculated as sensitivity/1−specificity.

Figure 19B:
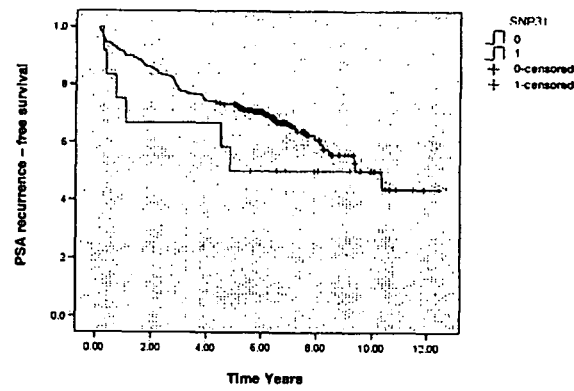
Figure 20B:
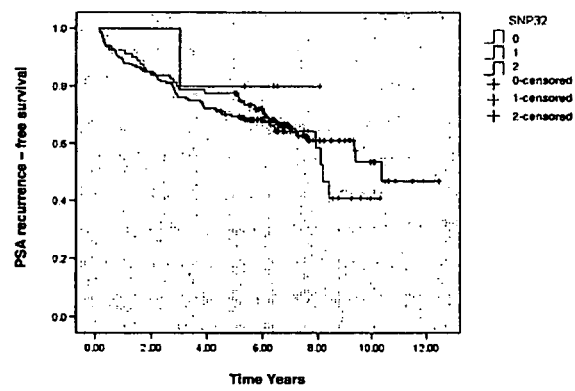
Figure 21B:
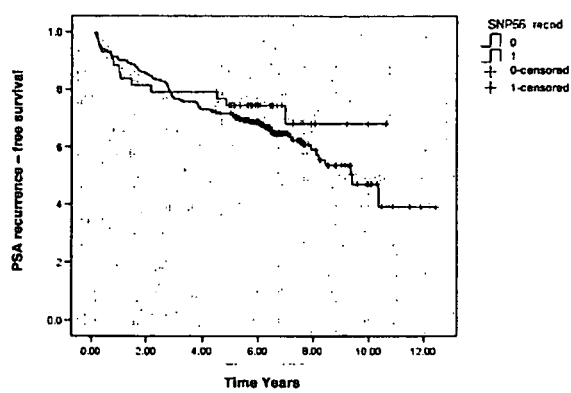

Survival analysis confirmed an impact of patients' genotypes and PCa progression, as the Kaplan-Meier curves show (FIGS. 8-17 and 19-21). For the SNPs that are in the models, SNP 24, 25 and 46 were found to be significant by using Log Rank test or Breslow or Tarone Ware ($p<0.05$), whilst for the others a positive trend was observed even if the difference did not reach significance Discussion To date several nomograms have been developed to predict the probability of biochemical progression after radical prostatectomy for localized prostate cancer. Those nomograms are usually based on classical clinical parameters such as PSA level, gleason grade or clinical stage. Those nomograms have failed to accurately predict PSA recurrence. Consequently, nomograms including novel markers that are particularly associated to PCa aggressiveness are urgently needed. In our study we describe four new nomograms or models. The new models add genetic markers (germline SNPs) to the standard clinical predictors. Those SNPs were already associated to PCa and our study demonstrate their usefulness as predictors of biologically aggressive PCa and progression as Likelihood Ratio (LR) values of the models indicate. LR is an accurate and practical way of expressing the power of diagnostic tests. Three of the four models described herein present a significantly high LR value (LR>5), thus evidencing the capacity of the methods (based on SNP combinations plus clinical data) to predict aggressive PCa phenotype. The high ROC-AUCs obtained for some of these models (>0.8) provides further evidence for the high discriminatory power of the predictors combinations used. The usefulness of the ROC-AUC magnitude as a tool for evaluating the strength of the relationship between predictors and disease has been described previously.

Using these SNPs to obtain a genetic profile of the patient provides an extra tool for the physician to differentiate patients with high probability of early PSA progression after surgery. Moreover, individual impact of germline genetic markers on cancer behaviour was verified by the survival analysis that considered PSA recurrence (0.4 ng/ml) as the final event.

In the case of model 1 we did not obtain a high LR, probably because of the low reliability of 0.2 ng/ml PSA threshold and low predictive capacity of pre-operative clinical data. Within the three last models Model 4 showed the best predictive power (LR=8.8, $R^2$=0.38, ROC-AUC=0.83, specificity=95% and sensibility=42%). This could be due to 0.4 ng/ml PSA recurrence threshold robustness, the high predictive capacity of post-operative clinical data and mainly to the fact of including up to four novel genetic markers (SNPs). The new model could help to identify patients undergoing surgery with high risk of biochemical recurrence who may benefit from neoadjuvant treatment protocols.

| Gene | Symbol | Reference |
| --- | --- | --- |
| Alpha 5 -reductase type II gene | SRD5A2 | J Urol 2003, 169(4, Suppl.): Abst 313.<br>J Urol. 2003 169(6): 2378-81<br>Prostate 2004 59(1): 69-76<br>Eur J Hum Genet. 2004 12(4): 321-32<br>Prostate 2002 52(4): 269-78.<br>Pharmacogenetics. 2002 12(4): 307-12. |
| Androgen receptor | AR | Prostate. 2004 60(4): 343-51.<br>Int J Radiat Oncol Biol Phys 2002, 54 Abst 232<br>Hum Genet. 2002; 110(2): 122-9<br>Lab Invest. 2003 83(12): 1709-13<br>Lab Invest. 2002 82(11): 1591-8<br>Cancer Res. 2004; 64(2): 765-71<br>Cancer Res. 2003 Jan. 1; 63(1): 149-53<br>Int J Cancer. 2002 Jul. 20; 100(3): 309-17<br>Cancer Genet Cytogenet. 2003 March; 141(2): 91-6<br>Int J Urol. 2002 9(10): 545-53<br>Urol Int. 2002; 68(1): 16-23.<br>J Urol. 2002 168(5): 2245-8.<br>Clin Cancer Res. 2001 7(10): 3092-6. |
| Angiotensin-converting enzyme | ACE | J Pathol. 2004 202(3): 330-5 |
| Ataxia telangiectasia mutated | ATM | Br J Cancer. 2004 91(4): 783-7 |
| B-cell CLL/lymphoma 2, transcript variant 1 | BCL2 | 53rd Annu Meet Am Soc Hum Genet (Nov 4-Nov 8, Los Angeles) 2003, Abst 457 |
| Beta-17-hydroxysteroid dehydrogenase | HSD17B3 | Prostate. 2002 Sep. 15; 53(1): 65-8 |
| Beta-3-hydroxysteroid dehydrogenase B1 | HSD3B1 | Cancer Res. 2002 Mar. 15; 62(6): 1784-9. |
| Beta-3-hydroxysteroid | HSD3B2 | Cancer Res. 2002 Mar. 15; 62(6): 1784-9. |

| Gene | Symbol | Reference |
|---|---|---|
| dehydrogenases B2 | | |
| Breast Cancer 2 | BRCA2 | Am J Hum Genet. 2003. 72(1): 1-12. |
| Cadherin 1, type 1, E-cadherin | CDH1 | J Urol 2002, 167(4, Suppl.): Abst 284<br>Int J Cancer. 2004 109(3): 348-52<br>Int J Cancer. 2002 100(6): 683-5<br>Clin Cancer Res. 2001 7(11): 3465-71. |
| Collagen alpha1 type XVIII (contains endostatin) | COL18A1 | Proc Am Assoc Cancer Res 2003, 44:<br>Abst 4054 Cancer Res. 2001; 61(20): 7375-8. |
| Cyclin D1 parathyroid adenomatosis 1 | CD1 | Jpn J Cancer Res 2002, 93(Suppl.): Abst 3245<br>J Urol 2003, 169(4, Suppl.): Abst 209<br>Anticancer Res. 2003 23(6D): 4947-5<br>Int J Cancer. 2003 103(1): 116-20. |
| Cyclin dependant Kinase 1A | CDKN1A | Cancer Res. 2003 63(9): 2033-6. |
| Cyclin dependant Kinase 1B | CDKN1B | Cancer Res. 2004. 64(6): 1997-9<br>Cancer Res. 2003 63(9): 2033-6 |
| Cyclin-dependent kinase inhibitor 1B (p27, Kip1) gene | CDKNI1B | Cancer Res 2004, 64(6): 1997 |
| Cytochrome P450, family 1, subfamily A, polypeptide 1 | CYP1A1 | Cancer Genet Cytogenet. 2004 154(1): 81-5. |
| Cytochrome P450, family 1, subfamily B, polypeptide 1 | CYP1B1 | Br J Cancer 2003, 89(8): 1524<br>Biochem Biophys Res C. 2002 296(4): 820-6.<br>Anticancer Res. 2004 24(4): 2431-7 |
| Cytochrome P450, family 19, intron 4 | CYP19 | Anticancer Res. 2003 23(6D):<br>4941-6 Cancer. 2003 98(7): 1411-6<br>Clin Cancer Res. 2001 7(10): 3092-6. |
| Cytochrome P450, family 2, subfamily C, polypeptide 19 | CYP2C19 | Cancer Biol Ther. 2002 1(6): 669-73 |
| Cytochrome P450, family 3, subfamily A, polypeptide 4 | CYP3A4 | Br J Cancer 2003, 88(6)<br>Eur J Hum Genet. 2004 12(4): 321-32<br>Oncol Rep. 2002; 9(3): 653-5.<br>J Urol 2003, 169(4, Suppl.): Abst 1442<br>Cancer. 2003 Nov. 1; 98(9): 1855-62.<br>Cancer Res. 2004 Oct. 15; 64(20): 7426-31 |
| Cytochrome P450, family 7, subfamily B, polypeptide 1 | CYP7B1 | Pharmacogenomics J. 2004; 4(4): 245-50. |
| Cytochrome P450, subfamily 17 | CYP17 | J Urol 2003, 169(4, Suppl.): Abst 313<br>Eur J Hum Genet. 2004 12(4): 321-32<br>Cancer Epidemiol Biomarkers Prev. 2003.<br>12(2): 120-6,<br>J Urol 2002, 167(4, Suppl.): Abst 583 |
| CHK2 checkpoint homolog (isoform 1) (S. pombe) | CHEK2 | Am J Hum Genet 2003, 72(2): 270,<br>Cancer Res 2004, 64(8): 2677 |
| Early growth response-1 gene | EGR1 | Am J Clin Oncol. 2001 October; 24(5): 500-5. |
| ElaC homolog 2 | ELAC2 | Prostate. 2004 61(3): 248-52<br>Cancer Epidemiol Biomarkers Prev.<br>2003. 12(9): 876-81<br>Int J Cancer. 2003 Nov. 1; 107(2): 224-8. |
| Endothelial nitric oxide synthase | NOS | Cancer Lett. 2003 Jan. 10; 189(1): 85-90.<br>Clin Cancer Res. 2002 8(11): 3433-7 |
| Epoxide hydrolase 1, microsomal | EPHX | Isr Med Assoc J. 2003 October; 5(10): 741-5. |
| Estrogen receptor | ESR1 | Cancer Genet Cytogenet. 2003 March; 141(2): 91-6. |
| Estrogen receptor 1 | ESR1 | J Urol 2003, 169(4, Suppl.): Abst 316<br>Cancer. 2003 98(7): 1411-6.<br>Eur Urol. 2003 October; 44(4): 487-90.<br>Mol Carcinog. 2003 37(4): 202-8.<br>Clin Cancer Res. 2001 7(10): 3092-6. |
| Fibroblast growth factor receptor-4 | FGFR4 | Clin Cancer Res. 2004. 10: 6169-78 |
| Glutathione S-transferase M3 | GSTM3 | Prostate. 2004 Mar. 1; 58(4): 414-20 |
| Glutathione-S-transferases | GST | Indian J Cancer. 2004. 41(3): 115-9. |
| Human oxoguanine glycosylase 1 | OGG1 | J Urol. 2003 170(6 Pt 1): 2471-4<br>Cancer Res. 2002 Apr. 15; 62(8): 2253-7. |
| Human sulfotransferase 1A1 | SULT1A1 | Cancer Epidemiol Biomarkers Prev. 2004 13(2): 270-6 |
| Hypoxia inducible factor-1alpha (HIF-1 alpha). | HIF1 | J Cancer Res Clin Oncol. 2002 128(7): 358-62 |

| Gene | Symbol | Reference |
| --- | --- | --- |
| Hypoxia-inducible factor 1, alpha subunit, transcript variant 1 | HIF1 | J Urol 2002, 167(4, Suppl.): Abst 201 |
| Insulin gene | INS | Br J Cancer. 2003 88(2): 263-9 |
| Insulin-like growth factor-binding protein3 | IGFBP3 | Cancer Res. 2003 63(15): 4407-11 |
| Kallikrein 10 | KLK10 | Prostate 2002, 51(1): 35 |
| Kallikrein-2 | KLK2 | J Clin Oncol. 2003 21(12): 2312-9. |
| Leptin | LEP | Prostate. 2004 59(3): 268-74. |
| Lipoprotein lipase | LPL | Int J Cancer. 2004 112(5): 872-6. |
| Macrophage scavenger receptor 1 | MSR1 | Prostate. 2004 59(2): 132-40. |
| Macrophage-inhibitory cytokine-1 | MIC1 | J Natl Cancer Inst. 2004 96(16): 1248-54. |
| Methylenetetrahydrofolate reductase | MTHFR | Int J Oncol. 2004 25(5): 1465-71 |
| N-acetyltransferase-2 | NAT2 | Int J Urol. 2003 March; 10(3): 167-73. Environ Mol Mutagen. 2002; 40(3): 161-7. |
| Osteocalcin | BGLAP | Eur Urol. 2003 February; 43(2): 197-200 |
| P53 tumor supressor | P53 | Urol Int. 2004; 73(1): 41-6 |
| Paraoxonase | PON1 | J Natl Cancer Inst. 2003 95(11): 812-8. |
| Prostate specific antigen | PSA | J Urol. 2004 171(4): 1529-32 |
| PSA gene | | Prostate. 2002; 53(1): 88-94 |
| RNAse L | RNASEL | Br J Cancer. 2003 89(4): 691-6. J Med Genet. 2003 40(3): e21. |
| TGFbeta1 | TGFB1 | Cancer Epidemiol Biomarkers Prev. 2004. 13(5): 759-64 Carcinogenesis. 2004. 25(2): 237-40. |
| Toll-like receptor 4 | TLR4 | Cancer Res. 2004 64(8): 2918-22. |
| Transmembrane serine protease 2 | TMPRSS2 | Prostate. 2004 59(4): 357-9 |
| UDP-glucuronosyl-transferase | UGT2B15 | J Urol. 2004 171(6): 2484-8. Prostate. 2004. 59(4): 436-9 |
| Vascular endothelial growth factor | VEGF | Urology. 2003 62(2): 374-7. Cancer Res. 2002 Jun. 15; 62(12): 3369-72 |
| v-erb-b2 erythroblastic leukemia vir oncogene | HER2 | Prostate. 2004 |
| Interleukin-6 | IL6 | J Urology. 2005 174: 753-756 |
| Vitamin D Receptor | VDR | Br J Cancer 2003, 88(6): 928 Cancer Epidemiol Biomarkers Prev. 2003. 12(1): 23-7. J Hum Genet. 2002; 47(8): 413-8 Urol Int. 2002; 68(4): 226-31 Endocr J. 2001 48(5): 543-9 |

The invention claimed is:

1. A method of treating a human post-operative prostate cancer subject, comprising:
 (a) (i) detecting in a DNA sample obtained from the subject the presence of at least one T allele of the rs198977 single nucleotide polymorphism, wherein said detecting comprises sequencing the DNA sample or contacting the DNA sample with a probe that binds specifically to the T allele and not the C allele of the rs198977 single nucleotide polymorphism; and
  (ii) correlating the presence of the T allele of the rs198977 single nucleotide polymorphism with an increased risk of prostate cancer recurrence in the subject; and
 (b) administering adjuvant therapy to the subject with increased risk of prostate cancer recurrence, wherein said adjuvant therapy comprises radiation, chemotherapy and/or androgen-deprivation therapy.

2. A method of treating a human pre-operative prostate cancer subject, comprising:
 (a) (i) detecting in a DNA sample obtained from the subject the presence of at least one T allele of the rs198977 single nucleotide polymorphism, wherein said detecting comprises sequencing the DNA sample or contacting the DNA sample with a probe that binds specifically to the T allele and not the C allele of the rs198977 single nucleotide polymorphism; and
  (ii) correlating the presence of the T allele of the rs198977 single nucleotide polymorphism with an increased risk of prostate cancer recurrence in the subject; and
 (b) administering therapy without surgery to the subject with increased risk of prostate cancer recurrence, wherein said therapy without surgery comprises radiation, chemotherapy and/or androgen-deprivation therapy.

3. A method for identifying a human subject having an increased risk of prostate cancer recurrence, comprising:
 detecting in a DNA sample obtained from the subject the presence of at least one T allele of the rs198977 single nucleotide polymorphism by amplifying a portion of the DNA sample with nucleic acid primers comprising SEQ ID NO: 369 and SEQ ID NO: 458; and
 correlating the presence of the T allele of the rs198977 single nucleotide polymorphism with an increased risk of prostate cancer recurrence in the subject.

4. The method of claim 3, wherein said method comprises detecting two T alleles of the subject at the rs198977 single nucleotide polymorphism.

5. The method of claim 3, wherein the method further comprises obtaining or determining one or more clinical variables selected from the group consisting of prostate specific antigen level, onset age, clinical stage, prostatectomy Gleason grade, surgical oncologic margins, and surgical gland margins.

6. The method of claim 3, wherein the increased risk of prostate cancer recurrence comprises increased risk of prostate cancer recurrence within 5 years of said subject having had prostatectomy surgery.

7. The method of claim 3, wherein the DNA sample from the subject has been obtained from blood, saliva, liver, kidney, pancreas, heart, urine or from cells from the buccal cavity of the subject.

8. The method of claim 7, wherein said blood comprises serum, lymphocytes, lymphoblastoid cells, fibroblasts, platelets, mononuclear cells or other blood cells.

* * * * *

SEQUENCE LISTING

<160> NUMBER OF SEQ ID NOS: 543

<210> SEQ ID NO 1
<211> LENGTH: 23
<212> TYPE: DNA
<213> ORGANISM: Homo sapiens

<400> SEQUENCE: 1
gctgggagaa cagggtacga taa                                          23

<210> SEQ ID NO 2
<211> LENGTH: 23
<212> TYPE: DNA
<213> ORGANISM: Homo sapiens

<400> SEQUENCE: 2
gctgggagaa cggggtacga taa                                          23

<210> SEQ ID NO 3
<211> LENGTH: 23
<212> TYPE: DNA
<213> ORGANISM: Homo sapiens

```
<400> SEQUENCE: 3
ttatcgtacc ctgttctccc agc                                            23

<210> SEQ ID NO 4
<211> LENGTH: 23
<212> TYPE: DNA
<213> ORGANISM: Homo sapiens

<400> SEQUENCE: 4
ttatcgtacc ccgttctccc agc                                            23

<210> SEQ ID NO 5
<211> LENGTH: 21
<212> TYPE: DNA
<213> ORGANISM: Homo sapiens

<400> SEQUENCE: 5
gggttcgggc cgcgtagggg c                                              21

<210> SEQ ID NO 6
<211> LENGTH: 21
<212> TYPE: DNA
<213> ORGANISM: Homo sapiens

<400> SEQUENCE: 6
gggttcgggc tgcgtagggg c                                              21

<210> SEQ ID NO 7
<211> LENGTH: 21
<212> TYPE: DNA
<213> ORGANISM: Homo sapiens

<400> SEQUENCE: 7
gcccctacgc ggcccgaacc c                                              21

<210> SEQ ID NO 8
<211> LENGTH: 21
<212> TYPE: DNA
<213> ORGANISM: Homo sapiens

<400> SEQUENCE: 8
gcccctacgc agcccgaacc c                                              21

<210> SEQ ID NO 9
<211> LENGTH: 23
<212> TYPE: DNA
<213> ORGANISM: Homo sapiens

<400> SEQUENCE: 9
aaactcttac attgcataca tag                                            23

<210> SEQ ID NO 10
<211> LENGTH: 23
<212> TYPE: DNA
<213> ORGANISM: Homo sapiens

<400> SEQUENCE: 10
aaactcttac actgcataca tag                                            23

<210> SEQ ID NO 11
<211> LENGTH: 21
<212> TYPE: DNA
```

```
<213> ORGANISM: Homo sapiens

<400> SEQUENCE: 11
aactcttaca ttgcatacat a                                              21

<210> SEQ ID NO 12
<211> LENGTH: 21
<212> TYPE: DNA
<213> ORGANISM: Homo sapiens

<400> SEQUENCE: 12
aactcttaca ctgcatacat a                                              21

<210> SEQ ID NO 13
<211> LENGTH: 23
<212> TYPE: DNA
<213> ORGANISM: Homo sapiens

<400> SEQUENCE: 13
atcttccaaa tcattttag tta                                             23

<210> SEQ ID NO 14
<211> LENGTH: 23
<212> TYPE: DNA
<213> ORGANISM: Homo sapiens

<400> SEQUENCE: 14
atcttccaaa taattttag tta                                             23

<210> SEQ ID NO 15
<211> LENGTH: 21
<212> TYPE: DNA
<213> ORGANISM: Homo sapiens

<400> SEQUENCE: 15
tcttccaaat cattttagt t                                               21

<210> SEQ ID NO 16
<211> LENGTH: 21
<212> TYPE: DNA
<213> ORGANISM: Homo sapiens

<400> SEQUENCE: 16
tcttccaaat aattttagt t                                               21

<210> SEQ ID NO 17
<211> LENGTH: 23
<212> TYPE: DNA
<213> ORGANISM: Homo sapiens

<400> SEQUENCE: 17
ccttctacag cggtgccttc caa                                            23

<210> SEQ ID NO 18
<211> LENGTH: 23
<212> TYPE: DNA
<213> ORGANISM: Homo sapiens

<400> SEQUENCE: 18
ccttctacag cagtgccttc caa                                            23

<210> SEQ ID NO 19
<211> LENGTH: 23
```

<212> TYPE: DNA
<213> ORGANISM: Homo sapiens

<400> SEQUENCE: 19
ttggaaggca ccgctgtaga agg                                              23

<210> SEQ ID NO 20
<211> LENGTH: 23
<212> TYPE: DNA
<213> ORGANISM: Homo sapiens

<400> SEQUENCE: 20
ttggaaggca ctgctgtaga agg                                              23

<210> SEQ ID NO 21
<211> LENGTH: 23
<212> TYPE: DNA
<213> ORGANISM: Homo sapiens

<400> SEQUENCE: 21
gcacaaggag aacctgaagt cca                                              23

<210> SEQ ID NO 22
<211> LENGTH: 23
<212> TYPE: DNA
<213> ORGANISM: Homo sapiens

<400> SEQUENCE: 22
gcacaaggag accctgaagt cca                                              23

<210> SEQ ID NO 23
<211> LENGTH: 19
<212> TYPE: DNA
<213> ORGANISM: Homo sapiens

<400> SEQUENCE: 23
gacttcaggt tctccttgt                                                   19

<210> SEQ ID NO 24
<211> LENGTH: 19
<212> TYPE: DNA
<213> ORGANISM: Homo sapiens

<400> SEQUENCE: 24
gacttcaggg tctccttgt                                                   19

<210> SEQ ID NO 25
<211> LENGTH: 23
<212> TYPE: DNA
<213> ORGANISM: Homo sapiens

<400> SEQUENCE: 25
ccatttcccc tcttaaatga gaa                                              23

<210> SEQ ID NO 26
<211> LENGTH: 23
<212> TYPE: DNA
<213> ORGANISM: Homo sapiens

<400> SEQUENCE: 26
ccatttcccc tgttaaatga gaa                                              23

<210> SEQ ID NO 27

```
<211> LENGTH: 21
<212> TYPE: DNA
<213> ORGANISM: Homo sapiens

<400> SEQUENCE: 27
catttcccct cttaaatgag a                                                 21

<210> SEQ ID NO 28
<211> LENGTH: 21
<212> TYPE: DNA
<213> ORGANISM: Homo sapiens

<400> SEQUENCE: 28
catttcccct gttaaatgag a                                                 21

<210> SEQ ID NO 29
<211> LENGTH: 23
<212> TYPE: DNA
<213> ORGANISM: Homo sapiens

<400> SEQUENCE: 29
aagcctatgg cgccccgtgc gcg                                               23

<210> SEQ ID NO 30
<211> LENGTH: 23
<212> TYPE: DNA
<213> ORGANISM: Homo sapiens

<400> SEQUENCE: 30
aagcctatgg ctccccgtgc gcg                                               23

<210> SEQ ID NO 31
<211> LENGTH: 21
<212> TYPE: DNA
<213> ORGANISM: Homo sapiens

<400> SEQUENCE: 31
gcgcacgggg cgccataggc t                                                 21

<210> SEQ ID NO 32
<211> LENGTH: 21
<212> TYPE: DNA
<213> ORGANISM: Homo sapiens

<400> SEQUENCE: 32
gcgcacgggg agccataggc t                                                 21

<210> SEQ ID NO 33
<211> LENGTH: 23
<212> TYPE: DNA
<213> ORGANISM: Homo sapiens

<400> SEQUENCE: 33
gatccacttc cggtaatgca cca                                               23

<210> SEQ ID NO 34
<211> LENGTH: 23
<212> TYPE: DNA
<213> ORGANISM: Homo sapiens

<400> SEQUENCE: 34
gatccacttc cagtaatgca cca                                               23
```

```
<210> SEQ ID NO 35
<211> LENGTH: 21
<212> TYPE: DNA
<213> ORGANISM: Homo sapiens

<400> SEQUENCE: 35
atccacttcc ggtaatgcac c                                              21

<210> SEQ ID NO 36
<211> LENGTH: 21
<212> TYPE: DNA
<213> ORGANISM: Homo sapiens

<400> SEQUENCE: 36
atccacttcc agtaatgcac c                                              21

<210> SEQ ID NO 37
<211> LENGTH: 19
<212> TYPE: DNA
<213> ORGANISM: Homo sapiens

<400> SEQUENCE: 37
acgtccatca tctctgcgg                                                 19

<210> SEQ ID NO 38
<211> LENGTH: 19
<212> TYPE: DNA
<213> ORGANISM: Homo sapiens

<400> SEQUENCE: 38
acgtccatcg tctctgcgg                                                 19

<210> SEQ ID NO 39
<211> LENGTH: 21
<212> TYPE: DNA
<213> ORGANISM: Homo sapiens

<400> SEQUENCE: 39
gacgtccatc atctctgcgg t                                              21

<210> SEQ ID NO 40
<211> LENGTH: 21
<212> TYPE: DNA
<213> ORGANISM: Homo sapiens

<400> SEQUENCE: 40
gacgtccatc gtctctgcgg t                                              21

<210> SEQ ID NO 41
<211> LENGTH: 23
<212> TYPE: DNA
<213> ORGANISM: Homo sapiens

<400> SEQUENCE: 41
tgcctagtgg gttcacctgc cca                                            23

<210> SEQ ID NO 42
<211> LENGTH: 23
<212> TYPE: DNA
<213> ORGANISM: Homo sapiens

<400> SEQUENCE: 42
tgcctagtgg ggtcacctgc cca                                            23
```

```
<210> SEQ ID NO 43
<211> LENGTH: 25
<212> TYPE: DNA
<213> ORGANISM: Homo sapiens

<400> SEQUENCE: 43
ctgcctagtg ggttcacctg cccac                                          25

<210> SEQ ID NO 44
<211> LENGTH: 25
<212> TYPE: DNA
<213> ORGANISM: Homo sapiens

<400> SEQUENCE: 44
ctgcctagtg gggtcacctg cccac                                          25

<210> SEQ ID NO 45
<211> LENGTH: 25
<212> TYPE: DNA
<213> ORGANISM: Homo sapiens

<400> SEQUENCE: 45
cacacattct tggccttctg cagat                                          25

<210> SEQ ID NO 46
<211> LENGTH: 25
<212> TYPE: DNA
<213> ORGANISM: Homo sapiens

<400> SEQUENCE: 46
cacacattct tgaccttctg cagat                                          25

<210> SEQ ID NO 47
<211> LENGTH: 25
<212> TYPE: DNA
<213> ORGANISM: Homo sapiens

<400> SEQUENCE: 47
atctgcagaa ggccaagaat gtgtg                                          25

<210> SEQ ID NO 48
<211> LENGTH: 25
<212> TYPE: DNA
<213> ORGANISM: Homo sapiens

<400> SEQUENCE: 48
atctgcagaa ggtcaagaat gtgtg                                          25

<210> SEQ ID NO 49
<211> LENGTH: 25
<212> TYPE: DNA
<213> ORGANISM: Homo sapiens

<400> SEQUENCE: 49
aatcatgacc cactgaagtg gccta                                          25

<210> SEQ ID NO 50
<211> LENGTH: 25
<212> TYPE: DNA
<213> ORGANISM: Homo sapiens

<400> SEQUENCE: 50
aatcatgacc cagtgaagtg gccta                                          25
```

<210> SEQ ID NO 51
<211> LENGTH: 25
<212> TYPE: DNA
<213> ORGANISM: Homo sapiens

<400> SEQUENCE: 51
taggccactt cagtgggtca tgatt                                        25

<210> SEQ ID NO 52
<211> LENGTH: 25
<212> TYPE: DNA
<213> ORGANISM: Homo sapiens

<400> SEQUENCE: 52
taggccactt cactgggtca tgatt                                        25

<210> SEQ ID NO 53
<211> LENGTH: 23
<212> TYPE: DNA
<213> ORGANISM: Homo sapiens

<400> SEQUENCE: 53
gagcatggcg gcattggcgc agg                                          23

<210> SEQ ID NO 54
<211> LENGTH: 23
<212> TYPE: DNA
<213> ORGANISM: Homo sapiens

<400> SEQUENCE: 54
gagcatggcg ggattggcgc agg                                          23

<210> SEQ ID NO 55
<211> LENGTH: 23
<212> TYPE: DNA
<213> ORGANISM: Homo sapiens

<400> SEQUENCE: 55
cctgcgccaa tgccgccatg ctc                                          23

<210> SEQ ID NO 56
<211> LENGTH: 23
<212> TYPE: DNA
<213> ORGANISM: Homo sapiens

<400> SEQUENCE: 56
cctgcgccaa tcccgccatg ctc                                          23

<210> SEQ ID NO 57
<211> LENGTH: 23
<212> TYPE: DNA
<213> ORGANISM: Homo sapiens

<400> SEQUENCE: 57
ggcggcgcgg gctggcaggc ggg                                          23

<210> SEQ ID NO 58
<211> LENGTH: 23
<212> TYPE: DNA
<213> ORGANISM: Homo sapiens

<400> SEQUENCE: 58
ggcggcgcgg gttggcaggc ggg                                                          23

<210> SEQ ID NO 59
<211> LENGTH: 21
<212> TYPE: DNA
<213> ORGANISM: Homo sapiens

<400> SEQUENCE: 59
ccgcctgcca gcccgcgccg c                                                            21

<210> SEQ ID NO 60
<211> LENGTH: 21
<212> TYPE: DNA
<213> ORGANISM: Homo sapiens

<400> SEQUENCE: 60
ccgcctgcca acccgcgccg c                                                            21

<210> SEQ ID NO 61
<211> LENGTH: 21
<212> TYPE: DNA
<213> ORGANISM: Homo sapiens

<400> SEQUENCE: 61
cctcttctgc gtacattact t                                                            21

<210> SEQ ID NO 62
<211> LENGTH: 21
<212> TYPE: DNA
<213> ORGANISM: Homo sapiens

<400> SEQUENCE: 62
cctcttctgc ctacattact t                                                            21

<210> SEQ ID NO 63
<211> LENGTH: 23
<212> TYPE: DNA
<213> ORGANISM: Homo sapiens

<400> SEQUENCE: 63
gaagtaatgt acgcagaaga ggc                                                          23

<210> SEQ ID NO 64
<211> LENGTH: 23
<212> TYPE: DNA
<213> ORGANISM: Homo sapiens

<400> SEQUENCE: 64
gaagtaatgt aggcagaaga ggc                                                          23

<210> SEQ ID NO 65
<211> LENGTH: 21
<212> TYPE: DNA
<213> ORGANISM: Homo sapiens

<400> SEQUENCE: 65
ccccagatga gcccccagaa c                                                            21

<210> SEQ ID NO 66
<211> LENGTH: 21
<212> TYPE: DNA
<213> ORGANISM: Homo sapiens

<400> SEQUENCE: 66

```
ccccagatga tcccccagaa c                                              21

<210> SEQ ID NO 67
<211> LENGTH: 23
<212> TYPE: DNA
<213> ORGANISM: Homo sapiens

<400> SEQUENCE: 67
agttctgggg gctcatctgg ggc                                            23

<210> SEQ ID NO 68
<211> LENGTH: 23
<212> TYPE: DNA
<213> ORGANISM: Homo sapiens

<400> SEQUENCE: 68
agttctgggg gatcatctgg ggc                                            23

<210> SEQ ID NO 69
<211> LENGTH: 23
<212> TYPE: DNA
<213> ORGANISM: Homo sapiens

<400> SEQUENCE: 69 tgagggcat ggggacgggg ttc                                             23

<210> SEQ ID NO 70
<211> LENGTH: 23
<212> TYPE: DNA
<213> ORGANISM: Homo sapiens

<400> SEQUENCE: 70 tgagggcat gaggacgggg ttc                                             23

<210> SEQ ID NO 71
<211> LENGTH: 23
<212> TYPE: DNA
<213> ORGANISM: Homo sapiens

<400> SEQUENCE: 71
gaaccccgtc cccatgcccc tca                                            23

<210> SEQ ID NO 72
<211> LENGTH: 23
<212> TYPE: DNA
<213> ORGANISM: Homo sapiens

<400> SEQUENCE: 72
gaaccccgtc ctcatgcccc tca                                            23

<210> SEQ ID NO 73
<211> LENGTH: 23
<212> TYPE: DNA
<213> ORGANISM: Homo sapiens

<400> SEQUENCE: 73
accaaagcat ctgggatggc cct                                            23

<210> SEQ ID NO 74
<211> LENGTH: 23
<212> TYPE: DNA
<213> ORGANISM: Homo sapiens
```

```
<400> SEQUENCE: 74
accaaagcat ccgggatggc cct                                              23

<210> SEQ ID NO 75
<211> LENGTH: 23
<212> TYPE: DNA
<213> ORGANISM: Homo sapiens

<400> SEQUENCE: 75
agggccatcc cagatgcttt ggt                                              23

<210> SEQ ID NO 76
<211> LENGTH: 23
<212> TYPE: DNA
<213> ORGANISM: Homo sapiens

<400> SEQUENCE: 76
accaaagcat ccgggatggc cct                                              23

<210> SEQ ID NO 77
<211> LENGTH: 23
<212> TYPE: DNA
<213> ORGANISM: Homo sapiens

<400> SEQUENCE: 77
gtaggctgat ccttattcaa aat                                              23

<210> SEQ ID NO 78
<211> LENGTH: 23
<212> TYPE: DNA
<213> ORGANISM: Homo sapiens

<400> SEQUENCE: 78
gtaggctgat cgttattcaa aat                                              23

<210> SEQ ID NO 79
<211> LENGTH: 23
<212> TYPE: DNA
<213> ORGANISM: Homo sapiens

<400> SEQUENCE: 79
attttgaata aggatcagcc tac                                              23

<210> SEQ ID NO 80
<211> LENGTH: 23
<212> TYPE: DNA
<213> ORGANISM: Homo sapiens

<400> SEQUENCE: 80
attttgaata acgatcagcc tac                                              23

<210> SEQ ID NO 81
<211> LENGTH: 23
<212> TYPE: DNA
<213> ORGANISM: Homo sapiens

<400> SEQUENCE: 81
tctttaaggg gtctgtcatg gaa                                              23

<210> SEQ ID NO 82
<211> LENGTH: 23
<212> TYPE: DNA
<213> ORGANISM: Homo sapiens
```

```
<400> SEQUENCE: 82
tctttaaggg ggctgtcatg gaa                                           23

<210> SEQ ID NO 83
<211> LENGTH: 23
<212> TYPE: DNA
<213> ORGANISM: Homo sapiens

<400> SEQUENCE: 83
ttccatgaca gacccccttaa aga                                          23

<210> SEQ ID NO 84
<211> LENGTH: 23
<212> TYPE: DNA
<213> ORGANISM: Homo sapiens

<400> SEQUENCE: 84
ttccatgaca gcccccttaa aga                                           23

<210> SEQ ID NO 85
<211> LENGTH: 23
<212> TYPE: DNA
<213> ORGANISM: Homo sapiens

<400> SEQUENCE: 85
tgctgctggc cgggctgtat cga                                           23

<210> SEQ ID NO 86
<211> LENGTH: 23
<212> TYPE: DNA
<213> ORGANISM: Homo sapiens

<400> SEQUENCE: 86
tgctgctggc caggctgtat cga                                           23

<210> SEQ ID NO 87
<211> LENGTH: 23
<212> TYPE: DNA
<213> ORGANISM: Homo sapiens

<400> SEQUENCE: 87
tcgatacagc ccggccagca gca                                           23

<210> SEQ ID NO 88
<211> LENGTH: 23
<212> TYPE: DNA
<213> ORGANISM: Homo sapiens

<400> SEQUENCE: 88
tcgatacagc ctggccagca gca                                           23

<210> SEQ ID NO 89
<211> LENGTH: 23
<212> TYPE: DNA
<213> ORGANISM: Homo sapiens

<400> SEQUENCE: 89
tggaattggg gatcactgga agt                                           23

<210> SEQ ID NO 90
<211> LENGTH: 23
<212> TYPE: DNA
```

<213> ORGANISM: Homo sapiens

<400> SEQUENCE: 90
tggaattggg ggtcactgga agt        23

<210> SEQ ID NO 91
<211> LENGTH: 23
<212> TYPE: DNA
<213> ORGANISM: Homo sapiens

<400> SEQUENCE: 91
acttccagtg atccccaatt cca        23

<210> SEQ ID NO 92
<211> LENGTH: 23
<212> TYPE: DNA
<213> ORGANISM: Homo sapiens

<400> SEQUENCE: 92
acttccagtg accccccaatt cca        23

<210> SEQ ID NO 93
<211> LENGTH: 23
<212> TYPE: DNA
<213> ORGANISM: Homo sapiens

<400> SEQUENCE: 93
gaataagaag tcaggctggt gag        23

<210> SEQ ID NO 94
<211> LENGTH: 23
<212> TYPE: DNA
<213> ORGANISM: Homo sapiens

<400> SEQUENCE: 94
gaataagaag tgaggctggt gag        23

<210> SEQ ID NO 95
<211> LENGTH: 23
<212> TYPE: DNA
<213> ORGANISM: Homo sapiens

<400> SEQUENCE: 95
ctcaccagcc tgacttctta ttc        23

<210> SEQ ID NO 96
<211> LENGTH: 23
<212> TYPE: DNA
<213> ORGANISM: Homo sapiens

<400> SEQUENCE: 96
ctcaccagcc tcacttctta ttc        23

<210> SEQ ID NO 97
<211> LENGTH: 23
<212> TYPE: DNA
<213> ORGANISM: Homo sapiens

<400> SEQUENCE: 97
ggctgctccc cgcgtggccc ctg        23

<210> SEQ ID NO 98
<211> LENGTH: 23

```
<212> TYPE: DNA
<213> ORGANISM: Homo sapiens

<400> SEQUENCE: 98
ggctgctccc cccgtggccc ctg                                              23

<210> SEQ ID NO 99
<211> LENGTH: 23
<212> TYPE: DNA
<213> ORGANISM: Homo sapiens

<400> SEQUENCE: 99
caggggccac gcggggagca gcc                                              23

<210> SEQ ID NO 100
<211> LENGTH: 23
<212> TYPE: DNA
<213> ORGANISM: Homo sapiens

<400> SEQUENCE: 100
caggggccac gggggagca gcc                                               23

<210> SEQ ID NO 101
<211> LENGTH: 23
<212> TYPE: DNA
<213> ORGANISM: Homo sapiens

<400> SEQUENCE: 101
ttctcaacag ataccctcac ttc                                              23

<210> SEQ ID NO 102
<211> LENGTH: 23
<212> TYPE: DNA
<213> ORGANISM: Homo sapiens

<400> SEQUENCE: 102
ttctcaacag acaccctcac ttc                                              23

<210> SEQ ID NO 103
<211> LENGTH: 23
<212> TYPE: DNA
<213> ORGANISM: Homo sapiens

<400> SEQUENCE: 103
gaagtgaggg tatctgttga gaa                                              23

<210> SEQ ID NO 104
<211> LENGTH: 23
<212> TYPE: DNA
<213> ORGANISM: Homo sapiens

<400> SEQUENCE: 104
gaagtgaggg tgtctgttga gaa                                              23

<210> SEQ ID NO 105
<211> LENGTH: 23
<212> TYPE: DNA
<213> ORGANISM: Homo sapiens

<400> SEQUENCE: 105
agactccgag ttgaatgaaa atg                                              23

<210> SEQ ID NO 106
```

```
<211> LENGTH: 23
<212> TYPE: DNA
<213> ORGANISM: Homo sapiens

<400> SEQUENCE: 106
agactccgag tcgaatgaaa atg                                              23

<210> SEQ ID NO 107
<211> LENGTH: 23
<212> TYPE: DNA
<213> ORGANISM: Homo sapiens

<400> SEQUENCE: 107
cattttcatt caactcggag tct                                              23

<210> SEQ ID NO 108
<211> LENGTH: 23
<212> TYPE: DNA
<213> ORGANISM: Homo sapiens

<400> SEQUENCE: 108
cattttcatt cgactcggag tct                                              23

<210> SEQ ID NO 109
<211> LENGTH: 23
<212> TYPE: DNA
<213> ORGANISM: Homo sapiens

<400> SEQUENCE: 109
gcaccctggc tgctgtgttt gtg                                              23

<210> SEQ ID NO 110
<211> LENGTH: 23
<212> TYPE: DNA
<213> ORGANISM: Homo sapiens

<400> SEQUENCE: 110
gcaccctggc tactgtgttt gtg                                              23

<210> SEQ ID NO 111
<211> LENGTH: 23
<212> TYPE: DNA
<213> ORGANISM: Homo sapiens

<400> SEQUENCE: 111
cacaaacaca gcagccaggg tgc                                              23

<210> SEQ ID NO 112
<211> LENGTH: 23
<212> TYPE: DNA
<213> ORGANISM: Homo sapiens

<400> SEQUENCE: 112
cacaaacaca gtagccaggg tgc                                              23

<210> SEQ ID NO 113
<211> LENGTH: 23
<212> TYPE: DNA
<213> ORGANISM: Homo sapiens

<400> SEQUENCE: 113
aaagtggtcc acgaggattt cca                                              23
```

```
<210> SEQ ID NO 114
<211> LENGTH: 23
<212> TYPE: DNA
<213> ORGANISM: Homo sapiens

<400> SEQUENCE: 114
aaagtggtcc atgaggattt cca                                              23

<210> SEQ ID NO 115
<211> LENGTH: 23
<212> TYPE: DNA
<213> ORGANISM: Homo sapiens

<400> SEQUENCE: 115
tggaaatcct cgtggaccac ttt                                              23

<210> SEQ ID NO 116
<211> LENGTH: 23
<212> TYPE: DNA
<213> ORGANISM: Homo sapiens

<400> SEQUENCE: 116
tggaaatcct catggaccac ttt                                              23

<210> SEQ ID NO 117
<211> LENGTH: 23
<212> TYPE: DNA
<213> ORGANISM: Homo sapiens

<400> SEQUENCE: 117
gctgagcccc ccatactcta ttc                                              23

<210> SEQ ID NO 118
<211> LENGTH: 23
<212> TYPE: DNA
<213> ORGANISM: Homo sapiens

<400> SEQUENCE: 118
gctgagcccc cgatactcta ttc                                              23

<210> SEQ ID NO 119
<211> LENGTH: 23
<212> TYPE: DNA
<213> ORGANISM: Homo sapiens

<400> SEQUENCE: 119
gaatagagta tggggggctc agc                                              23

<210> SEQ ID NO 120
<211> LENGTH: 23
<212> TYPE: DNA
<213> ORGANISM: Homo sapiens

<400> SEQUENCE: 120
gaatagagta tcggggctc agc                                               23

<210> SEQ ID NO 121
<211> LENGTH: 23
<212> TYPE: DNA
<213> ORGANISM: Homo sapiens

<400> SEQUENCE: 121
tcggtgagac cattgcccgc tgg                                              23
```

```
<210> SEQ ID NO 122
<211> LENGTH: 23
<212> TYPE: DNA
<213> ORGANISM: Homo sapiens

<400> SEQUENCE: 122
tcggtgagac cgttgcccgc tgg                                              23

<210> SEQ ID NO 123
<211> LENGTH: 23
<212> TYPE: DNA
<213> ORGANISM: Homo sapiens

<400> SEQUENCE: 123
ccagcgggca atggtctcac cga                                              23

<210> SEQ ID NO 124
<211> LENGTH: 23
<212> TYPE: DNA
<213> ORGANISM: Homo sapiens

<400> SEQUENCE: 124
ccagcgggca acggtctcac cga                                              23

<210> SEQ ID NO 125
<211> LENGTH: 21
<212> TYPE: DNA
<213> ORGANISM: Homo sapiens

<400> SEQUENCE: 125
catccttcag atgtactcat c                                                21

<210> SEQ ID NO 126
<211> LENGTH: 21
<212> TYPE: DNA
<213> ORGANISM: Homo sapiens

<400> SEQUENCE: 126
catccttcag gtgtactcat c                                                21

<210> SEQ ID NO 127
<211> LENGTH: 21
<212> TYPE: DNA
<213> ORGANISM: Homo sapiens

<400> SEQUENCE: 127
gatgagtaca tctgaaggat g                                                21

<210> SEQ ID NO 128
<211> LENGTH: 21
<212> TYPE: DNA
<213> ORGANISM: Homo sapiens

<400> SEQUENCE: 128
gatgagtaca cctgaaggat g                                                21

<210> SEQ ID NO 129
<211> LENGTH: 23
<212> TYPE: DNA
<213> ORGANISM: Homo sapiens

<400> SEQUENCE: 129
agagcgaggg aagcctcggg ggc                                              23
```

<210> SEQ ID NO 130
<211> LENGTH: 23
<212> TYPE: DNA
<213> ORGANISM: Homo sapiens

<400> SEQUENCE: 130
agagcgaggg aggcctcggg ggc                                        23

<210> SEQ ID NO 131
<211> LENGTH: 23
<212> TYPE: DNA
<213> ORGANISM: Homo sapiens

<400> SEQUENCE: 131
gcccccgagg cttccctcgc tct                                        23

<210> SEQ ID NO 132
<211> LENGTH: 23
<212> TYPE: DNA
<213> ORGANISM: Homo sapiens

<400> SEQUENCE: 132
gcccccgagg cctccctcgc tct                                        23

<210> SEQ ID NO 133
<211> LENGTH: 23
<212> TYPE: DNA
<213> ORGANISM: Homo sapiens

<400> SEQUENCE: 133
tgaatttgcc caaaatgtcc tgt                                        23

<210> SEQ ID NO 134
<211> LENGTH: 23
<212> TYPE: DNA
<213> ORGANISM: Homo sapiens

<400> SEQUENCE: 134
tgaatttgcc cgaaatgtcc tgt                                        23

<210> SEQ ID NO 135
<211> LENGTH: 23
<212> TYPE: DNA
<213> ORGANISM: Homo sapiens

<400> SEQUENCE: 135
acaggacatt ttgggcaaat tca                                        23

<210> SEQ ID NO 136
<211> LENGTH: 23
<212> TYPE: DNA
<213> ORGANISM: Homo sapiens

<400> SEQUENCE: 136
acaggacatt tcgggcaaat tca                                        23

<210> SEQ ID NO 137
<211> LENGTH: 23
<212> TYPE: DNA
<213> ORGANISM: Homo sapiens

<400> SEQUENCE: 137
tcatttgagg agctgaaagc tca 23

<210> SEQ ID NO 138
<211> LENGTH: 23
<212> TYPE: DNA
<213> ORGANISM: Homo sapiens

<400> SEQUENCE: 138
tcatttgagg atctgaaagc tca 23

<210> SEQ ID NO 139
<211> LENGTH: 23
<212> TYPE: DNA
<213> ORGANISM: Homo sapiens

<400> SEQUENCE: 139
tgagctttca gctcctcaaa tga 23

<210> SEQ ID NO 140
<211> LENGTH: 23
<212> TYPE: DNA
<213> ORGANISM: Homo sapiens

<400> SEQUENCE: 140
tgagctttca gatcctcaaa tga 23

<210> SEQ ID NO 141
<211> LENGTH: 23
<212> TYPE: DNA
<213> ORGANISM: Homo sapiens

<400> SEQUENCE: 141
aagagcacat agagattaat gac 23

<210> SEQ ID NO 142
<211> LENGTH: 23
<212> TYPE: DNA
<213> ORGANISM: Homo sapiens

<400> SEQUENCE: 142
aagagcacat atagattaat gac 23

<210> SEQ ID NO 143
<211> LENGTH: 23
<212> TYPE: DNA
<213> ORGANISM: Homo sapiens

<400> SEQUENCE: 143
gtcattaatc tctatgtgct ctt 23

<210> SEQ ID NO 144
<211> LENGTH: 23
<212> TYPE: DNA
<213> ORGANISM: Homo sapiens

<400> SEQUENCE: 144
gtcattaatc tatatgtgct ctt 23

<210> SEQ ID NO 145
<211> LENGTH: 23
<212> TYPE: DNA
<213> ORGANISM: Homo sapiens

<400> SEQUENCE: 145
ttcatcgtcc cctctcccct gtc                                          23

<210> SEQ ID NO 146
<211> LENGTH: 23
<212> TYPE: DNA
<213> ORGANISM: Homo sapiens

<400> SEQUENCE: 146
ttcatcgtcc catctcccct gtc                                          23

<210> SEQ ID NO 147
<211> LENGTH: 23
<212> TYPE: DNA
<213> ORGANISM: Homo sapiens

<400> SEQUENCE: 147
gacaggggag agggacgat gaa                                           23

<210> SEQ ID NO 148
<211> LENGTH: 23
<212> TYPE: DNA
<213> ORGANISM: Homo sapiens

<400> SEQUENCE: 148
gacaggggag atgggacgat gaa                                          23

<210> SEQ ID NO 149
<211> LENGTH: 25
<212> TYPE: DNA
<213> ORGANISM: Homo sapiens

<400> SEQUENCE: 149
gcttctttgg gaaggggaag taggg                                        25

<210> SEQ ID NO 150
<211> LENGTH: 25
<212> TYPE: DNA
<213> ORGANISM: Homo sapiens

<400> SEQUENCE: 150
ccctacttcc ccttcccaaa gaagc                                        25

<210> SEQ ID NO 151
<211> LENGTH: 25
<212> TYPE: DNA
<213> ORGANISM: Homo sapiens

<400> SEQUENCE: 151
gcttctttgg gaggggaag taggg                                         25

<210> SEQ ID NO 152
<211> LENGTH: 25
<212> TYPE: DNA
<213> ORGANISM: Homo sapiens

<400> SEQUENCE: 152
ccctacttcc cctcccaaa gaagc                                         25

<210> SEQ ID NO 153
<211> LENGTH: 23
<212> TYPE: DNA
<213> ORGANISM: Homo sapiens

<400> SEQUENCE: 153
ctagagggtc accgcgtcta tgc                                              23

<210> SEQ ID NO 154
<211> LENGTH: 23
<212> TYPE: DNA
<213> ORGANISM: Homo sapiens

<400> SEQUENCE: 154
ctagagggtc aacgcgtcta tgc                                              23

<210> SEQ ID NO 155
<211> LENGTH: 23
<212> TYPE: DNA
<213> ORGANISM: Homo sapiens

<400> SEQUENCE: 155
gcatagacgc ggtgaccctc tag                                              23

<210> SEQ ID NO 156
<211> LENGTH: 23
<212> TYPE: DNA
<213> ORGANISM: Homo sapiens

<400> SEQUENCE: 156
gcatagacgc gttgaccctc tag                                              23

<210> SEQ ID NO 157
<211> LENGTH: 23
<212> TYPE: DNA
<213> ORGANISM: Homo sapiens

<400> SEQUENCE: 157
gaagggccaa ggaaggggtt aga                                              23

<210> SEQ ID NO 158
<211> LENGTH: 23
<212> TYPE: DNA
<213> ORGANISM: Homo sapiens

<400> SEQUENCE: 158
gaagggccaa gcaaggggtt aga                                              23

<210> SEQ ID NO 159
<211> LENGTH: 21
<212> TYPE: DNA
<213> ORGANISM: Homo sapiens

<400> SEQUENCE: 159
ctaacccctt ccttggccct t                                                21

<210> SEQ ID NO 160
<211> LENGTH: 21
<212> TYPE: DNA
<213> ORGANISM: Homo sapiens

<400> SEQUENCE: 160
ctaacccctt gcttggccct t                                                21

<210> SEQ ID NO 161
<211> LENGTH: 23
<212> TYPE: DNA
<213> ORGANISM: Homo sapiens

<400> SEQUENCE: 161
tagacgcagc ccgcaggcag ccc                                              23

<210> SEQ ID NO 162
<211> LENGTH: 23
<212> TYPE: DNA
<213> ORGANISM: Homo sapiens

<400> SEQUENCE: 162
tagacgcagc ctgcaggcag ccc                                              23

<210> SEQ ID NO 163
<211> LENGTH: 23
<212> TYPE: DNA
<213> ORGANISM: Homo sapiens

<400> SEQUENCE: 163
gggctgcctg cgggctgcgt cta                                              23

<210> SEQ ID NO 164
<211> LENGTH: 23
<212> TYPE: DNA
<213> ORGANISM: Homo sapiens

<400> SEQUENCE: 164
gggctgcctg caggctgcgt cta                                              23

<210> SEQ ID NO 165
<211> LENGTH: 23
<212> TYPE: DNA
<213> ORGANISM: Homo sapiens

<400> SEQUENCE: 165
ccctcactta ccgggtcaca ctt                                              23

<210> SEQ ID NO 166
<211> LENGTH: 23
<212> TYPE: DNA
<213> ORGANISM: Homo sapiens

<400> SEQUENCE: 166
ccctcactta ctgggtcaca ctt                                              23

<210> SEQ ID NO 167
<211> LENGTH: 21
<212> TYPE: DNA
<213> ORGANISM: Homo sapiens

<400> SEQUENCE: 167
cctcacttac cgggtcacac t                                                21

<210> SEQ ID NO 168
<211> LENGTH: 21
<212> TYPE: DNA
<213> ORGANISM: Homo sapiens

<400> SEQUENCE: 168
cctcacttac tgggtcacac t                                                21

<210> SEQ ID NO 169
<211> LENGTH: 23
<212> TYPE: DNA

<213> ORGANISM: Homo sapiens

<400> SEQUENCE: 169
tcttctcctt taacggcaag gac                                              23

<210> SEQ ID NO 170
<211> LENGTH: 23
<212> TYPE: DNA
<213> ORGANISM: Homo sapiens

<400> SEQUENCE: 170
tcttctcctt tgacggcaag gac                                              23

<210> SEQ ID NO 171
<211> LENGTH: 23
<212> TYPE: DNA
<213> ORGANISM: Homo sapiens

<400> SEQUENCE: 171
gtccttgccg ttaaaggaga aga                                              23

<210> SEQ ID NO 172
<211> LENGTH: 23
<212> TYPE: DNA
<213> ORGANISM: Homo sapiens

<400> SEQUENCE: 172
gtccttgccg tcaaaggaga aga                                              23

<210> SEQ ID NO 173
<211> LENGTH: 23
<212> TYPE: DNA
<213> ORGANISM: Homo sapiens

<400> SEQUENCE: 173
gcggctgctg ccgctgctgc tac                                              23

<210> SEQ ID NO 174
<211> LENGTH: 23
<212> TYPE: DNA
<213> ORGANISM: Homo sapiens

<400> SEQUENCE: 174
gcggctgctg ctgctgctgc tac                                              23

<210> SEQ ID NO 175
<211> LENGTH: 23
<212> TYPE: DNA
<213> ORGANISM: Homo sapiens

<400> SEQUENCE: 175
gtagcagcag cggcagcagc cgc                                              23

<210> SEQ ID NO 176
<211> LENGTH: 23
<212> TYPE: DNA
<213> ORGANISM: Homo sapiens

<400> SEQUENCE: 176
gtagcagcag cagcagcagc cgc                                              23

<210> SEQ ID NO 177
<211> LENGTH: 23

<212> TYPE: DNA
<213> ORGANISM: Homo sapiens

<400> SEQUENCE: 177
cccttccatc cctcaggtgt cct                                          23

<210> SEQ ID NO 178
<211> LENGTH: 23
<212> TYPE: DNA
<213> ORGANISM: Homo sapiens

<400> SEQUENCE: 178
cccttccatc cttcaggtgt cct                                          23

<210> SEQ ID NO 179
<211> LENGTH: 21
<212> TYPE: DNA
<213> ORGANISM: Homo sapiens

<400> SEQUENCE: 179
ccttccatcc ctcaggtgtc c                                            21

<210> SEQ ID NO 180
<211> LENGTH: 21
<212> TYPE: DNA
<213> ORGANISM: Homo sapiens

<400> SEQUENCE: 180
ccttccatcc ttcaggtgtc c                                            21

<210> SEQ ID NO 181
<211> LENGTH: 23
<212> TYPE: DNA
<213> ORGANISM: Homo sapiens

<400> SEQUENCE: 181
gacagggttg cgctgatcct ccc                                          23

<210> SEQ ID NO 182
<211> LENGTH: 23
<212> TYPE: DNA
<213> ORGANISM: Homo sapiens

<400> SEQUENCE: 182
gacagggttg cactgatcct ccc                                          23

<210> SEQ ID NO 183
<211> LENGTH: 23
<212> TYPE: DNA
<213> ORGANISM: Homo sapiens

<400> SEQUENCE: 183
gggaggatca gcgcaaccct gtc                                          23

<210> SEQ ID NO 184
<211> LENGTH: 23
<212> TYPE: DNA
<213> ORGANISM: Homo sapiens

<400> SEQUENCE: 184
gggaggatca gtgcaaccct gtc                                          23

<210> SEQ ID NO 185

-continued

```
<211> LENGTH: 23
<212> TYPE: DNA
<213> ORGANISM: Homo sapiens

<400> SEQUENCE: 185
ggctcccgct gccatcctgg ctc                                          23

<210> SEQ ID NO 186
<211> LENGTH: 23
<212> TYPE: DNA
<213> ORGANISM: Homo sapiens

<400> SEQUENCE: 186
ggctcccgct gacatcctgg ctc                                          23

<210> SEQ ID NO 187
<211> LENGTH: 21
<212> TYPE: DNA
<213> ORGANISM: Homo sapiens

<400> SEQUENCE: 187
gctcccgctg ccatcctggc t                                            21

<210> SEQ ID NO 188
<211> LENGTH: 21
<212> TYPE: DNA
<213> ORGANISM: Homo sapiens

<400> SEQUENCE: 188
gctcccgctg acatcctggc t                                            21

<210> SEQ ID NO 189
<211> LENGTH: 23
<212> TYPE: DNA
<213> ORGANISM: Homo sapiens

<400> SEQUENCE: 189
caggaagcct gcagtcctgg aag                                          23

<210> SEQ ID NO 190
<211> LENGTH: 23
<212> TYPE: DNA
<213> ORGANISM: Homo sapiens

<400> SEQUENCE: 190
caggaagcct gtagtcctgg aag                                          23

<210> SEQ ID NO 191
<211> LENGTH: 23
<212> TYPE: DNA
<213> ORGANISM: Homo sapiens

<400> SEQUENCE: 191
cttccaggac tgcaggcttc ctg                                          23

<210> SEQ ID NO 192
<211> LENGTH: 23
<212> TYPE: DNA
<213> ORGANISM: Homo sapiens

<400> SEQUENCE: 192
cttccaggac tacaggcttc ctg                                          23
```

<210> SEQ ID NO 193
<211> LENGTH: 23
<212> TYPE: DNA
<213> ORGANISM: Homo sapiens

<400> SEQUENCE: 193
ctccgggcgt gagcacgagg agc                                          23

<210> SEQ ID NO 194
<211> LENGTH: 23
<212> TYPE: DNA
<213> ORGANISM: Homo sapiens

<400> SEQUENCE: 194
ctccgggcgt gcgcacgagg agc                                          23

<210> SEQ ID NO 195
<211> LENGTH: 23
<212> TYPE: DNA
<213> ORGANISM: Homo sapiens

<400> SEQUENCE: 195
gctcctcgtg ctcacgcccg gag                                          23

<210> SEQ ID NO 196
<211> LENGTH: 23
<212> TYPE: DNA
<213> ORGANISM: Homo sapiens

<400> SEQUENCE: 196
gctcctcgtg cgcacgcccg gag                                          23

<210> SEQ ID NO 197
<211> LENGTH: 21
<212> TYPE: DNA
<213> ORGANISM: Homo sapiens

<400> SEQUENCE: 197
aacagcaagt actagctctc c                                            21

<210> SEQ ID NO 198
<211> LENGTH: 21
<212> TYPE: DNA
<213> ORGANISM: Homo sapiens

<400> SEQUENCE: 198
aacagcaagt gctagctctc c                                            21

<210> SEQ ID NO 199
<211> LENGTH: 21
<212> TYPE: DNA
<213> ORGANISM: Homo sapiens

<400> SEQUENCE: 199
ggagagctag tacttgctgt t                                            21

<210> SEQ ID NO 200
<211> LENGTH: 21
<212> TYPE: DNA
<213> ORGANISM: Homo sapiens

<400> SEQUENCE: 200
ggagagctag cacttgctgt t                                            21

```
<210> SEQ ID NO 201
<211> LENGTH: 23
<212> TYPE: DNA
<213> ORGANISM: Homo sapiens

<400> SEQUENCE: 201
cctccaccat gatactagga ccc                                              23

<210> SEQ ID NO 202
<211> LENGTH: 23
<212> TYPE: DNA
<213> ORGANISM: Homo sapiens

<400> SEQUENCE: 202
cctccaccat ggtactagga ccc                                              23

<210> SEQ ID NO 203
<211> LENGTH: 21
<212> TYPE: DNA
<213> ORGANISM: Homo sapiens

<400> SEQUENCE: 203
ctccaccatg atactaggac c                                                21

<210> SEQ ID NO 204
<211> LENGTH: 21
<212> TYPE: DNA
<213> ORGANISM: Homo sapiens

<400> SEQUENCE: 204
ctccaccatg gtactaggac c                                                21

<210> SEQ ID NO 205
<211> LENGTH: 23
<212> TYPE: DNA
<213> ORGANISM: Homo sapiens

<400> SEQUENCE: 205
gcgtgagcca ccgcgcctgg ccg                                              23

<210> SEQ ID NO 206
<211> LENGTH: 23
<212> TYPE: DNA
<213> ORGANISM: Homo sapiens

<400> SEQUENCE: 206
gcgtgagcca ctgcgcctgg ccg                                              23

<210> SEQ ID NO 207
<211> LENGTH: 21
<212> TYPE: DNA
<213> ORGANISM: Homo sapiens

<400> SEQUENCE: 207
cgtgagccac cgcgcctggc c                                                21

<210> SEQ ID NO 208
<211> LENGTH: 21
<212> TYPE: DNA
<213> ORGANISM: Homo sapiens

<400> SEQUENCE: 208
cgtgagccac tgcgcctggc c                                                21
```

<210> SEQ ID NO 209
<211> LENGTH: 21
<212> TYPE: DNA
<213> ORGANISM: Homo sapiens

<400> SEQUENCE: 209
gtgctgggat tacaggcgtg a                                              21

<210> SEQ ID NO 210
<211> LENGTH: 21
<212> TYPE: DNA
<213> ORGANISM: Homo sapiens

<400> SEQUENCE: 210
gtgctgggat gacaggcgtg a                                              21

<210> SEQ ID NO 211
<211> LENGTH: 19
<212> TYPE: DNA
<213> ORGANISM: Homo sapiens

<400> SEQUENCE: 211
cacgcctgta atcccagca                                                 19

<210> SEQ ID NO 212
<211> LENGTH: 19
<212> TYPE: DNA
<213> ORGANISM: Homo sapiens

<400> SEQUENCE: 212
cacgcctgtc atcccagca                                                 19

<210> SEQ ID NO 213
<211> LENGTH: 21
<212> TYPE: DNA
<213> ORGANISM: Homo sapiens

<400> SEQUENCE: 213
ccgctccaac gccctcaacc c                                              21

<210> SEQ ID NO 214
<211> LENGTH: 21
<212> TYPE: DNA
<213> ORGANISM: Homo sapiens

<400> SEQUENCE: 214
ccgctccaac accctcaacc c                                              21

<210> SEQ ID NO 215
<211> LENGTH: 19
<212> TYPE: DNA
<213> ORGANISM: Homo sapiens

<400> SEQUENCE: 215
cgctccaacg ccctcaacc                                                 19

<210> SEQ ID NO 216
<211> LENGTH: 19
<212> TYPE: DNA
<213> ORGANISM: Homo sapiens

<400> SEQUENCE: 216
cgctccaaca ccctcaacc                                          19

<210> SEQ ID NO 217
<211> LENGTH: 23
<212> TYPE: DNA
<213> ORGANISM: Homo sapiens

<400> SEQUENCE: 217
ggattttcag ggtaggtaat gaa                                     23

<210> SEQ ID NO 218
<211> LENGTH: 23
<212> TYPE: DNA
<213> ORGANISM: Homo sapiens

<400> SEQUENCE: 218
ggattttcag gataggtaat gaa                                     23

<210> SEQ ID NO 219
<211> LENGTH: 23
<212> TYPE: DNA
<213> ORGANISM: Homo sapiens

<400> SEQUENCE: 219
ttcattacct accctgaaaa tcc                                     23

<210> SEQ ID NO 220
<211> LENGTH: 23
<212> TYPE: DNA
<213> ORGANISM: Homo sapiens

<400> SEQUENCE: 220
ttcattacct atcctgaaaa tcc                                     23

<210> SEQ ID NO 221
<211> LENGTH: 21
<212> TYPE: DNA
<213> ORGANISM: Homo sapiens

<400> SEQUENCE: 221
gtgtgagccc gggaggtgga g                                       21

<210> SEQ ID NO 222
<211> LENGTH: 21
<212> TYPE: DNA
<213> ORGANISM: Homo sapiens

<400> SEQUENCE: 222
gtgtgagccc aggaggtgga g                                       21

<210> SEQ ID NO 223
<211> LENGTH: 19
<212> TYPE: DNA
<213> ORGANISM: Homo sapiens

<400> SEQUENCE: 223
tgtgagcccg ggaggtgga                                          19

<210> SEQ ID NO 224
<211> LENGTH: 19
<212> TYPE: DNA
<213> ORGANISM: Homo sapiens

<400> SEQUENCE: 224
tgtgagccca ggaggtgga                                              19

<210> SEQ ID NO 225
<211> LENGTH: 23
<212> TYPE: DNA
<213> ORGANISM: Homo sapiens

<400> SEQUENCE: 225
aaaagcatac aattgataat tca                                         23

<210> SEQ ID NO 226
<211> LENGTH: 23
<212> TYPE: DNA
<213> ORGANISM: Homo sapiens

<400> SEQUENCE: 226
aaaagcatac atttgataat tca                                         23

<210> SEQ ID NO 227
<211> LENGTH: 23
<212> TYPE: DNA
<213> ORGANISM: Homo sapiens

<400> SEQUENCE: 227
tgaattatca attgtatgct ttt                                         23

<210> SEQ ID NO 228
<211> LENGTH: 23
<212> TYPE: DNA
<213> ORGANISM: Homo sapiens

<400> SEQUENCE: 228
tgaattatca aatgtatgct ttt                                         23

<210> SEQ ID NO 229
<211> LENGTH: 23
<212> TYPE: DNA
<213> ORGANISM: Homo sapiens

<400> SEQUENCE: 229
cacaatatcc tctggggttt ggc                                         23

<210> SEQ ID NO 230
<211> LENGTH: 23
<212> TYPE: DNA
<213> ORGANISM: Homo sapiens

<400> SEQUENCE: 230
cacaatatcc tttggggttt ggc                                         23

<210> SEQ ID NO 231
<211> LENGTH: 23
<212> TYPE: DNA
<213> ORGANISM: Homo sapiens

<400> SEQUENCE: 231
gccaaacccc agaggatatt gtg                                         23

<210> SEQ ID NO 232
<211> LENGTH: 23
<212> TYPE: DNA
<213> ORGANISM: Homo sapiens

<400> SEQUENCE: 232
gccaaacccc aaaggatatt gtg                                               23

<210> SEQ ID NO 233
<211> LENGTH: 23
<212> TYPE: DNA
<213> ORGANISM: Homo sapiens

<400> SEQUENCE: 233
tccaggcttc cgcaacttac acg                                               23

<210> SEQ ID NO 234
<211> LENGTH: 23
<212> TYPE: DNA
<213> ORGANISM: Homo sapiens

<400> SEQUENCE: 234
tccaggcttc ctcaacttac acg                                               23

<210> SEQ ID NO 235
<211> LENGTH: 23
<212> TYPE: DNA
<213> ORGANISM: Homo sapiens

<400> SEQUENCE: 235
cgtgtaagtt gcggaagcct gga                                               23

<210> SEQ ID NO 236
<211> LENGTH: 23
<212> TYPE: DNA
<213> ORGANISM: Homo sapiens

<400> SEQUENCE: 236
cgtgtaagtt gaggaagcct gga                                               23

<210> SEQ ID NO 237
<211> LENGTH: 21
<212> TYPE: DNA
<213> ORGANISM: Homo sapiens

<400> SEQUENCE: 237
tctactccac tgctgtctat c                                                 21

<210> SEQ ID NO 238
<211> LENGTH: 21
<212> TYPE: DNA
<213> ORGANISM: Homo sapiens

<400> SEQUENCE: 238
tctactccac cgctgtctat c                                                 21

<210> SEQ ID NO 239
<211> LENGTH: 21
<212> TYPE: DNA
<213> ORGANISM: Homo sapiens

<400> SEQUENCE: 239
gatagacagc ggtggagtag a                                                 21

<210> SEQ ID NO 240
<211> LENGTH: 21
<212> TYPE: DNA
<213> ORGANISM: Homo sapiens -continued

<400> SEQUENCE: 240
gatagacagc agtggagtag a                                      21

<210> SEQ ID NO 241
<211> LENGTH: 21
<212> TYPE: DNA
<213> ORGANISM: Homo sapiens

<400> SEQUENCE: 241
cgtgcggcct cgattggagg t                                      21

<210> SEQ ID NO 242
<211> LENGTH: 21
<212> TYPE: DNA
<213> ORGANISM: Homo sapiens

<400> SEQUENCE: 242
cgtgcggcct tgattggagg t                                      21

<210> SEQ ID NO 243
<211> LENGTH: 19
<212> TYPE: DNA
<213> ORGANISM: Homo sapiens

<400> SEQUENCE: 243
gtgcggcctc gattggagg                                         19

<210> SEQ ID NO 244
<211> LENGTH: 19
<212> TYPE: DNA
<213> ORGANISM: Homo sapiens

<400> SEQUENCE: 244
gtgcggcctt gattggagg                                         19

<210> SEQ ID NO 245
<211> LENGTH: 23
<212> TYPE: DNA
<213> ORGANISM: Homo sapiens

<400> SEQUENCE: 245
cgttgtcccc aaattgcagg aac                                    23

<210> SEQ ID NO 246
<211> LENGTH: 23
<212> TYPE: DNA
<213> ORGANISM: Homo sapiens

<400> SEQUENCE: 246
cgttgtcccc agattgcagg aac                                    23

<210> SEQ ID NO 247
<211> LENGTH: 23
<212> TYPE: DNA
<213> ORGANISM: Homo sapiens

<400> SEQUENCE: 247
gttcctgcaa tttggggaca acg                                    23

<210> SEQ ID NO 248
<211> LENGTH: 23
<212> TYPE: DNA

<213> ORGANISM: Homo sapiens

<400> SEQUENCE: 248
gttcctgcaa tctggggaca acg    23

<210> SEQ ID NO 249
<211> LENGTH: 21
<212> TYPE: DNA
<213> ORGANISM: Homo sapiens

<400> SEQUENCE: 249
gccttctcct ctctgtcccc a    21

<210> SEQ ID NO 250
<211> LENGTH: 21
<212> TYPE: DNA
<213> ORGANISM: Homo sapiens

<400> SEQUENCE: 250
gccttctcct ttctgtcccc a    21

<210> SEQ ID NO 251
<211> LENGTH: 19
<212> TYPE: DNA
<213> ORGANISM: Homo sapiens

<400> SEQUENCE: 251
ccttctcctc tctgtcccc    19

<210> SEQ ID NO 252
<211> LENGTH: 19
<212> TYPE: DNA
<213> ORGANISM: Homo sapiens

<400> SEQUENCE: 252
ccttctcctt tctgtcccc    19

<210> SEQ ID NO 253
<211> LENGTH: 23
<212> TYPE: DNA
<213> ORGANISM: Homo sapiens

<400> SEQUENCE: 253
ggcggcagct ccggtccgcg ccc    23

<210> SEQ ID NO 254
<211> LENGTH: 23
<212> TYPE: DNA
<213> ORGANISM: Homo sapiens

<400> SEQUENCE: 254
ggcggcagct cgggtccgcg ccc    23

<210> SEQ ID NO 255
<211> LENGTH: 23
<212> TYPE: DNA
<213> ORGANISM: Homo sapiens

<400> SEQUENCE: 255
gggcgcggac cggagctgcc gcc    23

<210> SEQ ID NO 256
<211> LENGTH: 23

<212> TYPE: DNA
<213> ORGANISM: Homo sapiens

<400> SEQUENCE: 256
gggcgcggac ccgagctgcc gcc                                    23

<210> SEQ ID NO 257
<211> LENGTH: 23
<212> TYPE: DNA
<213> ORGANISM: Homo sapiens

<400> SEQUENCE: 257
ccgaccggcc ggccttcgcc tcc                                    23

<210> SEQ ID NO 258
<211> LENGTH: 23
<212> TYPE: DNA
<213> ORGANISM: Homo sapiens

<400> SEQUENCE: 258
ccgaccggcc gtccttcgcc tcc                                    23

<210> SEQ ID NO 259
<211> LENGTH: 23
<212> TYPE: DNA
<213> ORGANISM: Homo sapiens

<400> SEQUENCE: 259
ggaggcgaag gccggccggt cgg                                    23

<210> SEQ ID NO 260
<211> LENGTH: 23
<212> TYPE: DNA
<213> ORGANISM: Homo sapiens

<400> SEQUENCE: 260
ggaggcgaag gacggccggt cgg                                    23

<210> SEQ ID NO 261
<211> LENGTH: 21
<212> TYPE: DNA
<213> ORGANISM: Homo sapiens

<400> SEQUENCE: 261
cgcctctctc ttgcccttgt c                                      21

<210> SEQ ID NO 262
<211> LENGTH: 21
<212> TYPE: DNA
<213> ORGANISM: Homo sapiens

<400> SEQUENCE: 262
cgcctctctc ctgcccttgt c                                      21

<210> SEQ ID NO 263
<211> LENGTH: 19
<212> TYPE: DNA
<213> ORGANISM: Homo sapiens

<400> SEQUENCE: 263
gcctctctct tgcccttgt                                         19

<210> SEQ ID NO 264

-continued

```
<211> LENGTH: 19
<212> TYPE: DNA
<213> ORGANISM: Homo sapiens

<400> SEQUENCE: 264
gcctctctcc tgcccttgt                                                    19

<210> SEQ ID NO 265
<211> LENGTH: 23
<212> TYPE: DNA
<213> ORGANISM: Homo sapiens

<400> SEQUENCE: 265
cagaaaaaag acgcaggatt tcc                                               23

<210> SEQ ID NO 266
<211> LENGTH: 23
<212> TYPE: DNA
<213> ORGANISM: Homo sapiens

<400> SEQUENCE: 266
cagaaaaaag atgcaggatt tcc                                               23

<210> SEQ ID NO 267
<211> LENGTH: 23
<212> TYPE: DNA
<213> ORGANISM: Homo sapiens

<400> SEQUENCE: 267
ggaaatcctg cgtctttttt ctg                                               23

<210> SEQ ID NO 268
<211> LENGTH: 23
<212> TYPE: DNA
<213> ORGANISM: Homo sapiens

<400> SEQUENCE: 268
ggaaatcctg catctttttt ctg                                               23

<210> SEQ ID NO 269
<211> LENGTH: 23
<212> TYPE: DNA
<213> ORGANISM: Homo sapiens

<400> SEQUENCE: 269
agggaaaaga agaggatact tct                                               23

<210> SEQ ID NO 270
<211> LENGTH: 23
<212> TYPE: DNA
<213> ORGANISM: Homo sapiens

<400> SEQUENCE: 270
agggaaaaga aaggatactt ctc                                               23

<210> SEQ ID NO 271
<211> LENGTH: 23
<212> TYPE: DNA
<213> ORGANISM: Homo sapiens

<400> SEQUENCE: 271
agaagtatcc tcttcttttc cct                                               23
```

```
<210> SEQ ID NO 272
<211> LENGTH: 23
<212> TYPE: DNA
<213> ORGANISM: Homo sapiens

<400> SEQUENCE: 272
gagaagtatc ctttcttttc cct                                              23

<210> SEQ ID NO 273
<211> LENGTH: 23
<212> TYPE: DNA
<213> ORGANISM: Homo sapiens

<400> SEQUENCE: 273
gtttgtgggg cactccctgc cag                                              23

<210> SEQ ID NO 274
<211> LENGTH: 23
<212> TYPE: DNA
<213> ORGANISM: Homo sapiens

<400> SEQUENCE: 274
gtttgtgggg cgctccctgc cag                                              23

<210> SEQ ID NO 275
<211> LENGTH: 21
<212> TYPE: DNA
<213> ORGANISM: Homo sapiens

<400> SEQUENCE: 275
tggcagggag tgccccacaa a                                                21

<210> SEQ ID NO 276
<211> LENGTH: 21
<212> TYPE: DNA
<213> ORGANISM: Homo sapiens

<400> SEQUENCE: 276
tggcagggag cgccccacaa a                                                21

<210> SEQ ID NO 277
<211> LENGTH: 23
<212> TYPE: DNA
<213> ORGANISM: Homo sapiens

<400> SEQUENCE: 277
tcttacaggg atggaggcaa tgg                                              23

<210> SEQ ID NO 278
<211> LENGTH: 23
<212> TYPE: DNA
<213> ORGANISM: Homo sapiens

<400> SEQUENCE: 278
tcttacaggg acggaggcaa tgg                                              23

<210> SEQ ID NO 279
<211> LENGTH: 23
<212> TYPE: DNA
<213> ORGANISM: Homo sapiens

<400> SEQUENCE: 279
ccattgcctc catccctgta aga                                              23
```

<210> SEQ ID NO 280
<211> LENGTH: 23
<212> TYPE: DNA
<213> ORGANISM: Homo sapiens

<400> SEQUENCE: 280
ccattgcctc cgtccctgta aga                                                 23

<210> SEQ ID NO 281
<211> LENGTH: 23
<212> TYPE: DNA
<213> ORGANISM: Homo sapiens

<400> SEQUENCE: 281
gccgcgctga ttgaggccat cca                                                 23

<210> SEQ ID NO 282
<211> LENGTH: 23
<212> TYPE: DNA
<213> ORGANISM: Homo sapiens

<400> SEQUENCE: 282
gccgcgctga tcgaggccat cca                                                 23

<210> SEQ ID NO 283
<211> LENGTH: 21
<212> TYPE: DNA
<213> ORGANISM: Homo sapiens

<400> SEQUENCE: 283
ccgcgctgat tgaggccatc c                                                   21

<210> SEQ ID NO 284
<211> LENGTH: 21
<212> TYPE: DNA
<213> ORGANISM: Homo sapiens

<400> SEQUENCE: 284
ccgcgctgat cgaggccatc c                                                   21

<210> SEQ ID NO 285
<211> LENGTH: 21
<212> TYPE: DNA
<213> ORGANISM: Homo sapiens

<400> SEQUENCE: 285
tctgcgggag ccgatttcat c                                                   21

<210> SEQ ID NO 286
<211> LENGTH: 21
<212> TYPE: DNA
<213> ORGANISM: Homo sapiens

<400> SEQUENCE: 286
tctgcgggag tcgatttcat c                                                   21

<210> SEQ ID NO 287
<211> LENGTH: 21
<212> TYPE: DNA
<213> ORGANISM: Homo sapiens

<400> SEQUENCE: 287
gatgaaatcg gctcccgcag a                                                   21

-continued

<210> SEQ ID NO 288
<211> LENGTH: 21
<212> TYPE: DNA
<213> ORGANISM: Homo sapiens

<400> SEQUENCE: 288
gatgaaatcg actcccgcag a                                        21

<210> SEQ ID NO 289
<211> LENGTH: 23
<212> TYPE: DNA
<213> ORGANISM: Homo sapiens

<400> SEQUENCE: 289
gaccagtgaa gaaagtgtct ttg                                      23

<210> SEQ ID NO 290
<211> LENGTH: 23
<212> TYPE: DNA
<213> ORGANISM: Homo sapiens

<400> SEQUENCE: 290
gaccagtgaa gcaagtgtct ttg                                      23

<210> SEQ ID NO 291
<211> LENGTH: 21
<212> TYPE: DNA
<213> ORGANISM: Homo sapiens

<400> SEQUENCE: 291
aaagacactt tcttcactgg t                                        21

<210> SEQ ID NO 292
<211> LENGTH: 21
<212> TYPE: DNA
<213> ORGANISM: Homo sapiens

<400> SEQUENCE: 292
aaagacactt gcttcactgg t                                        21

<210> SEQ ID NO 293
<211> LENGTH: 23
<212> TYPE: DNA
<213> ORGANISM: Homo sapiens

<400> SEQUENCE: 293
cattttggga acagtggatg tta                                      23

<210> SEQ ID NO 294
<211> LENGTH: 23
<212> TYPE: DNA
<213> ORGANISM: Homo sapiens

<400> SEQUENCE: 294
cattttggga agagtggatg tta                                      23

<210> SEQ ID NO 295
<211> LENGTH: 23
<212> TYPE: DNA
<213> ORGANISM: Homo sapiens

<400> SEQUENCE: 295

```
taacatccac tgttcccaaa atg                                              23

<210> SEQ ID NO 296
<211> LENGTH: 23
<212> TYPE: DNA
<213> ORGANISM: Homo sapiens

<400> SEQUENCE: 296
taacatccac tcttcccaaa atg                                              23

<210> SEQ ID NO 297
<211> LENGTH: 23
<212> TYPE: DNA
<213> ORGANISM: Homo sapiens

<400> SEQUENCE: 297
gattatttcc caggaaccca taa                                              23

<210> SEQ ID NO 298
<211> LENGTH: 23
<212> TYPE: DNA
<213> ORGANISM: Homo sapiens

<400> SEQUENCE: 298
gattatttcc cgggaaccca taa                                              23

<210> SEQ ID NO 299
<211> LENGTH: 21
<212> TYPE: DNA
<213> ORGANISM: Homo sapiens

<400> SEQUENCE: 299
attatttccc aggaacccat a                                                21

<210> SEQ ID NO 300
<211> LENGTH: 21
<212> TYPE: DNA
<213> ORGANISM: Homo sapiens

<400> SEQUENCE: 300
attatttccc gggaacccat a                                                21

<210> SEQ ID NO 301
<211> LENGTH: 23
<212> TYPE: DNA
<213> ORGANISM: Homo sapiens

<400> SEQUENCE: 301 agcacccccct gaatccaggt aag                                             23

<210> SEQ ID NO 302
<211> LENGTH: 23
<212> TYPE: DNA
<213> ORGANISM: Homo sapiens

<400> SEQUENCE: 302 agcacccccct ggatccaggt aag                                             23

<210> SEQ ID NO 303
<211> LENGTH: 23
<212> TYPE: DNA
<213> ORGANISM: Homo sapiens

<400> SEQUENCE: 303
```

-continued

```
cttacctgga ttcagggggt gct                                              23

<210> SEQ ID NO 304
<211> LENGTH: 23
<212> TYPE: DNA
<213> ORGANISM: Homo sapiens

<400> SEQUENCE: 304
cttacctgga tccagggggt gct                                              23

<210> SEQ ID NO 305
<211> LENGTH: 21
<212> TYPE: DNA
<213> ORGANISM: Homo sapiens

<400> SEQUENCE: 305
gaaggcttca atggatcctt t                                                21

<210> SEQ ID NO 306
<211> LENGTH: 21
<212> TYPE: DNA
<213> ORGANISM: Homo sapiens

<400> SEQUENCE: 306
gaaggcttca gtggatcctt t                                                21

<210> SEQ ID NO 307
<211> LENGTH: 21
<212> TYPE: DNA
<213> ORGANISM: Homo sapiens

<400> SEQUENCE: 307
aaaggatcca ttgaagcctt c                                                21

<210> SEQ ID NO 308
<211> LENGTH: 21
<212> TYPE: DNA
<213> ORGANISM: Homo sapiens

<400> SEQUENCE: 308
aaaggatcca ctgaagcctt c                                                21

<210> SEQ ID NO 309
<211> LENGTH: 23
<212> TYPE: DNA
<213> ORGANISM: Homo sapiens

<400> SEQUENCE: 309
gaatctggta cctggaccaa atc                                              23

<210> SEQ ID NO 310
<211> LENGTH: 23
<212> TYPE: DNA
<213> ORGANISM: Homo sapiens

<400> SEQUENCE: 310
gaatctggta cttggaccaa atc                                              23

<210> SEQ ID NO 311
<211> LENGTH: 21
<212> TYPE: DNA
<213> ORGANISM: Homo sapiens
```

<400> SEQUENCE: 311
aatctggtac ctggaccaaa t                                              21

<210> SEQ ID NO 312
<211> LENGTH: 21
<212> TYPE: DNA
<213> ORGANISM: Homo sapiens

<400> SEQUENCE: 312
aatctggtac ttggaccaaa t                                              21

<210> SEQ ID NO 313
<211> LENGTH: 21
<212> TYPE: DNA
<213> ORGANISM: Homo sapiens

<400> SEQUENCE: 313
cctgccgtca gtggtcacct g                                              21

<210> SEQ ID NO 314
<211> LENGTH: 21
<212> TYPE: DNA
<213> ORGANISM: Homo sapiens

<400> SEQUENCE: 314
cctgccgtca atggtcacct g                                              21

<210> SEQ ID NO 315
<211> LENGTH: 19
<212> TYPE: DNA
<213> ORGANISM: Homo sapiens

<400> SEQUENCE: 315
ctgccgtcag tggtcacct                                                 19

<210> SEQ ID NO 316
<211> LENGTH: 19
<212> TYPE: DNA
<213> ORGANISM: Homo sapiens

<400> SEQUENCE: 316
ctgccgtcaa tggtcacct                                                 19

<210> SEQ ID NO 317
<211> LENGTH: 23
<212> TYPE: DNA
<213> ORGANISM: Homo sapiens

<400> SEQUENCE: 317
gggtattttt acatccctcc agt                                            23

<210> SEQ ID NO 318
<211> LENGTH: 23
<212> TYPE: DNA
<213> ORGANISM: Homo sapiens

<400> SEQUENCE: 318
gggtattttt atatccctcc agt                                            23

<210> SEQ ID NO 319
<211> LENGTH: 21
<212> TYPE: DNA
<213> ORGANISM: Homo sapiens

```
<400> SEQUENCE: 319 ggtatttta catccctcca g                                              21

<210> SEQ ID NO 320
<211> LENGTH: 21
<212> TYPE: DNA
<213> ORGANISM: Homo sapiens

<400> SEQUENCE: 320 ggtatttta tatccctcca g                                              21

<210> SEQ ID NO 321
<211> LENGTH: 23
<212> TYPE: DNA
<213> ORGANISM: Homo sapiens

<400> SEQUENCE: 321
gcttgaacct caaacaattg aag                                           23

<210> SEQ ID NO 322
<211> LENGTH: 23
<212> TYPE: DNA
<213> ORGANISM: Homo sapiens

<400> SEQUENCE: 322
gcttgaacct cgaacaattg aag                                           23

<210> SEQ ID NO 323
<211> LENGTH: 23
<212> TYPE: DNA
<213> ORGANISM: Homo sapiens

<400> SEQUENCE: 323
cttcaattgt ttgaggttca agc                                           23

<210> SEQ ID NO 324
<211> LENGTH: 23
<212> TYPE: DNA
<213> ORGANISM: Homo sapiens

<400> SEQUENCE: 324
cttcaattgt tcgaggttca agc                                           23

<210> SEQ ID NO 325
<211> LENGTH: 23
<212> TYPE: DNA
<213> ORGANISM: Homo sapiens

<400> SEQUENCE: 325
acctggtgat gaatccctta cta                                           23

<210> SEQ ID NO 326
<211> LENGTH: 23
<212> TYPE: DNA
<213> ORGANISM: Homo sapiens

<400> SEQUENCE: 326
acctggtgat ggatcccttta cta                                          23

<210> SEQ ID NO 327
<211> LENGTH: 23
<212> TYPE: DNA
```

<213> ORGANISM: Homo sapiens

<400> SEQUENCE: 327
tagtaaggga ttcatcacca ggt					23

<210> SEQ ID NO 328
<211> LENGTH: 23
<212> TYPE: DNA
<213> ORGANISM: Homo sapiens

<400> SEQUENCE: 328
tagtaaggga tccatcacca ggt					23

<210> SEQ ID NO 329
<211> LENGTH: 23
<212> TYPE: DNA
<213> ORGANISM: Homo sapiens

<400> SEQUENCE: 329
agcacagcaa gtggaaaatc tgt					23

<210> SEQ ID NO 330
<211> LENGTH: 23
<212> TYPE: DNA
<213> ORGANISM: Homo sapiens

<400> SEQUENCE: 330
agcacagcaa gggaaaatct gtc					23

<210> SEQ ID NO 331
<211> LENGTH: 23
<212> TYPE: DNA
<213> ORGANISM: Homo sapiens

<400> SEQUENCE: 331
acagattttc cacttgctgt gct					23

<210> SEQ ID NO 332
<211> LENGTH: 23
<212> TYPE: DNA
<213> ORGANISM: Homo sapiens

<400> SEQUENCE: 332
gacagatttt cccttgctgt gct					23

<210> SEQ ID NO 333
<211> LENGTH: 23
<212> TYPE: DNA
<213> ORGANISM: Homo sapiens

<400> SEQUENCE: 333
attttagatt actgattttg ggc					23

<210> SEQ ID NO 334
<211> LENGTH: 23
<212> TYPE: DNA
<213> ORGANISM: Homo sapiens

<400> SEQUENCE: 334
attttagatt atgattttgg gca					23

<210> SEQ ID NO 335
<211> LENGTH: 23

<212> TYPE: DNA
<213> ORGANISM: Homo sapiens

<400> SEQUENCE: 335
gcccaaaatc agtaatctaa aat                                              23

<210> SEQ ID NO 336
<211> LENGTH: 23
<212> TYPE: DNA
<213> ORGANISM: Homo sapiens

<400> SEQUENCE: 336
tgcccaaaat cataatctaa aat                                              23

<210> SEQ ID NO 337
<211> LENGTH: 23
<212> TYPE: DNA
<213> ORGANISM: Homo sapiens

<400> SEQUENCE: 337
gctttctaat ggtgacaact gat                                              23

<210> SEQ ID NO 338
<211> LENGTH: 23
<212> TYPE: DNA
<213> ORGANISM: Homo sapiens

<400> SEQUENCE: 338
gctttctaat gatgacaact gat                                              23

<210> SEQ ID NO 339
<211> LENGTH: 21
<212> TYPE: DNA
<213> ORGANISM: Homo sapiens

<400> SEQUENCE: 339
ctttctaatg gtgacaactg a                                                21

<210> SEQ ID NO 340
<211> LENGTH: 21
<212> TYPE: DNA
<213> ORGANISM: Homo sapiens

<400> SEQUENCE: 340
ctttctaatg atgacaactg a                                                21

<210> SEQ ID NO 341
<211> LENGTH: 21
<212> TYPE: DNA
<213> ORGANISM: Homo sapiens

<400> SEQUENCE: 341
tagacgacag cgcaggcaag a                                                21

<210> SEQ ID NO 342
<211> LENGTH: 21
<212> TYPE: DNA
<213> ORGANISM: Homo sapiens

<400> SEQUENCE: 342
tagacgacag agcaggcaag a                                                21

<210> SEQ ID NO 343

-continued

```
<211> LENGTH: 21
<212> TYPE: DNA
<213> ORGANISM: Homo sapiens

<400> SEQUENCE: 343
tcttgcctgc gctgtcgtct a                                                    21

<210> SEQ ID NO 344
<211> LENGTH: 21
<212> TYPE: DNA
<213> ORGANISM: Homo sapiens

<400> SEQUENCE: 344
tcttgcctgc tctgtcgtct a                                                    21

<210> SEQ ID NO 345
<211> LENGTH: 23
<212> TYPE: DNA
<213> ORGANISM: Homo sapiens

<400> SEQUENCE: 345
ttggatggct ccaaatcacc ccc                                                  23

<210> SEQ ID NO 346
<211> LENGTH: 23
<212> TYPE: DNA
<213> ORGANISM: Homo sapiens

<400> SEQUENCE: 346
ttggatggct cgaaatcacc ccc                                                  23

<210> SEQ ID NO 347
<211> LENGTH: 23
<212> TYPE: DNA
<213> ORGANISM: Homo sapiens

<400> SEQUENCE: 347
gggggtgatt tggagccatc caa                                                  23

<210> SEQ ID NO 348
<211> LENGTH: 23
<212> TYPE: DNA
<213> ORGANISM: Homo sapiens

<400> SEQUENCE: 348
gggggtgatt tcgagccatc caa                                                  23

<210> SEQ ID NO 349
<211> LENGTH: 23
<212> TYPE: DNA
<213> ORGANISM: Homo sapiens

<400> SEQUENCE: 349
tggtgagcgt ggactttccg gaa                                                  23

<210> SEQ ID NO 350
<211> LENGTH: 23
<212> TYPE: DNA
<213> ORGANISM: Homo sapiens

<400> SEQUENCE: 350
tggtgagcgt gaactttccg gaa                                                  23
```

```
<210> SEQ ID NO 351
<211> LENGTH: 23
<212> TYPE: DNA
<213> ORGANISM: Homo sapiens

<400> SEQUENCE: 351
ttccggaaag tccacgctca cca                                          23

<210> SEQ ID NO 352
<211> LENGTH: 23
<212> TYPE: DNA
<213> ORGANISM: Homo sapiens

<400> SEQUENCE: 352
ttccggaaag ttcacgctca cca                                          23

<210> SEQ ID NO 353
<211> LENGTH: 23
<212> TYPE: DNA
<213> ORGANISM: Homo sapiens

<400> SEQUENCE: 353
gcccggagct gccctttcct ctt                                          23

<210> SEQ ID NO 354
<211> LENGTH: 23
<212> TYPE: DNA
<213> ORGANISM: Homo sapiens

<400> SEQUENCE: 354
gcccggagct gacctttcct ctt                                          23

<210> SEQ ID NO 355
<211> LENGTH: 23
<212> TYPE: DNA
<213> ORGANISM: Homo sapiens

<400> SEQUENCE: 355
aagaggaaag ggcagctccg ggc                                          23

<210> SEQ ID NO 356
<211> LENGTH: 23
<212> TYPE: DNA
<213> ORGANISM: Homo sapiens

<400> SEQUENCE: 356
aagaggaaag gtcagctccg ggc                                          23

<210> SEQ ID NO 357
<211> LENGTH: 23
<212> TYPE: DNA
<213> ORGANISM: Homo sapiens

<400> SEQUENCE: 357
ttgtgtcttg cgatgctaaa gga                                          23

<210> SEQ ID NO 358
<211> LENGTH: 23
<212> TYPE: DNA
<213> ORGANISM: Homo sapiens

<400> SEQUENCE: 358
ttgtgtcttg ccatgctaaa gga                                          23
```

<210> SEQ ID NO 359
<211> LENGTH: 23
<212> TYPE: DNA
<213> ORGANISM: Homo sapiens

<400> SEQUENCE: 359
tcctttagca tcgcaagaca caa                                          23

<210> SEQ ID NO 360
<211> LENGTH: 23
<212> TYPE: DNA
<213> ORGANISM: Homo sapiens

<400> SEQUENCE: 360
tcctttagca tggcaagaca caa                                          23

<210> SEQ ID NO 361
<211> LENGTH: 43
<212> TYPE: DNA
<213> ORGANISM: Homo sapiens

<400> SEQUENCE: 361
taatacgact cactataggg agagttgctt ttcctctggg aag                    43

<210> SEQ ID NO 362
<211> LENGTH: 43
<212> TYPE: DNA
<213> ORGANISM: Homo sapiens

<400> SEQUENCE: 362
taatacgact cactataggg agaccatttg atcagcggag act                    43

<210> SEQ ID NO 363
<211> LENGTH: 45
<212> TYPE: DNA
<213> ORGANISM: Homo sapiens

<400> SEQUENCE: 363
taatacgact cactataggg agaacccatg tatctaggag agctg                  45

<210> SEQ ID NO 364
<211> LENGTH: 43
<212> TYPE: DNA
<213> ORGANISM: Homo sapiens

<400> SEQUENCE: 364
taatacgact cactataggg agagaggggt catgaggtga ctg                    43

<210> SEQ ID NO 365
<211> LENGTH: 44
<212> TYPE: DNA
<213> ORGANISM: Homo sapiens

<400> SEQUENCE: 365
taatacgact cactataggg agatgttatt ccttcctccc caac                   44

<210> SEQ ID NO 366
<211> LENGTH: 43
<212> TYPE: DNA
<213> ORGANISM: Homo sapiens

<400> SEQUENCE: 366
taatacgact cactataggg agacagcgag atctggcgta taa                    43

<210> SEQ ID NO 367
<211> LENGTH: 45
<212> TYPE: DNA
<213> ORGANISM: Homo sapiens

<400> SEQUENCE: 367
taatacgact cactataggg agatgctgtt accaaatctc agtgg            45

<210> SEQ ID NO 368
<211> LENGTH: 43
<212> TYPE: DNA
<213> ORGANISM: Homo sapiens

<400> SEQUENCE: 368
taatacgact cactataggg agagattccg tcccctttct ttc              43

<210> SEQ ID NO 369
<211> LENGTH: 43
<212> TYPE: DNA
<213> ORGANISM: Homo sapiens

<400> SEQUENCE: 369
taatacgact cactataggg agaggggtc cacttgtctg taa               43

<210> SEQ ID NO 370
<211> LENGTH: 43
<212> TYPE: DNA
<213> ORGANISM: Homo sapiens

<400> SEQUENCE: 370
taatacgact cactataggg agagagccaa ggcaggtttt aga              43

<210> SEQ ID NO 371
<211> LENGTH: 43
<212> TYPE: DNA
<213> ORGANISM: Homo sapiens

<400> SEQUENCE: 371
taatacgact cactataggg agaggcagca taagcaggac ttc              43

<210> SEQ ID NO 372
<211> LENGTH: 43
<212> TYPE: DNA
<213> ORGANISM: Homo sapiens

<400> SEQUENCE: 372
taatacgact cactataggg agaatggttt gcaggaaaca agg              43

<210> SEQ ID NO 373
<211> LENGTH: 43
<212> TYPE: DNA
<213> ORGANISM: Homo sapiens

<400> SEQUENCE: 373
taatacgact cactataggg agaacctctg tcttgggcta cca              43

<210> SEQ ID NO 374
<211> LENGTH: 43
<212> TYPE: DNA
<213> ORGANISM: Homo sapiens

<400> SEQUENCE: 374

```
taatacgact cactataggg agagactctt ccacctccca aca       43

<210> SEQ ID NO 375
<211> LENGTH: 41
<212> TYPE: DNA
<213> ORGANISM: Homo sapiens

<400> SEQUENCE: 375
taatacgact cactataggg agaagcacac ggagagcctg a         41

<210> SEQ ID NO 376
<211> LENGTH: 43
<212> TYPE: DNA
<213> ORGANISM: Homo sapiens

<400> SEQUENCE: 376
taatacgact cactataggg agagaaggca ggagacagtg gat       43

<210> SEQ ID NO 377
<211> LENGTH: 43
<212> TYPE: DNA
<213> ORGANISM: Homo sapiens

<400> SEQUENCE: 377
taatacgact cactataggg agaacctggt ccccaaaaga aat       43

<210> SEQ ID NO 378
<211> LENGTH: 43
<212> TYPE: DNA
<213> ORGANISM: Homo sapiens

<400> SEQUENCE: 378
taatacgact cactataggg agagctgtgc tcttttttcca ggt      43

<210> SEQ ID NO 379
<211> LENGTH: 43
<212> TYPE: DNA
<213> ORGANISM: Homo sapiens

<400> SEQUENCE: 379
taatacgact cactataggg agatgcttga ggtgagtttt tgc       43

<210> SEQ ID NO 380
<211> LENGTH: 43
<212> TYPE: DNA
<213> ORGANISM: Homo sapiens

<400> SEQUENCE: 380
taatacgact cactataggg agagaatgac aacaagcccg aat       43

<210> SEQ ID NO 381
<211> LENGTH: 42
<212> TYPE: DNA
<213> ORGANISM: Homo sapiens

<400> SEQUENCE: 381
taatacgact cactataggg agacggacat catcctgtac gc        42

<210> SEQ ID NO 382
<211> LENGTH: 43
<212> TYPE: DNA
<213> ORGANISM: Homo sapiens

<400> SEQUENCE: 382
```

```
taatacgact cactataggg agaaaagagc ttcaacccca aca                43
```

<210> SEQ ID NO 383
<211> LENGTH: 44
<212> TYPE: DNA
<213> ORGANISM: Homo sapiens

<400> SEQUENCE: 383

```
taatacgact cactataggg agacttccac agggtgatct tctg               44
```

<210> SEQ ID NO 384
<211> LENGTH: 43
<212> TYPE: DNA
<213> ORGANISM: Homo sapiens

<400> SEQUENCE: 384

```
taatacgact cactataggg agagaagacc caggtccaga tga                43
```

<210> SEQ ID NO 385
<211> LENGTH: 43
<212> TYPE: DNA
<213> ORGANISM: Homo sapiens

<400> SEQUENCE: 385

```
taatacgact cactataggg agagctgctt ccactatggc ttc                43
```

<210> SEQ ID NO 386
<211> LENGTH: 42
<212> TYPE: DNA
<213> ORGANISM: Homo sapiens

<400> SEQUENCE: 386

```
taatacgact cactataggg agaaacagag gaggggaaag ca                 42
```

<210> SEQ ID NO 387
<211> LENGTH: 43
<212> TYPE: DNA
<213> ORGANISM: Homo sapiens

<400> SEQUENCE: 387

```
taatacgact cactataggg agaccgacac gtctctgcta ctg                43
```

<210> SEQ ID NO 388
<211> LENGTH: 43
<212> TYPE: DNA
<213> ORGANISM: Homo sapiens

<400> SEQUENCE: 388

```
taatacgact cactataggg agaaaggaga tcgaggtccc act                43
```

<210> SEQ ID NO 389
<211> LENGTH: 42
<212> TYPE: DNA
<213> ORGANISM: Homo sapiens

<400> SEQUENCE: 389

```
taatacgact cactataggg agaaagaaca gcctggcctt gt                 42
```

<210> SEQ ID NO 390
<211> LENGTH: 43
<212> TYPE: DNA
<213> ORGANISM: Homo sapiens

```
<400> SEQUENCE: 390
taatacgact cactataggg agaggtcaac ccatctgagt tcc        43

<210> SEQ ID NO 391
<211> LENGTH: 43
<212> TYPE: DNA
<213> ORGANISM: Homo sapiens

<400> SEQUENCE: 391
taatacgact cactataggg agataatcct ccctctcgtg cag        43

<210> SEQ ID NO 392
<211> LENGTH: 43
<212> TYPE: DNA
<213> ORGANISM: Homo sapiens

<400> SEQUENCE: 392
taatacgact cactataggg agatgctccg ctgaccttaa aga        43

<210> SEQ ID NO 393
<211> LENGTH: 43
<212> TYPE: DNA
<213> ORGANISM: Homo sapiens

<400> SEQUENCE: 393
taatacgact cactataggg agaggccact tgtttgtgtg tgt        43

<210> SEQ ID NO 394
<211> LENGTH: 43
<212> TYPE: DNA
<213> ORGANISM: Homo sapiens

<400> SEQUENCE: 394
taatacgact cactataggg agacaccact ccttccaggg tta        43

<210> SEQ ID NO 395
<211> LENGTH: 43
<212> TYPE: DNA
<213> ORGANISM: Homo sapiens

<400> SEQUENCE: 395
taatacgact cactataggg agagagggga gaaagaggga aga        43

<210> SEQ ID NO 396
<211> LENGTH: 43
<212> TYPE: DNA
<213> ORGANISM: Homo sapiens

<400> SEQUENCE: 396
taatacgact cactataggg agagcatttg ctgttcggag ttt        43

<210> SEQ ID NO 397
<211> LENGTH: 45
<212> TYPE: DNA
<213> ORGANISM: Homo sapiens

<400> SEQUENCE: 397
taatacgact cactataggg agacacacac acacacaaat ccaag      45

<210> SEQ ID NO 398
<211> LENGTH: 43
<212> TYPE: DNA
<213> ORGANISM: Homo sapiens
```

```
<400> SEQUENCE: 398
taatacgact cactataggg agacccttc tgatcccagg tct          43

<210> SEQ ID NO 399
<211> LENGTH: 43
<212> TYPE: DNA
<213> ORGANISM: Homo sapiens

<400> SEQUENCE: 399
taatacgact cactataggg agagctggtt cttgggaaat cct         43

<210> SEQ ID NO 400
<211> LENGTH: 43
<212> TYPE: DNA
<213> ORGANISM: Homo sapiens

<400> SEQUENCE: 400
taatacgact cactataggg agacagcatc tgctccctct acc         43

<210> SEQ ID NO 401
<211> LENGTH: 42
<212> TYPE: DNA
<213> ORGANISM: Homo sapiens

<400> SEQUENCE: 401
taatacgact cactataggg agactgagga gccccaacaa ct          42

<210> SEQ ID NO 402
<211> LENGTH: 43
<212> TYPE: DNA
<213> ORGANISM: Homo sapiens

<400> SEQUENCE: 402
taatacgact cactataggg agacacggtt tctcttccag gac         43

<210> SEQ ID NO 403
<211> LENGTH: 42
<212> TYPE: DNA
<213> ORGANISM: Homo sapiens

<400> SEQUENCE: 403
taatacgact cactataggg agacgaggcc ctcctacctt tt          42

<210> SEQ ID NO 404
<211> LENGTH: 43
<212> TYPE: DNA
<213> ORGANISM: Homo sapiens

<400> SEQUENCE: 404
taatacgact cactataggg agacagggtg ttgagtgaca gga         43

<210> SEQ ID NO 405
<211> LENGTH: 48
<212> TYPE: DNA
<213> ORGANISM: Homo sapiens

<400> SEQUENCE: 405
taatacgact cactataggg agattttgt tgacagaatt caaaactt    48

<210> SEQ ID NO 406
<211> LENGTH: 43
<212> TYPE: DNA
```

```
<213> ORGANISM: Homo sapiens

<400> SEQUENCE: 406
taatacgact cactataggg agacagcttg cccgagttct act                43

<210> SEQ ID NO 407
<211> LENGTH: 43
<212> TYPE: DNA
<213> ORGANISM: Homo sapiens

<400> SEQUENCE: 407
taatacgact cactataggg agaccaagag gaagccctaa tcc                43

<210> SEQ ID NO 408
<211> LENGTH: 45
<212> TYPE: DNA
<213> ORGANISM: Homo sapiens

<400> SEQUENCE: 408
taatacgact cactataggg agacaccttg gttcttgtag acgac              45

<210> SEQ ID NO 409
<211> LENGTH: 43
<212> TYPE: DNA
<213> ORGANISM: Homo sapiens

<400> SEQUENCE: 409
taatacgact cactataggg agactgcctt tgtccectag atg                43

<210> SEQ ID NO 410
<211> LENGTH: 43
<212> TYPE: DNA
<213> ORGANISM: Homo sapiens

<400> SEQUENCE: 410
taatacgact cactataggg agagagacca tgaccactca cca                43

<210> SEQ ID NO 411
<211> LENGTH: 43
<212> TYPE: DNA
<213> ORGANISM: Homo sapiens

<400> SEQUENCE: 411
taatacgact cactataggg agagccagga tggtctcagt ctc                43

<210> SEQ ID NO 412
<211> LENGTH: 43
<212> TYPE: DNA
<213> ORGANISM: Homo sapiens

<400> SEQUENCE: 412
taatacgact cactataggg agagccagga tggtctcagt ctc                43

<210> SEQ ID NO 413
<211> LENGTH: 43
<212> TYPE: DNA
<213> ORGANISM: Homo sapiens

<400> SEQUENCE: 413
taatacgact cactataggg agattcgaga gtgaggacgt gtg                43

<210> SEQ ID NO 414
<211> LENGTH: 43
```

```
<212> TYPE: DNA
<213> ORGANISM: Homo sapiens

<400> SEQUENCE: 414
taatacgact cactataggg agactactgg tttgggaggg aca                43

<210> SEQ ID NO 415
<211> LENGTH: 44
<212> TYPE: DNA
<213> ORGANISM: Homo sapiens

<400> SEQUENCE: 415
taatacgact cactataggg agaaagcagt ctgtttgagg gaca               44

<210> SEQ ID NO 416
<211> LENGTH: 46
<212> TYPE: DNA
<213> ORGANISM: Homo sapiens

<400> SEQUENCE: 416
taatacgact cactataggg agatgccatt aaaagaaaat catcca             46

<210> SEQ ID NO 417
<211> LENGTH: 42
<212> TYPE: DNA
<213> ORGANISM: Homo sapiens

<400> SEQUENCE: 417
taatacgact cactataggg agaccectag agctcagcca gt                 42

<210> SEQ ID NO 418
<211> LENGTH: 44
<212> TYPE: DNA
<213> ORGANISM: Homo sapiens

<400> SEQUENCE: 418
taatacgact cactataggg agacagactt agctcaaccc gtca               44

<210> SEQ ID NO 419
<211> LENGTH: 43
<212> TYPE: DNA
<213> ORGANISM: Homo sapiens

<400> SEQUENCE: 419
taatacgact cactataggg agagctccag gagaatcttt cca                43

<210> SEQ ID NO 420
<211> LENGTH: 43
<212> TYPE: DNA
<213> ORGANISM: Homo sapiens

<400> SEQUENCE: 420
taatacgact cactataggg agacaaaccg ctgccactac act                43

<210> SEQ ID NO 421
<211> LENGTH: 43
<212> TYPE: DNA
<213> ORGANISM: Homo sapiens

<400> SEQUENCE: 421
taatacgact cactataggg agagcgacct cttcagatgg att                43

<210> SEQ ID NO 422
```

```
<211> LENGTH: 43
<212> TYPE: DNA
<213> ORGANISM: Homo sapiens

<400> SEQUENCE: 422
taatacgact cactataggg agaagagtca gctccgacct ctc                    43

<210> SEQ ID NO 423
<211> LENGTH: 41
<212> TYPE: DNA
<213> ORGANISM: Homo sapiens

<400> SEQUENCE: 423
taatacgact cactataggg agagacccct tggccgctaaa c                     41

<210> SEQ ID NO 424
<211> LENGTH: 42
<212> TYPE: DNA
<213> ORGANISM: Homo sapiens

<400> SEQUENCE: 424
taatacgact cactataggg agaccatagt ggtgctgaat gg                     42

<210> SEQ ID NO 425
<211> LENGTH: 43
<212> TYPE: DNA
<213> ORGANISM: Homo sapiens

<400> SEQUENCE: 425
taatacgact cactataggg agattggaat gaggacagcc ata                    43

<210> SEQ ID NO 426
<211> LENGTH: 44
<212> TYPE: DNA
<213> ORGANISM: Homo sapiens

<400> SEQUENCE: 426
taatacgact cactataggg agacagcaag gatttgaaag atgc                   44

<210> SEQ ID NO 427
<211> LENGTH: 43
<212> TYPE: DNA
<213> ORGANISM: Homo sapiens

<400> SEQUENCE: 427
taatacgact cactataggg agactccatg tttctgggga aat                    43

<210> SEQ ID NO 428
<211> LENGTH: 43
<212> TYPE: DNA
<213> ORGANISM: Homo sapiens

<400> SEQUENCE: 428
taatacgact cactataggg agagtaatcc gagcctccac tga                    43

<210> SEQ ID NO 429
<211> LENGTH: 41
<212> TYPE: DNA
<213> ORGANISM: Homo sapiens

<400> SEQUENCE: 429
taatacgact cactataggg agactgagct ccctggtggt g                      41
```

```
<210> SEQ ID NO 430
<211> LENGTH: 43
<212> TYPE: DNA
<213> ORGANISM: Homo sapiens

<400> SEQUENCE: 430
taatacgact cactataggg agactgagag ctcctgtgcc ttc          43

<210> SEQ ID NO 431
<211> LENGTH: 42
<212> TYPE: DNA
<213> ORGANISM: Homo sapiens

<400> SEQUENCE: 431
taatacgact cactataggg agactctctg cccagtccct gt           42

<210> SEQ ID NO 432
<211> LENGTH: 42
<212> TYPE: DNA
<213> ORGANISM: Homo sapiens

<400> SEQUENCE: 432
taatacgact cactataggg agaccctctg tcaggagtgt gc           42

<210> SEQ ID NO 433
<211> LENGTH: 45
<212> TYPE: DNA
<213> ORGANISM: Homo sapiens

<400> SEQUENCE: 433
taatacgact cactataggg agaaaggtat tcaaggcagg gagta        45

<210> SEQ ID NO 434
<211> LENGTH: 46
<212> TYPE: DNA
<213> ORGANISM: Homo sapiens

<400> SEQUENCE: 434
taatacgact cactataggg agaaaattaca accagagctt ggcata      46

<210> SEQ ID NO 435
<211> LENGTH: 43
<212> TYPE: DNA
<213> ORGANISM: Homo sapiens

<400> SEQUENCE: 435
taatacgact cactataggg agacctgtga tcccactttc atc          43

<210> SEQ ID NO 436
<211> LENGTH: 43
<212> TYPE: DNA
<213> ORGANISM: Homo sapiens

<400> SEQUENCE: 436
taatacgact cactataggg agagcaagct cacggttgtc tta          43

<210> SEQ ID NO 437
<211> LENGTH: 43
<212> TYPE: DNA
<213> ORGANISM: Homo sapiens

<400> SEQUENCE: 437
taatacgact cactataggg agaggcatgg ttcaccttct cct          43
```

```
<210> SEQ ID NO 438
<211> LENGTH: 43
<212> TYPE: DNA
<213> ORGANISM: Homo sapiens

<400> SEQUENCE: 438
taatacgact cactataggg agatggtgtc tccaggtcaa tca          43

<210> SEQ ID NO 439
<211> LENGTH: 43
<212> TYPE: DNA
<213> ORGANISM: Homo sapiens

<400> SEQUENCE: 439
taatacgact cactataggg agaggctgtt ccctttgaga acc          43

<210> SEQ ID NO 440
<211> LENGTH: 43
<212> TYPE: DNA
<213> ORGANISM: Homo sapiens

<400> SEQUENCE: 440
taatacgact cactataggg agaggaccaa atcaggagag agc          43

<210> SEQ ID NO 441
<211> LENGTH: 43
<212> TYPE: DNA
<213> ORGANISM: Homo sapiens

<400> SEQUENCE: 441
taatacgact cactataggg agaaccccag aaggggttta ctg          43

<210> SEQ ID NO 442
<211> LENGTH: 46
<212> TYPE: DNA
<213> ORGANISM: Homo sapiens

<400> SEQUENCE: 442
taatacgact cactataggg agatcacctt gtgatgttag tttgga       46

<210> SEQ ID NO 443
<211> LENGTH: 43
<212> TYPE: DNA
<213> ORGANISM: Homo sapiens

<400> SEQUENCE: 443
taatacgact cactataggg agattaatgg caggtgtgaa ttg          43

<210> SEQ ID NO 444
<211> LENGTH: 44
<212> TYPE: DNA
<213> ORGANISM: Homo sapiens

<400> SEQUENCE: 444
taatacgact cactataggg agaaaggtgt ggccattgta aaaa         44

<210> SEQ ID NO 445
<211> LENGTH: 43
<212> TYPE: DNA
<213> ORGANISM: Homo sapiens

<400> SEQUENCE: 445
taatacgact cactataggg agagagtcca ggggaacagc ttc          43
```

<210> SEQ ID NO 446
<211> LENGTH: 42
<212> TYPE: DNA
<213> ORGANISM: Homo sapiens

<400> SEQUENCE: 446
taatacgact cactataggg agaggtaccg catgcacaag tc        42

<210> SEQ ID NO 447
<211> LENGTH: 45
<212> TYPE: DNA
<213> ORGANISM: Homo sapiens

<400> SEQUENCE: 447
taatacgact cactataggg agactgcatc agttcacttt tgacc     45

<210> SEQ ID NO 448
<211> LENGTH: 41
<212> TYPE: DNA
<213> ORGANISM: Homo sapiens

<400> SEQUENCE: 448
taatacgact cactataggg agagacagcc aacgcctctt g         41

<210> SEQ ID NO 449
<211> LENGTH: 43
<212> TYPE: DNA
<213> ORGANISM: Homo sapiens

<400> SEQUENCE: 449
taatacgact cactataggg agacaagaca tgccaaagtg ctg       43

<210> SEQ ID NO 450
<211> LENGTH: 41
<212> TYPE: DNA
<213> ORGANISM: Homo sapiens

<400> SEQUENCE: 450
aattaaccct cactaaaggg agagggctgg gaggagaaga t         41

<210> SEQ ID NO 451
<211> LENGTH: 43
<212> TYPE: DNA
<213> ORGANISM: Homo sapiens

<400> SEQUENCE: 451
aattaaccct cactaaaggg agacactcgc acgtttgaca tct       43

<210> SEQ ID NO 452
<211> LENGTH: 43
<212> TYPE: DNA
<213> ORGANISM: Homo sapiens

<400> SEQUENCE: 452
aattaaccct cactaaaggg agaacaaagg ttccattgcc act       43

<210> SEQ ID NO 453
<211> LENGTH: 48
<212> TYPE: DNA
<213> ORGANISM: Homo sapiens

<400> SEQUENCE: 453

```
aattaaccct cactaaaggg agacataata ttcccaacac aattcttg         48
```

<210> SEQ ID NO 454
<211> LENGTH: 43
<212> TYPE: DNA
<213> ORGANISM: Homo sapiens

<400> SEQUENCE: 454

```
aattaaccct cactaaaggg agaacctgac cttggtgttg agc              43
```

<210> SEQ ID NO 455
<211> LENGTH: 43
<212> TYPE: DNA
<213> ORGANISM: Homo sapiens

<400> SEQUENCE: 455

```
aattaaccct cactaaaggg agacccacat gcacatctct gtc              43
```

<210> SEQ ID NO 456
<211> LENGTH: 47
<212> TYPE: DNA
<213> ORGANISM: Homo sapiens

<400> SEQUENCE: 456

```
aattaaccct cactaaaggg agatgctctt tatgttgaac tgtgtga          47
```

<210> SEQ ID NO 457
<211> LENGTH: 43
<212> TYPE: DNA
<213> ORGANISM: Homo sapiens

<400> SEQUENCE: 457

```
aattaaccct cactaaaggg agaaactctg gtccaccagg aca              43
```

<210> SEQ ID NO 458
<211> LENGTH: 43
<212> TYPE: DNA
<213> ORGANISM: Homo sapiens

<400> SEQUENCE: 458

```
aattaaccct cactaaaggg agaccagaac gtgaggtgga ctt              43
```

<210> SEQ ID NO 459
<211> LENGTH: 43
<212> TYPE: DNA
<213> ORGANISM: Homo sapiens

<400> SEQUENCE: 459

```
aattaaccct cactaaaggg agaaagacca cgaccagcag aat              43
```

<210> SEQ ID NO 460
<211> LENGTH: 43
<212> TYPE: DNA
<213> ORGANISM: Homo sapiens

<400> SEQUENCE: 460

```
aattaaccct cactaaaggg agagttgctc gaggacaagt tcc              43
```

<210> SEQ ID NO 461
<211> LENGTH: 43
<212> TYPE: DNA
<213> ORGANISM: Homo sapiens

<400> SEQUENCE: 461
aattaaccct cactaaaggg agaaaagcgg gagatgaagt cct                          43

<210> SEQ ID NO 462
<211> LENGTH: 43
<212> TYPE: DNA
<213> ORGANISM: Homo sapiens

<400> SEQUENCE: 462
aattaaccct cactaaaggg agatcatcac tctgctggtc agg                          43

<210> SEQ ID NO 463
<211> LENGTH: 43
<212> TYPE: DNA
<213> ORGANISM: Homo sapiens

<400> SEQUENCE: 463
aattaaccct cactaaaggg agatggggaa tttctttgtc cag                          43

<210> SEQ ID NO 464
<211> LENGTH: 43
<212> TYPE: DNA
<213> ORGANISM: Homo sapiens

<400> SEQUENCE: 464
aattaaccct cactaaaggg agaaggggaa aaacgctacc tgt                          43

<210> SEQ ID NO 465
<211> LENGTH: 43
<212> TYPE: DNA
<213> ORGANISM: Homo sapiens

<400> SEQUENCE: 465
aattaaccct cactaaaggg agacagtcaa tccctttggt gct                          43

<210> SEQ ID NO 466
<211> LENGTH: 43
<212> TYPE: DNA
<213> ORGANISM: Homo sapiens

<400> SEQUENCE: 466
aattaaccct cactaaaggg agaaaagttg gggacacaca agc                          43

<210> SEQ ID NO 467
<211> LENGTH: 43
<212> TYPE: DNA
<213> ORGANISM: Homo sapiens

<400> SEQUENCE: 467
aattaaccct cactaaaggg agatcgttcc cttggatctg atg                          43

<210> SEQ ID NO 468
<211> LENGTH: 46
<212> TYPE: DNA
<213> ORGANISM: Homo sapiens

<400> SEQUENCE: 468
aattaaccct cactaaaggg agacaggaaa gtctttccc attaca                        46

<210> SEQ ID NO 469
<211> LENGTH: 43
<212> TYPE: DNA
<213> ORGANISM: Homo sapiens

<400> SEQUENCE: 469 aattaacccct cactaaaggg agatgtccgt aggaaggatc agc    43

<210> SEQ ID NO 470
<211> LENGTH: 41
<212> TYPE: DNA
<213> ORGANISM: Homo sapiens

<400> SEQUENCE: 470 aattaacccct cactaaaggg agagatgcgc ccagtacctg t    41

<210> SEQ ID NO 471
<211> LENGTH: 43
<212> TYPE: DNA
<213> ORGANISM: Homo sapiens

<400> SEQUENCE: 471 aattaacccct cactaaaggg agaaccagga ggtacatggc att    43

<210> SEQ ID NO 472
<211> LENGTH: 43
<212> TYPE: DNA
<213> ORGANISM: Homo sapiens

<400> SEQUENCE: 472 aattaacccct cactaaaggg agacatgaag ctgcctccct tag    43

<210> SEQ ID NO 473
<211> LENGTH: 43
<212> TYPE: DNA
<213> ORGANISM: Homo sapiens

<400> SEQUENCE: 473 aattaacccct cactaaaggg agactgccct ggtaggtttt ctg    43

<210> SEQ ID NO 474
<211> LENGTH: 43
<212> TYPE: DNA
<213> ORGANISM: Homo sapiens

<400> SEQUENCE: 474 aattaacccct cactaaaggg agacttcacg tggatgaagt gga    43

<210> SEQ ID NO 475
<211> LENGTH: 43
<212> TYPE: DNA
<213> ORGANISM: Homo sapiens

<400> SEQUENCE: 475 aattaacccct cactaaaggg agagaagagt ccctgacccc tct    43

<210> SEQ ID NO 476
<211> LENGTH: 42
<212> TYPE: DNA
<213> ORGANISM: Homo sapiens

<400> SEQUENCE: 476 aattaacccct cactaaaggg agactccagg ctccagcttt gt    42

<210> SEQ ID NO 477
<211> LENGTH: 43
<212> TYPE: DNA
<213> ORGANISM: Homo sapiens

<400> SEQUENCE: 477
aattaaccct cactaaaggg agaggccttt tggtccagaa ttt        43

<210> SEQ ID NO 478
<211> LENGTH: 43
<212> TYPE: DNA
<213> ORGANISM: Homo sapiens

<400> SEQUENCE: 478
aattaaccct cactaaaggg agaatgtgaa ccagctccct gtc        43

<210> SEQ ID NO 479
<211> LENGTH: 43
<212> TYPE: DNA
<213> ORGANISM: Homo sapiens

<400> SEQUENCE: 479
aattaaccct cactaaaggg agagcaggat agccaggaag aga        43

<210> SEQ ID NO 480
<211> LENGTH: 43
<212> TYPE: DNA
<213> ORGANISM: Homo sapiens

<400> SEQUENCE: 480
aattaaccct cactaaaggg agagtgctgc cccatactca ctt        43

<210> SEQ ID NO 481
<211> LENGTH: 43
<212> TYPE: DNA
<213> ORGANISM: Homo sapiens

<400> SEQUENCE: 481
aattaaccct cactaaaggg agacgttgtc agaaatggtc gaa        43

<210> SEQ ID NO 482
<211> LENGTH: 43
<212> TYPE: DNA
<213> ORGANISM: Homo sapiens

<400> SEQUENCE: 482
aattaaccct cactaaaggg agaggtgggt gtatccacag gac        43

<210> SEQ ID NO 483
<211> LENGTH: 45
<212> TYPE: DNA
<213> ORGANISM: Homo sapiens

<400> SEQUENCE: 483
aattaaccct cactaaaggg agatggagaa agttgaacca cctct      45

<210> SEQ ID NO 484
<211> LENGTH: 43
<212> TYPE: DNA
<213> ORGANISM: Homo sapiens

<400> SEQUENCE: 484
aattaaccct cactaaaggg agagagttca acagcaagca gca        43

<210> SEQ ID NO 485
<211> LENGTH: 43
<212> TYPE: DNA

<213> ORGANISM: Homo sapiens

<400> SEQUENCE: 485
aattaaccct cactaaaggg agacccttct cggcaattta cac          43

<210> SEQ ID NO 486
<211> LENGTH: 43
<212> TYPE: DNA
<213> ORGANISM: Homo sapiens

<400> SEQUENCE: 486
aattaaccct cactaaaggg agaaagcttc tgtggctgga gtc          43

<210> SEQ ID NO 487
<211> LENGTH: 43
<212> TYPE: DNA
<213> ORGANISM: Homo sapiens

<400> SEQUENCE: 487
aattaaccct cactaaaggg agactgattg gctgagggtt cac          43

<210> SEQ ID NO 488
<211> LENGTH: 43
<212> TYPE: DNA
<213> ORGANISM: Homo sapiens

<400> SEQUENCE: 488
aattaaccct cactaaaggg agacccaggc tgaatgacaa aag          43

<210> SEQ ID NO 489
<211> LENGTH: 41
<212> TYPE: DNA
<213> ORGANISM: Homo sapiens

<400> SEQUENCE: 489
aattaaccct cactaaaggg agaaggggct cacaacagtg c            41

<210> SEQ ID NO 490
<211> LENGTH: 41
<212> TYPE: DNA
<213> ORGANISM: Homo sapiens

<400> SEQUENCE: 490
aattaaccct cactaaaggg agacagcccc aaccttgtca c            41

<210> SEQ ID NO 491
<211> LENGTH: 43
<212> TYPE: DNA
<213> ORGANISM: Homo sapiens

<400> SEQUENCE: 491
aattaaccct cactaaaggg agactctcag agctgctcac acg          43

<210> SEQ ID NO 492
<211> LENGTH: 42
<212> TYPE: DNA
<213> ORGANISM: Homo sapiens

<400> SEQUENCE: 492
aattaaccct cactaaaggg agacaggcgt cagcaccagt ag           42

<210> SEQ ID NO 493
<211> LENGTH: 43

```
<212> TYPE: DNA
<213> ORGANISM: Homo sapiens

<400> SEQUENCE: 493
aattaaccct cactaaaggg agacaggctg ggaaacaagg tag          43

<210> SEQ ID NO 494
<211> LENGTH: 43
<212> TYPE: DNA
<213> ORGANISM: Homo sapiens

<400> SEQUENCE: 494
aattaaccct cactaaaggg agactccagc cgatctctct gtt          43

<210> SEQ ID NO 495
<211> LENGTH: 43
<212> TYPE: DNA
<213> ORGANISM: Homo sapiens

<400> SEQUENCE: 495
aattaaccct cactaaaggg agattgcagg tcgcttcctt att          43

<210> SEQ ID NO 496
<211> LENGTH: 43
<212> TYPE: DNA
<213> ORGANISM: Homo sapiens

<400> SEQUENCE: 496
aattaaccct cactaaaggg agaacctctc attcaaccgc cta          43

<210> SEQ ID NO 497
<211> LENGTH: 41
<212> TYPE: DNA
<213> ORGANISM: Homo sapiens

<400> SEQUENCE: 497
aattaaccct cactaaaggg agaggaagcg gctgatcctc a            41

<210> SEQ ID NO 498
<211> LENGTH: 43
<212> TYPE: DNA
<213> ORGANISM: Homo sapiens

<400> SEQUENCE: 498
aattaaccct cactaaaggg agacccagga gccctataaa acc          43

<210> SEQ ID NO 499
<211> LENGTH: 43
<212> TYPE: DNA
<213> ORGANISM: Homo sapiens

<400> SEQUENCE: 499
aattaaccct cactaaaggg agaggccagc tgggaataga gat          43

<210> SEQ ID NO 500
<211> LENGTH: 43
<212> TYPE: DNA
<213> ORGANISM: Homo sapiens

<400> SEQUENCE: 500
aattaaccct cactaaaggg agaacggtgt gatttgtgct gaa          43

<210> SEQ ID NO 501
```

```
<211> LENGTH: 43
<212> TYPE: DNA
<213> ORGANISM: Homo sapiens

<400> SEQUENCE: 501
aattaaccct cactaaaggg agaaacggtg tgatttgtgc tga                        43

<210> SEQ ID NO 502
<211> LENGTH: 43
<212> TYPE: DNA
<213> ORGANISM: Homo sapiens

<400> SEQUENCE: 502
aattaaccct cactaaaggg agagggagca ggaaagtgag gtt                        43

<210> SEQ ID NO 503
<211> LENGTH: 46
<212> TYPE: DNA
<213> ORGANISM: Homo sapiens

<400> SEQUENCE: 503
aattaaccct cactaaaggg agaaagagtt tttaggaccc acttcc                     46

<210> SEQ ID NO 504
<211> LENGTH: 44
<212> TYPE: DNA
<213> ORGANISM: Homo sapiens

<400> SEQUENCE: 504
aattaaccct cactaaaggg agagagctca ggagtttgag acca                       44

<210> SEQ ID NO 505
<211> LENGTH: 43
<212> TYPE: DNA
<213> ORGANISM: Homo sapiens

<400> SEQUENCE: 505
aattaaccct cactaaaggg agaagggcaa acctgagtca tca                        43

<210> SEQ ID NO 506
<211> LENGTH: 43
<212> TYPE: DNA
<213> ORGANISM: Homo sapiens

<400> SEQUENCE: 506
aattaaccct cactaaaggg agagaatctg ccagggctat ttg                        43

<210> SEQ ID NO 507
<211> LENGTH: 43
<212> TYPE: DNA
<213> ORGANISM: Homo sapiens

<400> SEQUENCE: 507
aattaaccct cactaaaggg agagtctggc caagctgctg tat                        43

<210> SEQ ID NO 508
<211> LENGTH: 43
<212> TYPE: DNA
<213> ORGANISM: Homo sapiens

<400> SEQUENCE: 508
aattaaccct cactaaaggg agattgggcc aaaacaaata agc                        43
```

```
<210> SEQ ID NO 509
<211> LENGTH: 42
<212> TYPE: DNA
<213> ORGANISM: Homo sapiens

<400> SEQUENCE: 509
aattaaccct cactaaaggg agaacgtttc cattgtgcgg ta                          42

<210> SEQ ID NO 510
<211> LENGTH: 42
<212> TYPE: DNA
<213> ORGANISM: Homo sapiens

<400> SEQUENCE: 510
aattaaccct cactaaaggg agacaaccca ctctcccttg ga                          42

<210> SEQ ID NO 511
<211> LENGTH: 43
<212> TYPE: DNA
<213> ORGANISM: Homo sapiens

<400> SEQUENCE: 511
aattaaccct cactaaaggg agaaggagta gcaggagcgt ggt                         43

<210> SEQ ID NO 512
<211> LENGTH: 41
<212> TYPE: DNA
<213> ORGANISM: Homo sapiens

<400> SEQUENCE: 512
aattaaccct cactaaaggg agaagcgaac gagaggtgag c                           41

<210> SEQ ID NO 513
<211> LENGTH: 41
<212> TYPE: DNA
<213> ORGANISM: Homo sapiens

<400> SEQUENCE: 513
aattaaccct cactaaaggg agatggcgcg tgaagaagtt g                           41

<210> SEQ ID NO 514
<211> LENGTH: 44
<212> TYPE: DNA
<213> ORGANISM: Homo sapiens

<400> SEQUENCE: 514
aattaaccct cactaaaggg agagcaaaga atcacacaca cacc                        44

<210> SEQ ID NO 515
<211> LENGTH: 49
<212> TYPE: DNA
<213> ORGANISM: Homo sapiens

<400> SEQUENCE: 515
aattaaccct cactaaaggg agacagaaat atgcaacagt tacaaaagg                   49

<210> SEQ ID NO 516
<211> LENGTH: 43
<212> TYPE: DNA
<213> ORGANISM: Homo sapiens

<400> SEQUENCE: 516
aattaaccct cactaaaggg agaccttcag gtttgggaac tca                         43
```

-continued

<210> SEQ ID NO 517
<211> LENGTH: 42
<212> TYPE: DNA
<213> ORGANISM: Homo sapiens

<400> SEQUENCE: 517
aattaaccct cactaaaggg agacctcatg aagggggaga tg          42

<210> SEQ ID NO 518
<211> LENGTH: 41
<212> TYPE: DNA
<213> ORGANISM: Homo sapiens

<400> SEQUENCE: 518
aattaaccct cactaaaggg agagtggctc ggtctccaca c           41

<210> SEQ ID NO 519
<211> LENGTH: 43
<212> TYPE: DNA
<213> ORGANISM: Homo sapiens

<400> SEQUENCE: 519
aattaaccct cactaaaggg agatactgct tggagtgctc ctc         43

<210> SEQ ID NO 520
<211> LENGTH: 43
<212> TYPE: DNA
<213> ORGANISM: Homo sapiens

<400> SEQUENCE: 520
aattaaccct cactaaaggg agatcacaaa gcggaagaat gtg         43

<210> SEQ ID NO 521
<211> LENGTH: 43
<212> TYPE: DNA
<213> ORGANISM: Homo sapiens

<400> SEQUENCE: 521
aattaaccct cactaaaggg agatggttct cccgagaggt aaa         43

<210> SEQ ID NO 522
<211> LENGTH: 43
<212> TYPE: DNA
<213> ORGANISM: Homo sapiens

<400> SEQUENCE: 522
aattaaccct cactaaaggg agaccctgat gacatcctga ttg         43

<210> SEQ ID NO 523
<211> LENGTH: 46
<212> TYPE: DNA
<213> ORGANISM: Homo sapiens

<400> SEQUENCE: 523
aattaaccct cactaaaggg agatcacttt ccataaaagc aaggtt      46

<210> SEQ ID NO 524
<211> LENGTH: 43
<212> TYPE: DNA
<213> ORGANISM: Homo sapiens

<400> SEQUENCE: 524
aattaaccct cactaaaggg agatgtactt cagggcttgg tca         43

<210> SEQ ID NO 525
<211> LENGTH: 43
<212> TYPE: DNA
<213> ORGANISM: Homo sapiens

<400> SEQUENCE: 525
aattaaccct cactaaaggg agacaagcca ctgaaggagc ata         43

<210> SEQ ID NO 526
<211> LENGTH: 46
<212> TYPE: DNA
<213> ORGANISM: Homo sapiens

<400> SEQUENCE: 526
aattaaccct cactaaaggg agaggcagga gatgagaatt aagaaa      46

<210> SEQ ID NO 527
<211> LENGTH: 43
<212> TYPE: DNA
<213> ORGANISM: Homo sapiens

<400> SEQUENCE: 527
aattaaccct cactaaaggg agaggctgat ccttcccaga aat         43

<210> SEQ ID NO 528
<211> LENGTH: 42
<212> TYPE: DNA
<213> ORGANISM: Homo sapiens

<400> SEQUENCE: 528
aattaaccct cactaaaggg agatgcagga gaaggtgaac ca          42

<210> SEQ ID NO 529
<211> LENGTH: 43
<212> TYPE: DNA
<213> ORGANISM: Homo sapiens

<400> SEQUENCE: 529
aattaaccct cactaaaggg agagaggatg aagcccacca aac         43

<210> SEQ ID NO 530
<211> LENGTH: 47
<212> TYPE: DNA
<213> ORGANISM: Homo sapiens

<400> SEQUENCE: 530
aattaaccct cactaaaggg agagagttgg gtgatacata cacaagg     47

<210> SEQ ID NO 531
<211> LENGTH: 43
<212> TYPE: DNA
<213> ORGANISM: Homo sapiens

<400> SEQUENCE: 531
aattaaccct cactaaaggg agatgagctg gtctgaatgt tcg         43

<210> SEQ ID NO 532
<211> LENGTH: 43
<212> TYPE: DNA
<213> ORGANISM: Homo sapiens

<400> SEQUENCE: 532

```
aattaaccct cactaaaggg agacagcagt cccaacagaa aca          43

<210> SEQ ID NO 533
<211> LENGTH: 43
<212> TYPE: DNA
<213> ORGANISM: Homo sapiens

<400> SEQUENCE: 533
aattaaccct cactaaaggg agagcagtgg tagtggtggc att          43

<210> SEQ ID NO 534
<211> LENGTH: 43
<212> TYPE: DNA
<213> ORGANISM: Homo sapiens

<400> SEQUENCE: 534
aattaaccct cactaaaggg agatggtgta acctcccttg aaa          43

<210> SEQ ID NO 535
<211> LENGTH: 43
<212> TYPE: DNA
<213> ORGANISM: Homo sapiens

<400> SEQUENCE: 535
aattaaccct cactaaaggg agatccctgc acttctaggc act          43

<210> SEQ ID NO 536
<211> LENGTH: 43
<212> TYPE: DNA
<213> ORGANISM: Homo sapiens

<400> SEQUENCE: 536
aattaaccct cactaaaggg agagcttcac tgggtgtgga aat          43

<210> SEQ ID NO 537
<211> LENGTH: 43
<212> TYPE: DNA
<213> ORGANISM: Homo sapiens

<400> SEQUENCE: 537
aattaaccct cactaaaggg agagtggaga ggaggaggac aaa          43

<210> SEQ ID NO 538
<211> LENGTH: 43
<212> TYPE: DNA
<213> ORGANISM: Homo sapiens

<400> SEQUENCE: 538
aattaaccct cactaaaggg agagcctcag acatctccag tcc          43

<210> SEQ ID NO 539
<211> LENGTH: 50
<212> TYPE: DNA
<213> ORGANISM: Homo sapiens

<400> SEQUENCE: 539
gtcgtcaaga tgctaccgtt caggagtcgt caagatgcta ccgttcagga          50

<210> SEQ ID NO 540
<211> LENGTH: 19
<212> TYPE: DNA
<213> ORGANISM: Homo sapiens

<400> SEQUENCE: 540
```

-continued

```
cttgacgact cctgaacgg                                    19

<210> SEQ ID NO 541
<211> LENGTH: 19
<212> TYPE: DNA
<213> ORGANISM: Homo sapiens

<400> SEQUENCE: 541
cttgacgaca cctgaacgg                                    19

<210> SEQ ID NO 542
<211> LENGTH: 23
<212> TYPE: DNA
<213> ORGANISM: Homo sapiens

<400> SEQUENCE: 542
taatacgact cactataggg aga                               23

<210> SEQ ID NO 543
<211> LENGTH: 23
<212> TYPE: DNA
<213> ORGANISM: Homo sapiens

<400> SEQUENCE: 543
aattaaccct cactaaaggg aga                               23
```